US008846886B2

(12) United States Patent
Jarvis et al.

(10) Patent No.: US 8,846,886 B2
(45) Date of Patent: Sep. 30, 2014

(54) LEPIDOPTERAN INSECT N-ACETYLGLUCOSAMINIDASE GENES AND THEIR USE IN GLYCOENGINEERING

(75) Inventors: Donald L. Jarvis, Laramie, WY (US); Christoph Geisler, Laramie, WY (US)

(73) Assignee: University of Wyoming, Laramie, WY (US)

( * ) Notice: Subject to any disclaimer, the term of this patent is extended or adjusted under 35 U.S.C. 154(b) by 759 days.

(21) Appl. No.: 12/746,808

(22) PCT Filed: Dec. 12, 2008

(86) PCT No.: PCT/US2008/086606
§ 371 (c)(1),
(2), (4) Date: Jun. 8, 2010

(87) PCT Pub. No.: WO2009/079376
PCT Pub. Date: Jun. 25, 2009

(65) Prior Publication Data
US 2010/0279415 A1    Nov. 4, 2010

Related U.S. Application Data

(60) Provisional application No. 61/013,815, filed on Dec. 14, 2007.

(51) Int. Cl.
| | |
|---|---|
| *C07H 21/04* | (2006.01) |
| *C12N 9/00* | (2006.01) |
| *C12N 9/10* | (2006.01) |
| *C12N 5/07* | (2010.01) |
| *C12N 5/00* | (2006.01) |
| *C12N 5/10* | (2006.01) |
| *C12N 15/00* | (2006.01) |
| *C12P 21/00* | (2006.01) |
| *C12N 9/24* | (2006.01) |

(52) U.S. Cl.
CPC ....... *C12N 9/2402* (2013.01); *C12Y 302/01096* (2013.01); *C12P 21/005* (2013.01)
USPC .......... 536/23.2; 435/183; 435/193; 435/348; 435/375; 435/455

(58) Field of Classification Search
CPC ............... C12Y 302/01052; C12Y 302/01014; C12Y 302/01096; C12Y 9/2402; C12Y 9/2405; C12Y 9/2442
See application file for complete search history.

(56) References Cited

U.S. PATENT DOCUMENTS
| | | | |
|---|---|---|---|
| 6,551,825 B1 | 4/2003 | Shirk et al. | |
| 2005/0208558 A1 | 9/2005 | Venter et al. | |

FOREIGN PATENT DOCUMENTS

WO    0129204 A2    4/2001

OTHER PUBLICATIONS

F. Altmann et al., "Insect Cells Contain an Unusual, Membrane-bound B-N-Acetylglucosaminidase Probably Involved in the Processing of Protein N-glycans", The Journal of Biological Chemistry, 270(29): 17344-17349 (1995).
S. Altschul et al., "Basic Local Alignment Search Tool", J. Mol. Biol., 215: 403-410 (1990).
S. Altschul et al., "Gapped BLAST and PSI-BLAST: a new generation of protein database search programs", Nucleic Acids Research, 25(17): 3389-3402 (1997).
J. Aumiller et al., "Molecular cloning and functional characterization of B-N-acetylglucosaminidase genes from Sf9 cells", Protein Expression and Purification, 47: 571-590 (2006).
S. Bao et al., "Fast cloning inverted repeats for RNA interference", RNA, 12: 2020-2024 (2006).
C. Breton et al., "Structural and functional features of glycosyltransferases", Biochimie, 83: 713-718 (2001).
S. Brunak et al., "Prediction of Human mRNA Donor and Acceptor Sites from the DNA Sequence", J. Mol. Biol., 220: 49-65 (1991).
L. Cary et al., "Transposon Mutagenesis of Baculoviruses: Analysis of Trichoplusia ni Transposon IFP2 Insertions within the FP-Locus of Nuclear Polyhedrosis Viruses", Virology, 172: 156-169 (1989).
J. Felsenstein, Phylip—Phylogeny Inference Package (Version 3.2):, Cladistics, 164-166 (1989).
M. Field et al., "Molecular cloning of eukaryotic glycoprotein and glycolipid glycosyltransferases: a survey", Glycobiology, 5(5): 463-472 (1995).
R. Fischer et al., "Plant-based production of biopharmaceuticals", Current Opinion in Plant Biology, 7: 152-158 (2004).
M. W. Gaunt et al., "An Insect Molecular Clock Dates the Origin of the Insects and Accords with Palaeontological and Biogeographic Landmarks", Mol. Biol. Eval., 19(5): 748-761 (2002).
C. Geisler et al., "A fused lobes Gene Encodes the Processing B-N-Acetylglucosaminidase in Sf9 Cells", The Journal of Biological Chemistry, 283(17): 11330-11339 (2008).
G. Grossman et al., "The piggyBac element is capable of precise excision and transposition in cells and embryos of the mosquito, *Anopheles gambiae*", Insect Biochemistry and Molecular Biology, 30: 909-914 (2000).
M. Gutternigg et al., "Biosynthesis of Truncated N-Linked Oligosaccharides Results from Non-orthologous Hexosaminidase-mediated Mechanisms in Nematodes, Plants, and Insects", Journal of Biological Chemistry, 282(38): 27825-27840 (2007).
U. Hacker et al., "piggyBac—based insertional mutagenesis in the presence of stably integrated P elements in *Drosophila*", PNAS, 100(13): 7720-7725 (2003).
A. Handler et al., "The lepidopteran transposon vector, piggyBac, mediates germ-line transformation in the Mediterranean fruit fly", Proc. Natl. Acad. Sci. USA, 95: 7520-7525 (1998).
S. Hebsgaard et al., "Splice site prediction in *Arabidopsis thaliana* pre-mRNA by combining local and global sequence information", Nucleic Acids Research, 24(17): 3439-3452 (1996).

(Continued)

*Primary Examiner* — Maria Leavitt
*Assistant Examiner* — Kimberly A Aron
(74) *Attorney, Agent, or Firm* — Patrick J. Hagan; Dann, Dorfman, Herrell and Skillman, P.C.

(57) ABSTRACT

A transgenic insect cell line for production of elevated levels of recombinant glycoproteins comprising mammalian-like N-glycans is provided. Also disclosed are nucleic acid sequences encoding β-N-acetylglucosaminidases.

17 Claims, 12 Drawing Sheets

(56) References Cited

OTHER PUBLICATIONS

K. Hofmann et al., "A Database of Membrane Spanning Protein Segments", Biol. Chem. Hoppe-Seyler, 374: 166 (1993).

C. Horn et al., "piggyBac—Based Insertional Mutagenesis and Enhancer Detection as a Tool for Functional Insect Genomics", Genetics, 163: 647-661 (2003).

D. Jarvis et al., "Immediate-Early Baculovirus Vectors for Foreign Gene Expression in Transformed or Infected Insect Cells", Protein Expression and Purification, 8: 191-203 (1996).

D. Jarvis et al., "Use of Early Baculovirus Promoters for Continuous Expression and Efficient Processing of Foreign Gene Products in Stably Transformed Lepidopteran Cells", Biotechnology, 8: 950-955 (1990).

D. Jarvis et al., "Baculovirus Expression Vectors", In: Miller, L.K. (ed.), The Baculoviruses, Plenum Press, NY (1997).

P. Kitts et al., "A Method for Producing Recombinant Baculovirus Expression Vectors at High Frequency", BioTechniques, 14(5): 810-817 (1993).

R. Kornfeld et al., "Assembly of Asparagine-Linked Oligosaccharides", Ann. Rev. Biochem., 54: 631-64 (1985).

P. Laird et al., "Simplified mammalian DNA isolation procedure", Nucleic Acids Research, 19(15): 4293 (1991).

R. Leonard et al., "The *Drosophila* fused lobes Gene Encodes an N-Acetylglucosaminidase Involved in N-Glycan Processing", The Journal of Biological Chemistry, 281(8): 4867-4875 (2006).

X. Li et al., "The minimum internal and external sequence requirements for transposition of the eukaryotic transformation vector piggyBac", Mol. Genet. Genomics, 266: 190-198 (2001).

N. Lobo et al., "Transposition of the piggyBac element in embryos of *Drosophila melanogaster*, *Aedes aegypti* and *Trichoplusia* ni", Mol. Gen. Genet., 261: 801-810 (1999).

N. Lobo et al., "Mobility of the piggyBac transposon in embryos of the vectors of Dengue fever (*Aedes albopictus*) and La Crosse encephalitis (*Ae. triseriatus*)", Mol. Genet. Genomics, 265: 66-71 (2001).

M. Lorenzen et al., "piggyBac—mediated germline transformation in the beetle *Tribolium castaneium*", Insect Molecular Biology, 12(5): 433-440 (2003).

J. Ma et al., "The Production of Recombinant Pharmaceutical Proteins in Plants", Nat. Rev. Genetics, 4: 794-805 (2003).

I. Marchal et al., "Glycoproteins from Insect Cells: Sialylated or Not?", Biol. Chem., 382: 151-159 (2001).

S. Maeda et al., "Production of human alpha-interferon in silkworm using a baculovirus vector", Nature: 315: 592-594 (1985).

R. Myerowitz et al., "Human beta-hexosaminidase alpha chain: Coding sequence and homology with the beta chain", Proc. Natl. Acad. Sci. USA, 82: 7830-7834 (1985).

B. O'Dowd et al., "Isolation of cDNA clones coding for the beta subunit of human beta-hexosaminidase", Proc. Natl. Acad. Sci. USA, 82: 1184-1188 (1985).

J. Paulson et al., "Glycosyltransferases—Structure, Localization and Control of Cell Type-Specific Glycosylation", The Journal of Biological Chemistry, 264(30): 17615-17618 (1989).

S. Shi et al., "A new rapid amplification of cDNA ends method for extremely guanine plus cytosine-rich genes", Analytical Biochemistry, 356: 222-228 (2006).

M. Sumitani et al., "Germline transformation of the sawfly, *Athalia rosae* (Hymenoptera: Symphyta), mediated by a piggyBac-derived vector", Insect Biochemistry and Molecular Biology, 33: 449-458 (2003).

M. D. Summers et al., "A Manual of Methods for Baculovirus Vectors and Insect Cell Culture Procedures", Texas Agricalatural Experiment Station Bulletin No. 1555, 3-57 (1987).

J. Thompson et al., "The CLUSTAL_X windows interface: flexible strategies for multiple sequence alignment aided by quality analysis tools", Nucleic Acids Research, 25(24), 4876-4882 (1997).

M. Tomita et al., "Transgenic silkworms produce recombinant human type III procollagen in cocoons", Nature Biotechnology, 21: 52-56 (2003).

N. Tomiya et al., "Purification, Characterization, and Cloning of a Spodoptera frugiperda Sf9 beta-N-Acetylhexosaminidase That Hydrolyzes Terminal N-Acetylglucosamine on the N-Glycan Core", J. Biol. Chem., 281 (28): 19545-19560 (2006).

J. L. Vaughn et al., The Establishment of Two Cell Lines from the Insect Spodoptera Frugiperda (Lepidoptera; Noctuidae), In Vitro, 13(4) 213-217 (1977).

A. Vitale et al., "Transient N-Acetylglucosamine in the Biosynthesis of Phytohemagglutinin: Attachment in the Golgi Apparatus and Removal in Protein Bodies", J. Cell Biol., 99: 133-140 (1984).

G. von Heijne, "Membrane Protein Structure Prediction", J. Mol. Biol., 225: 487-494 (1992).

R. Wagner et al., "N-Acetyl-B-Glucosaminidase Accounts for Differences in Glycosylation of Influenza Virus Hemagglutinin Expressed in Insect Cells from a Baculovirus Vector", J. Virol., 70(6): 4103-4109 (1996).

T.J. Wickham et al., "Screening of Insect Cell Lines for the Production of Recombinant Proteins and Infectious Virus in the Baculovirus Expression System", Biotechnol., Prog., 8: 391-396 (1992).

W. Zhang et al., "Synthesis of paucimannose N-glycans by *Caenorhabditis elegans* requires prior actions of UDP-Nacetyl-D-glucosamine: alpha-3-D-mannoside B1,2-N-acetylglucosaminyltransferase I, alpha3,6-mannosidase II and a specific membrane-bound B-N-acetylglucosaminidase", Biochem. J., 372: 53-64 (2003).

Fig. 1

```
ATG AAG TGG TGG GGC GAC GCA CTG GGG CGC GGG GCG TCG GCG CAG TTC GCG CGC GTC GGC CGC ATG CGG CGC GCG  -   75
 M   K   W   W   G   D   A   L   G   R   G   A   S   A   Q   F   A   R   V   G   R   M   R   R   A  -   25
CTG CTG CTG CTG GCC GCC GCC GCC TGC ACG GCC GCC GCG CTG CTG TAC TGG CGC CAG CAG AGC GAC GAC CGC CCG  -  150
 L   L   L   L   A   A   A   A   C   T   A   A   A   L   L   Y   W   R   Q   Q   S   D   D   R   P  -   50
CAC AGG CCG CTG CAG GCG CTT TAT GCG GGC ATC GAG CCA CAA TGG ACA TGG GTT TGC CGA AAC TAT CGC TGC GAG  -  225
 H   R   P   L   Q   A   L   Y   A   G   I   E   P   Q   W   T   W   V   C   R   N   Y   R   C   E  -   75
CGG CTT CTC GCC TCG GAG TCA TCA ACT CTG CAG TCG CTT CAG ACG TGC AAC ATG CTA TGC GAC TCG ACA CAG CTG  -  300
 R   L   L   A   S   E   S   S   T   L   Q   S   L   Q   T   C   N   M   L   C   D   S   T   Q   L  -  100
TGG CCG CAG CCC ACG GGG CCC GTC AGC CTC GCC ACC GCC GTC GTG CCG GTG CGG GCT GAC GGC TTC AAG CTG CAG  -  375
 W   P   Q   P   T   G   P   V   S   L   A   T   V   V   P   V   R   A   D   G   F   K   L   Q  -  125
ATC GTC ACG TCT CCT TCT CGT GAT GTG TCG GAC CAC CTC GCC GAA GCC TTC GAG CTT ATG AAG GAG GAC ATG CGG  -  450
 I   V   T   S   P   S   R   D   V   S   D   H   L   A   E   A   F   E   L   M   K   E   D   M   R  -  150
GTG CTG GAG CGC AAC ATG GGC GCG GAC TCC CGC CCC AGT GAC TAC GGG TCC CCT CAC GAC GTG CAC GTG CGC GTC  -  525
 V   L   E   R   N   M   G   A   D   S   R   P   S   D   Y   G   S   P   H   D   V   H   V   R   V  -  175
GCC ATT AAC GGC AGC GGA GAC CCG CGC ATG CGT CTC GAC ACT GAC GAA AGC TAC AAG CTG GCC CTC AGA CCC ACC  -  600
 A   I   N   G   S   G   D   P   R   M   R   L   D   T   D   E   S   Y   K   L   A   L   R   P   T  -  200
AGG AAA ACG CTA GTA GCC GAT ATT ACG GCC CAC TCC TTC TGC GGC GCT AGG CAC GGC TTC GAA ACC CTG TCA CAA  -  675
 R   K   T   L   V   A   D   I   T   A   H   S   F   C   G   A   R   H   G   F   E   T   L   S   Q  -  225
ATA GTA TGG ATG GAT CCT TAT GCC AGT TCG TTG CTT ATT CTA GAA GCG GCT ACA GTG GTG GAT GCG CCA CGA TTT  -  750
 I   V   W   M   D   P   Y   A   S   S   L   L   I   L   E   A   A   T   V   V   D   A   P   R   F  -  250
CCA TAT CGT GGC TTG CTG CTG GAT ACA GCT CGG AAC TTC TTT CCG TCA GAA GAA ATT CTA CGA ACA ATA GAT GCC  -  825
 P   Y   R   G   L   L   L   D   T   A   R   N   F   F   P   S   E   E   I   L   R   T   I   D   A  -  275
ATG GCT GCA TCC AAA ATG AAC ACA TTT CAC TGG CAC GTA AGT GAC TCG CAG TCG TTC CCA CTG CGG CTG GAC AGC  -  900
 M   A   A   S   K   M   N   T   F   H   W   H   V   S   D   S   Q   S   F   P   L   R   L   D   S  -  300
GCG CCG CAG CTG CAG CAG CAC GGC GCG TAC GGG CCG GGC GCC GTG TAC ACG CCG GAC GAC GTG CGG GCC ATC GTG  -  975
 A   P   Q   L   Q   Q   H   G   A   Y   G   P   G   A   V   Y   T   P   D   D   V   R   A   I   V  -  325
CGG CAC GCC AAG CTG CGC GGC ATC CGC GTG CTC ATG GAG GTG GAC GCG CCC GCT CAC GTG GGC CGC GCC TGG GGC  - 1050
 R   H   A   K   L   R   G   I   R   V   L   M   E   V   D   A   P   A   H   V   G   R   A   W   G  -  350
TGG GGG CCC GGC GCC GGC CTG GGC CAG CTC GCG CAC TGC ATC GAG GCC GAG CCC TGG AGC GCC TAC TGC GGG GAG  - 1125
 W   G   P   G   A   G   L   G   Q   L   A   H   C   I   E   A   E   P   W   S   A   Y   C   G   E  -  375
CCG CCC TGC GGA CAG CTT AAC CCC AGA AAC CCT CAC GTT TAC GAC TTG CTG CAG CGA ATT TAT ACT GAG ATC ATA  - 1200
 P   P   C   G   Q   L   N   P   R   N   P   H   V   Y   D   L   L   Q   R   I   Y   T   E   I   I  -  400
CAG TTG ACG GAG GTC GAC GAC CTG TTT CAC CTC GGC GGA GAT GAA GTG TCC GAG CGC TGC TGG GCT CAA CAC TTT  - 1275
 Q   L   T   E   V   D   D   L   F   H   L   G   G   D   E   V   S   E   R   C   W   A   Q   H   F  -  425
AAT GAT TCA GAT CCC ATG GAA TTG TGG TTG GAA TTT ACA AAG AAA GCC ATG CAA GCC CTG GAG CGT GCC AAC CAT  - 1350
 N   D   S   D   P   M   E   L   W   L   E   F   T   K   K   A   M   Q   A   L   E   R   A   N   H  -  450
GGG AAA GCA CCT GAA CTA ACG CTG TTA TGG TCG TCG CGC CTG ACG CGC TCA CCG TAC TTA GAG CGG CTA GAC TCT  - 1425
 G   K   A   P   E   L   T   L   L   W   S   S   R   L   T   R   S   P   Y   L   E   R   L   D   S  -  475
CGT CAC CTA GGC GTG CAG GTG TGG GGC TCC CGA TGG CCG GAG CGC GTC GCG GTC TTG GAC GCT GGA TTC CGG  - 1500
 R   H   L   G   V   Q   V   W   G   S   S   R   W   P   E   R   V   A   V   L   D   A   G   F   R  -  500
ACC GTG ATC TCG CAC GTG GAC GCC TGG TAC CTG GAC TGC GGC TTC GGC TCG TGG CGC GAC AGC TCG GAC GGC CAC  - 1575
 T   V   I   S   H   V   D   A   W   Y   L   D   C   G   F   G   S   W   R   D   S   S   D   G   H  -  525
TGC GGG CCT TAC CGC TCT TGG CAG CAG GTG TAC GAG CAC CGC CCG TGG ACC GAG GAG AAC GGC GGC GGC GGC GGC  - 1650
 C   G   P   Y   R   S   W   Q   Q   V   Y   E   H   R   P   W   T   E   E   N   G   G   G   G   G  -  550
ATC GGC AAC GCT GCG CCA CTG GTG GGC GGG GGA GCG GGG GGC GCG GGC GGG CCC GGG GGC GCG GCG GCC TGG CGC  - 1725
 I   G   N   A   A   P   L   V   G   G   G   A   G   G   A   G   G   P   G   G   A   A   A   W   R  -  575
GTG GAG GGC GGC GCG GCG TGC CAG TGG ACG GAG CAG CTG GCG CCG GGC GGG CTG GAC GCG CGC GTG TGG CCG CGC  - 1800
 V   E   G   G   A   A   C   Q   W   T   E   Q   L   A   P   G   G   L   D   A   R   V   W   P   R  -  600
TCG GCG GCG CTG GCG GAG CGC CTG TGG TCG GAC CGC GCG GAG GGC GCG GCG GCC GAC GTG TAC CTG CGC CTG GAC  - 1875
 S   A   A   L   A   E   R   L   W   S   D   R   A   E   G   A   A   A   D   V   Y   L   R   L   D  -  625
ACG CAG CGC GCC CGG CTG GTG GCG CGC GGC GTG CGG GCC GCG CCG CTG TGG CCG CGC TGG TGC TCG CAC AAC CCG  - 1950
 T   Q   R   A   R   L   V   A   R   G   V   R   A   A   P   L   W   P   R   W   C   S   H   N   P  -  650
CAC GCC TGC CTC TAG CTGCCACACACACACTCACACTCACCACTTCCCTGAGCGATCCGCGGGTGATGACCGACTTGCGAGATCCTGAACATCC  - 2044
 H   A   C   L   *                                                                                  -  654
TTCTGTTGTACATATAGCATTTAACCGTTTAGAGTAGAATAGCAAGTAGGTAGTAATTGTACAGCGCGTATTGTTATTATTTGATATAGCTAGATCGCG  - 2143
GAGGCACGCGCGTCGGACTGCGGACGGCAGCAGTGGGACGCGTGAGGACGGCGCCATAGTGCGGACCGCGACAGTGTTACTGCCATTGAGTCACAAGTA  - 2242
TTCCATCATTAATATTCGCATGTTTAAAGTAGGTACATAATAAATCGTGTTACATAGAAAAAAAAAAAAAAAAA                          - 2316
```

Fig. 8

```
                                    TTTTTTGGTCTTTTGTCACGGACCCCAAGGAGTGGAAAAATAGAAAACAAACATTTGATATGA  - -199
CGAGCGGTGTGTGTGTGTGTTTTTCGTGAATTTGATTCGCTGTCGTCTGCATTAAGCTCTGTGCACCTATTTCTGCACATTTCTGTTACGAAACAAACT  - -100
GCCCATGAGCCACTTTGAAGGATGGCAAAATACATTTGAAGATTGCTCAAAGAGCTTAATCAAAAAGCGATTGTAATGCTGCATCGATAGGTGATGAAG  -   -1
```

| ATG | ATG | TCG | TGG | GGT | GAT | GCA | TTA | TGG | CTC | GGC | TTG | ACG | GCG | AGA | TTT | GCG | AGG | GTG | GGG | CGG | CTG | CGA | CGA | GCC | -  75 |
|---|---|---|---|---|---|---|---|---|---|---|---|---|---|---|---|---|---|---|---|---|---|---|---|---|---|
| M | M | S | W | G | D | A | L | W | L | G | L | T | A | R | F | A | R | V | G | R | L | R | R | A | -  25 |

| GTG | CTC | ATG | CTG | GCC | GCG | GCC | GCC | TGC | ACC | GCT | GCT | GCT | GTA | CTC | TAC | TGG | AAA | CAG | CAG | ACT | GAC | GAC | AGC | GCC | - 150 |
| V | L | M | L | A | A | A | A | C | T | A | A | A | V | L | Y | W | K | Q | Q | T | D | D | S | A | -  50 |

| AAC | AGA | CCG | CTT | CAC | TCC | ATG | TAT | TCG | GGC | ATC | GAA | CCT | CAG | TGG | TCT | TGG | TTA | TGT | CAA | CAC | GAC | CGA | TGC | GAG | - 225 |
| N | R | P | L | H | S | M | Y | S | G | I | E | P | Q | W | S | W | L | C | Q | H | D | R | C | E | -  75 |

| AGG | TAT | CAA | GCG | TCG | GAT | ACG | ACG | ACG | CTA | CAG | TCG | CTG | CAG | ACT | TGC | AAC | ATG | CTG | TGC | GCC | TCC | ACC | CAG | CTC | - 300 |
| R | Y | Q | A | S | D | T | T | T | L | Q | S | L | Q | T | C | N | M | L | C | A | S | T | Q | L | - 100 |

| TGG | CCA | CAG | CCG | ACG | GGG | CCT | GTC | AGC | CTC | GCA | TCT | GCG | GCT | GTG | CCC | GTG | AGA | TCG | GAC | CGC | TTC | TCC | CTC | AAA | - 375 |
| W | P | Q | P | T | G | P | V | S | L | A | S | A | A | V | P | V | R | S | D | R | F | S | L | K | - 125 |

| GTT | ATA | GCG | TCA | CCA | TCA | CGC | GAC | GTC | ACC | AAA | CAC | ATA | AAC | GAA | GCG | TTT | ATC | GTG | ATG | CAA | AAT | CAC | ATG | CGA | - 450 |
| V | I | A | S | P | S | R | D | V | T | K | H | I | N | E | A | F | I | V | M | Q | N | H | M | R | - 150 |

| ACT | TTA | GAA | CAT | GGC | GTG | GTC | GGT | GAA | AAC | CGT | CGG | TCT | GAC | ATA | GGA | CCC | CCG | CGG | GAC | GTA | CTC | GTG | AAG | GTA | - 525 |
| T | L | E | H | G | V | V | G | E | N | R | R | S | D | I | G | P | P | R | D | V | L | V | K | V | - 175 |

| TCC | GTG | AAC | GGG | TCC | GGC | GAC | CCT | CGC | ATG | CGG | CTC | GAC | ACG | AAC | GAA | AGC | TAC | AAA | CTC | GCC | TTA | CGG | CCC | TCC | - 600 |
| S | V | N | G | S | G | D | P | R | M | R | L | D | T | N | E | S | Y | K | L | A | L | R | P | S | - 200 |

| GGC | AAT | TCC | CTC | GTC | GTA | GAC | ATC | ACA | GCG | CAT | TCG | TTC | TGC | GGA | GCG | AGA | CAC | GGC | CTC | GAA | ACA | CTT | TTG | CAG | - 675 |
| G | N | S | L | V | V | D | I | T | A | H | S | F | C | G | A | R | H | G | L | E | T | L | L | Q | - 225 |

| GTC | ACC | TGG | CTG | GAT | CCG | TAC | GCC | GGA | TCG | TTA | CTC | ATA | CTC | GAA | GCG | GCA | ACT | GTA | GTT | GAT | GCT | CCT | CGT | TTT | - 750 |
| V | T | W | L | D | P | Y | A | G | S | L | L | I | L | E | A | A | T | V | V | D | A | P | R | F | - 250 |

| CCT | TAC | CGT | GGC | CTA | CTT | CTG | GAT | ACG | GCT | CGT | AAT | TTT | TTC | CCC | GTC | AGT | GAG | CTT | CTC | CGC | ACC | ATA | GAC | GCG | - 825 |
| P | Y | R | G | L | L | L | D | T | A | R | N | F | F | P | V | S | E | L | L | R | T | I | D | A | - 275 |

| ATG | GCC | GCG | AAC | AAA | CTA | AAC | ACG | TTC | CAC | TGG | CAC | GTG | AGC | GAT | TCA | CAA | TCG | TTT | CCG | TGG | AAG | TTA | GAC | AGC | - 900 |
| M | A | A | N | K | L | N | T | F | H | W | H | V | S | D | S | Q | S | F | P | W | K | L | D | S | - 300 |

| GCA | CCC | CAA | CTG | GCG | CAG | CAC | GGC | GCC | TAC | GGA | CCG | GGC | GCA | GTG | TAC | ACG | TCC | GAC | GAC | GTG | AGA | ACA | ATT | GTT | - 975 |
| A | P | Q | L | A | Q | H | G | A | Y | G | P | G | A | V | Y | T | S | D | D | V | R | T | I | V | - 325 |

| AAA | TAC | GCA | CGC | ATC | AGA | GGA | ATC | AGG | GTG | CTG | ATG | GAA | ATA | GAC | ACA | CCG | GCG | CAC | GTC | GGT | CGA | GCT | TTC | GGT | - 1050 |
| K | Y | A | R | I | R | G | I | R | V | L | M | E | I | D | T | P | A | H | V | G | R | A | F | G | - 350 |

| TGG | GGT | CCG | GAG | GCT | GGC | CTC | GGC | CAC | TTA | GCG | CAC | TGC | ATA | GAG | GCG | GAA | CCC | TGG | AGT | TCC | TAC | TGC | GGA | GAA | - 1125 |
| W | G | P | E | A | G | L | G | H | L | A | H | C | I | E | A | E | P | W | S | S | Y | C | G | E | - 375 |

| CCT | CCG | TGC | GGC | CAA | CTG | AAT | CCT | CGC | AAC | CCT | CAC | ATA | TAC | GAT | TTA | CTA | GAA | CAC | GTC | TAC | AGG | GAG | ATC | ATT | - 1200 |
| P | P | C | G | Q | L | N | P | R | N | P | H | I | Y | D | L | L | E | H | V | Y | R | E | I | I | - 400 |

| CAA | TTA | ACT | GAG | GTC | GAC | GAC | ATC | TTC | CAC | CTT | GGT | GGC | GAT | GAG | GTG | TCG | GAA | CAG | TGC | TGG | GCT | AAG | CAC | TTC | - 1275 |
| Q | L | T | E | V | D | D | I | F | H | L | G | G | D | E | V | S | E | Q | C | W | A | K | H | F | - 425 |

| AAT | GAT | ACG | GAT | CCG | ATG | GAT | CTT | TGG | ATG | GAG | TTC | ACG | CGA | CAA | GCC | ATG | CAC | GTT | CTC | GAA | CGA | GCG | AAT | GGG | - 1350 |
| N | D | T | D | P | M | D | L | W | M | E | F | T | R | Q | A | M | H | V | L | E | R | A | N | G | - 450 |

| GGT | AAA | GCG | CCA | GAG | CTC | ACT | CTG | CTT | TGG | TCA | TCG | CGA | TTG | ACG | CGC | TCC | CCG | TAC | CTC | GAA | CGC | CTC | GAC | CCA | - 1425 |
| G | K | A | P | E | L | T | L | L | W | S | S | R | L | T | R | S | P | Y | L | E | R | L | D | P | - 475 |

| AAA | CGC | TTT | GGC | GTA | CAA | GTG | TGG | GGC | GCG | TCG | CAG | TGG | CCC | GAG | TCG | CGT | GCG | GTT | TTG | GAC | GCC | GGC | TTC | CGA | - 1500 |
| K | R | F | G | V | Q | V | W | G | A | S | Q | W | P | E | S | R | A | V | L | D | A | G | F | R | - 500 |

| TCG | GTG | ATC | TCG | CAC | GTG | GAC | GCC | TGG | TAC | CTC | GAC | TGC | GGG | TTC | GGG | TCG | TGG | CGC | GAC | AGC | TCG | GAC | GGA | CAC | - 1575 |
| S | V | I | S | H | V | D | A | W | Y | L | D | C | G | F | G | S | W | R | D | S | S | D | G | H | - 525 |

| TGC | GGG | CCG | TAC | CGG | TCG | TGG | CAG | CAG | GTG | TAC | GAG | CAC | CGA | CCG | TGG | GCG | ACG | GAA | ACG | CCC | GAG | AGC | GCG | GCA | - 1650 |
| C | G | P | Y | R | S | W | Q | Q | V | Y | E | H | R | P | W | A | T | E | T | P | E | S | A | A | - 550 |

| TGG | CCG | GTG | GAA | GGT | GGC | GCG | GCG | TGC | CAG | TGG | ACG | GAG | CAG | TTG | GGT | CCG | GGC | GGG | TTG | GAC | GCG | CGC | GTG | TGG | - 1725 |
| W | P | V | E | G | G | A | A | C | Q | W | T | E | Q | L | G | P | G | G | L | D | A | R | V | W | - 575 |

| CCC | CGG | ACG | GCG | GCT | CTG | GCG | GAG | CGG | CTG | TGG | GCA | GAC | CGT | GCC | GAG | GGC | GCC | ACG | GCG | GAC | GTG | TAC | TTG | CGG | - 1800 |
| P | R | T | A | A | L | A | E | R | L | W | A | D | R | A | E | G | A | T | A | D | V | Y | L | R | - 600 |

| CTC | GAC | ACA | CAG | CGG | GCG | CGG | CTG | GTG | GCG | CGG | GGG | GTG | CGA | GCG | GCG | CCG | CTG | TGG | CCG | CGC | TGG | TGC | TCC | CAC | - 1875 |
| L | D | T | Q | R | A | R | L | V | A | R | G | V | R | A | A | P | L | W | P | R | W | C | S | H | - 625 |

| AAC | CCG | CAC | GCG | TGC | CTC | TAG | TGCAGCCCCTCTCCACTACAACGGTACAATCACAAACTAGATAAGAAATCGCCTTTTCGCATTAAAATTAT | - 1967 |
| N | P | H | A | C | L | * | | -  631 |

```
ACAATTTCCAAAAATAGTCGAAATTAAATTCAAATACGGAATCATTTGGTATAGCCAGTATTTTTCTCATAGATACTGTCAAAAGAGCGAAGTTTAGTT  - 2066
TTAGTTTTTTTGTTATTTTTAATTTACCTATGTTTTGACTACTATTAACAAATTTAATACTTACATAATTTTATCTTACTTTTAAAAGACAGATAATG  - 2165
TAAGTACTGGTAAAAAAAAAAAAAAAAAA                                                                       - 2193
```

Fig. 9

```
                                    TTTTTTGGTCTTTTGTCACGGACCCCAAGGAGTGGAAAAATAGAAAACAAACATTTGATATGA    - -199
CGAGCGGTGTGTGTGTGTGTTTTTCGTGAATTTGATTCGCTGTCGTCTGCATTAAGCTCTGTGCACCTATTTCTGCACATTTCTGTTACGAAACAAACT    - -100
GCCCATGAGCCACTTTGAAGGATGGCAAAATACATTTGAAGATTGCTCAAAGAGCTTAATCAAAAAGCGATTGTAATGCTGCATCGATAGGTGATGAAG    - -1

ATG ATG TCG TGG GGT GAT GCA TTA TGG CTC GGC TTG ACG GCG AGA TTT GCG AGG GTG GGG CGG CTG CGA CGA GCC   - 75
 M   M   S   W   G   D   A   L   W   L   G   L   T   A   R   F   A   R   V   G   R   L   R   R   A    - 25

GTG CTC ATG CTG GCC GCG GCC GCC TGC ACC GCT GCT GCT GTA CTC TAC TGG AAA CAG CAG ACT GAC GAC AGC GCC   - 150
 V   L   M   L   A   A   A   A   C   T   A   A   A   V   L   Y   W   K   Q   Q   T   D   D   S   A    - 50

AAC AGA CCG CTT CAC TCC ATG TAT TCG GGC ATC GAA CCT CAG TGG TCT TGG TTA TGT CAA CAC GAC CGA TGC GAG   - 225
 N   R   P   L   H   S   M   Y   S   G   I   E   P   Q   W   S   W   L   C   Q   H   D   R   C   E    - 75

AGG TAT CAA GCG TCG GAT ACG ACG ACG CTA CAG TCG CTG CAG ACT TGT AAC ATG CTG TGC GCC TCC ACC CAG CTC   - 300
 R   Y   Q   A   S   D   T   T   T   L   Q   S   L   Q   T   C   N   M   L   C   A   S   T   Q   L    - 100

TGG CCA CAG CCG ACG GGG CCC GTC AGC CTC GCA TCG GCG GCC GTG CCC GTG AGA TCG GAC CGC TTC TCC CTT AAA   - 375
 W   P   Q   P   T   G   P   V   S   L   A   S   A   A   V   P   V   R   S   D   R   F   S   L   K    - 125

GTT ATA GCG TCA CCA TCA CGC GAC GTC ACC AAA CAC TTA AAC GAA GCG TTT ATC GTG ATG CAA AAT CAC ATG CGA   - 450
 V   I   A   S   P   S   R   D   V   T   K   H   L   N   E   A   F   I   V   M   Q   N   H   M   R    - 150

ACT TTA GAA CAT GGC GTG GTC GGT GAA AAC CGT CGA TCT GAC ATA GGA CCC CCG CGG GAC GTA CTC GTG AAG GTG   - 525
 T   L   E   H   G   V   V   G   E   N   R   R   S   D   I   G   P   P   R   D   V   L   V   K   V    - 175

TCC GTG AAC GGA TCC GGC GAC CCT CGC ATG CGG CTC GAC ACG AAC GAA AGC TAC AAA CTC GCC TTA CGG CCC TCC   - 600
 S   V   N   G   S   G   D   P   R   M   R   L   D   T   N   E   S   Y   K   L   A   L   R   P   S    - 200

GGC AAT TCC CTC GTC GTA GAC ATC ACA GCG CAT TCG TTC TGC GGA GCG AGA CAC GGC CTC GAA ACA CTT TTG CAG   - 675
 G   N   S   L   V   V   D   I   T   A   H   S   F   C   G   A   R   H   G   L   E   T   L   L   Q    - 225

GTC ACC TGG CTG GAT CCG TAC GCC GGA TCG CTA CTC ATA CTA GAA GCG GCA ACT GTA GTT GAT GCC CCT CGT TTT   - 750
 V   T   W   L   D   P   Y   A   G   S   L   L   I   L   E   A   A   T   V   V   D   A   P   R   F    - 250

CCT TAC CGT GGC CTA CTT CTG GAT ACG GCT CGT AAT TTT TTC CCC GTC AGT GAG CTT CTC CGC ACC ATA GAC GCG   - 825
 P   Y   R   G   L   L   L   D   T   A   R   N   F   F   P   V   S   E   L   L   R   T   I   D   A    - 275

ATG GCC GCG AAC AAA CTA AAC ACG TTC CAC TGG CAC GTG AGC GAT TCA CAA TCG TTT CCG TGG AAG TTA GAC AGC   - 900
 M   A   A   N   K   L   N   T   F   H   W   H   V   S   D   S   Q   S   F   P   W   K   L   D   S    - 300

GCA CCC CAA CTG GCG CAG CAC GGC GCC TAC GGA CCG GGC GCA GTG TAC ACG TCC GAC GAC GTG AGA ACA ATT GTT   - 975
 A   P   Q   L   A   Q   H   G   A   Y   G   P   G   A   V   Y   T   S   D   D   V   R   T   I   V    - 325

AAA TAC GCA CGC ATC AGA GGA ATC AGG GTG CTG ATG GAA ATA GAC ACA CCG GCG CAC GTC GGT CGA GCT TTC GGG   - 1050
 K   Y   A   R   I   R   G   I   R   V   L   M   E   I   D   T   P   A   H   V   G   R   A   F   G    - 350

TGG GGT CCG GAG GCT GGC CTC GGC CAC TTA GCG CAC TGC ATA GAG GCG AAA CCC TGG AGT CCC TAC TGC GGA GAA   - 1125
 W   G   P   E   A   G   L   G   H   L   A   H   C   I   E   A   E   P   W   S   S   Y   C   G   E    - 375

CCT CCG TGC GGC CAA CTG AAT CCT CGC AAC CCT CAC ATA TAC GAT TTA CTA GAA CAC GTC TAC AGG GAG ATC ATT   - 1200
 P   P   C   G   Q   L   N   P   R   N   P   H   I   Y   D   L   L   E   H   V   Y   R   E   I   I    - 400

CAA TTA ACT GGG GTC GAC GAC ATC TTC CAC CTT GGT GGC GAT GAG GTG TCG GAA CAG TGC TGG GCT AAG CAC TTC   - 1275
 Q   L   T   G   V   D   D   I   F   H   L   G   G   D   E   V   S   E   Q   C   W   A   K   H   F    - 425

AAT GAT ACG GAT CCG ATG GAT CTT TGG ATG GAG TTC ACG CGA CAA GCC ATG CAC GTT CTC GAA CGA GCG AAT GGG   - 1350
 N   D   T   D   P   M   D   L   W   M   E   F   T   R   Q   A   M   H   V   L   E   R   A   N   G    - 450

GGT AAA GCG CCA GAG CTC ACT CTG CTT TGG TCA TCG CGA TTG ACG CGC TCC CCG TAC CTC GAA CGC CTC GAC CCA   - 1425
 G   K   A   P   E   L   T   L   L   W   S   S   R   L   T   R   S   P   Y   L   E   R   L   D   P    - 475

AAA CGC TTT GGC GTA CAT GTG TGG GGC GCG TCG CAG TGG CCC GAG TCG CGT GCG GTT TTG GAC GCC GGC TTC CGA   - 1500
 K   R   F   G   V   H   V   W   G   A   S   Q   W   P   E   S   R   A   V   L   D   A   G   F   R    - 500

TCG GTG ATC TCG CAC GTG GAC GCC TGG TAC CTC GAC TGC GGG TTC GGG TCG TGG CGC GAC AGC TCG GAC GGA CAC   - 1575
 S   V   I   S   H   V   D   A   W   Y   L   D   C   G   F   G   S   W   R   D   S   S   D   G   H    - 525

TGC GGG CCG TAC CGG TCG TGG CAG CAG GTG TAC GAG CAC CGA CCG TGG GCG ACG GAA ACG CCC GAG AGC GCG GCA   - 1650
 C   G   P   Y   R   S   W   Q   Q   V   Y   E   H   R   P   W   A   T   E   T   P   E   S   A   A    - 550

TGG CCG GTG GAG GGT GGC GCA GCG TGC CAG TGG ACG CAG CAG TTG GGT CCG GGC GGC TTG GAC GCC CGC GTG TGG   - 1725
 W   P   V   E   G   G   A   A   C   Q   W   T   Q   Q   L   G   P   G   G   L   D   A   R   V   W    - 575

CCC CGG ACG GCA GCT CTG GCG GAG CGG CTG TGG GCA GAC CGT GCC GAG GGC GCC ACG GCG GAT GTG TAC TTG CGG   - 1800
 P   R   T   A   A   L   A   E   R   L   W   A   D   R   A   E   G   A   T   A   D   V   Y   L   R    - 600

CTC GAC ACA CAG CGG GCG CGG CTG GTG GCG CGG GGG GTG CGG GCG GCG CCG CTG TGG CCG CGC TGG TGC TCC CAC   - 1875
 L   D   T   Q   R   A   R   L   V   A   R   G   V   R   A   A   P   L   W   P   R   W   C   S   H    - 625

AAC CCG CAC GCG TGC CTC TAG TGCAGCCCCTCTCCACTACAACGGTACAATCACAAACTAGATAAGAAATCGCCTTTTCGCATTAAAATTAT   - 1967
 N   P   H   A   C   L   *                                                                              - 631

ACAATTTCCAAAAATAGTCGAAATTAAATTCAAATACGGAATCATTTGGTATAGCCAGTATTTTTCTCATAGATACTGTCAAAAGAGCGAAGTTTAGTT   - 2066
TTAGTTTTTTTGTTATTTTTAATTTACCTATGTTTTGACTACTATTAACAAATTTAATACTTACATAATTTTATCTTACTTTTTAAAAGACAGATAATG   - 2165
TAAGTACTGGTAAAAAAAAAAAAAAAAAAA                                                                          - 2193
```

Fig. 10

Sf-fd1 sequence used for RNAi experiment; nucleotides 355 to 855 within coding sequence:

CCGAAGGATTCAAGCTCCAAATAGTGACGTCACCTTCCCGCGACGTCTCCGACCA
TCTCGCTGACGCCTTCGAACTGATGAAGGAGGACATGCGCACGTTGGAGCGCAG
CGCTGGCTCCGAGCGCCGCCCCGCTGACTACGGGCTGCCTCGCAACGTGCTCGTG
CGCGTCGCCATCAACGGCAGCGCCGACCCGCGCATGCGCCTCGACACAGATGAG
AGTTACAAACTGACCCTGCGGCCCTCCAGGAAGTCTCTCGTGGCCGACATCACCG
CTCACTCGTTCTGCGGCGCGCGGCACGGTCTCGAGACTCTCTCGCAAATTGTATG
GATGGACCCTTACGCGGGTTGCTTGCTCATACTAGAGGCAGCTACTGTAGTCGAC
GCACCACGGTTCCCATATCGCGGACTTCTCCTTGACACAGCTCGAAACTTTTTCCC
GACTGGGGAGATACTACGGACAATAGACGCCATGGCTGCGTCTAAAATGAACAC
GTTCCAC

Fig. 12

SEQUENCE LISTING

<160> NUMBER OF SEQ ID NOS: 56

<210> SEQ ID NO 1
<211> LENGTH: 2319
<212> TYPE: DNA
<213> ORGANISM: Spodoptera frugiperda

<400> SEQUENCE: 1

```
gaaaattaaa accttaatgt aatggtgcgt agataggcag tgcgatgaag tggtggggcg      60
agggcctggg gcgcggtgcg tcggcgcagc tgtcgcgagt ggcgcgcatg cgccgcgccc     120
tgctgctcct ggcggcggcg gcgtgcacgg ccgcggcgct gctgtactgg cgccagcaga     180
gcgacgaccg cgcgcaccga ccgctgcacg ctctctacga aggcgtggaa ccacaatgga     240
gttgggtgtg tcgcaacctg cgctgcgagc ggctgctggc gacggagacc acgacgctgc     300
agtcgctgcc cacctgcaac atgctgtgcg actccacgca gctgtggccg cagcccacgg     360
gggcagtcag cctcgctact gcagtgcagc ctgtacgagc cgaaggattc aagctccaaa     420
tagtgacgtc accttcccgc gacgtctccg accatctcgc tgacgccttc gaactgatga     480
aggaggacat gcgcacgttg gagcgcagcg ctggctccga gcgccgcccc gctgactacg     540
ggctgcctcg caacgtgctc gtgcgcgtcg ccatcaacgg cagcgccgac ccgcgcatgc     600
gcctcgacac agatgagagt tacaaactga ccctgcggcc ctccaggaag tctctcgtgg     660
ccgacatcac cgctcactcg ttctgcggcg cgcggcacgg tctcgagact ctctcgcaaa     720
ttgtatggat ggaccttac gcgggttgct tgctcatact agaggcagct actgtagtcg     780
acgcaccacg gttcccatat cgcggacttc tccttgacac agctcgaaac ttttccccga     840
ctggggagat actacggaca atagacgcca tggctgcgtc taaatgaac acgttccact     900 ggcacgtgag tgactcgcag tcgttcccgc tgcggctgga cagcgcgccg cagctggcgc     960
agcacggggc gtacggcccc ggcgcggtgt acacctccga cgacgtgaag accatcgtgc    1020
ggcacgccaa gctgcgcggc atccgcgtgc tgctggaggt ggacgcgccc gcgcacgtcg    1080
gccgcgcctg gggctggggg cccagcgctg ggctcggcca cctcgcacac tgcgtcgagc    1140
tcgagccctg gagcgcgtat tgcggggagc cgccctgtgg acagctcaac ccgagaaacc    1200
cgcacgtgta cgatctactg caacgcatct acgctgagat tctcgcgcta acggaggtcg    1260
acgatgtgtt ccacttaggg ggagacgaag tgtcggaacg ttgctgggcg cagcacttca    1320
acgacaccga cccaatggat ttatggctag agttcacgcg acgtgctttg cacgcgttgg    1380
agcgcgccaa cggcggcaag ctgccggagc tagtgttact gtggtcgtcg cggctgactc    1440
gctcgccgta cctggagcgg ctggactcgc ggcacctggg cgtgcaggtg tggggctcct    1500
cgcggtggcc ggagtcccgc gccgtgctgg acgccgggtt ccggtcggtg ctgtcgcacg    1560
tggacgcgtg gtacctggac tgcggggttcg gctcgtggcg cgacagctcg gacgggcatt    1620
gcgggcccta ccgctcctgg cagcaggtgt acgagcaccg gccgtggacg gaggagggcg    1680
gcggcgcggc ggcgtggcgc gtggagggcg gcgcggcctg ccagtggacg gagcagctgg    1740
cggcgggcgg gctggacgcg cgcgtgtggc cccgcgccgc cgcgctggcc gagcgcctgt    1800
ggtcggaccg cgcggagggc gcgctgcccg acgtgtacct gcggctggac acgcagcgcg    1860
cgcggctgct ggcgcgcggc gtgcgcgcgg cgccgctgtg gccgcggtgg tgctcgcaca    1920
acccgcacgc ctgcctgtag gcgccgccgg gtggccacgc tttgtgttat cgtttccgtt    1980
actatattgt gttcccgagt tagaccactg ccctcgagtt acaagtattc gtttactgta    2040
tccgtactca gtagttacat aacaaaacgg ttacatagct aggcggatga cgtgtgtgat    2100
```

```
aagaaactat aacttattga actgttccaa tatgaatgca cagcgagtgg gaacgccgcg      2160
gatacagact gttaccaagt ggacttgata taatatacta ggtttgtgta atgatgacta      2220
acataaatcg catttatga aatgttgagc tttctctttt aatattatta aatatataaa      2280
cgttgctttg tttctgtaaa aaaaaaaaaa aaaaaaaaa                              2319
```

<210> SEQ ID NO 2
<211> LENGTH: 631
<212> TYPE: PRT
<213> ORGANISM: Spodoptera frugiperda

<400> SEQUENCE: 2

```
Met Lys Trp Trp Gly Glu Gly Leu Gly Arg Gly Ala Ser Ala Gln Leu
  1               5                  10                  15

Ser Arg Val Ala Arg Met Arg Arg Ala Leu Leu Leu Ala Ala Ala
             20                  25                  30

Ala Cys Thr Ala Ala Ala Leu Leu Tyr Trp Arg Gln Gln Ser Asp Asp
         35                  40                  45

Arg Ala His Arg Pro Leu His Ala Leu Tyr Glu Gly Val Glu Pro Gln
     50                  55                  60

Trp Ser Trp Val Cys Arg Asn Leu Arg Cys Glu Arg Leu Leu Ala Thr
 65                  70                  75                  80

Glu Thr Thr Thr Leu Gln Ser Leu Pro Thr Cys Asn Met Leu Cys Asp
                 85                  90                  95

Ser Thr Gln Leu Trp Pro Gln Pro Thr Gly Ala Val Ser Leu Ala Thr
            100                 105                 110

Ala Val Gln Pro Val Arg Ala Glu Gly Phe Lys Leu Gln Ile Val Thr
        115                 120                 125

Ser Pro Ser Arg Asp Val Ser Asp His Leu Ala Asp Ala Phe Glu Leu
    130                 135                 140

Met Lys Glu Asp Met Arg Thr Leu Glu Arg Ser Ala Gly Ser Glu Arg
145                 150                 155                 160

Arg Pro Ala Asp Tyr Gly Leu Pro Arg Asn Val Leu Arg Val Ala
                165                 170                 175

Ile Asn Gly Ser Ala Asp Pro Arg Met Arg Leu Asp Thr Asp Glu Ser
            180                 185                 190

Tyr Lys Leu Thr Leu Arg Pro Ser Arg Lys Ser Leu Val Ala Asp Ile
        195                 200                 205

Thr Ala His Ser Phe Cys Gly Ala Arg His Gly Leu Glu Thr Leu Ser
    210                 215                 220

Gln Ile Val Trp Met Asp Pro Tyr Ala Gly Cys Leu Leu Ile Leu Glu
225                 230                 235                 240

Ala Ala Thr Val Val Asp Ala Pro Arg Phe Pro Tyr Arg Gly Leu Leu
                245                 250                 255

Leu Asp Thr Ala Arg Asn Phe Phe Pro Thr Gly Glu Ile Leu Arg Thr
            260                 265                 270

Ile Asp Ala Met Ala Ala Ser Lys Met Asn Thr Phe His Trp His Val
        275                 280                 285

Ser Asp Ser Gln Ser Phe Pro Leu Arg Leu Asp Ser Ala Pro Gln Leu
    290                 295                 300

Ala Gln His Gly Ala Tyr Gly Pro Gly Ala Val Tyr Thr Ser Asp Asp
305                 310                 315                 320

Val Lys Thr Ile Val Arg His Ala Lys Leu Arg Gly Ile Arg Val Leu
                325                 330                 335
```

```
Leu Glu Val Asp Ala Pro Ala His Val Gly Arg Ala Trp Gly Trp Gly
            340                 345                 350

Pro Ser Ala Gly Leu Gly His Leu Ala His Cys Val Glu Leu Glu Pro
        355                 360                 365

Trp Ser Ala Tyr Cys Gly Glu Pro Pro Cys Gly Gln Leu Asn Pro Arg
    370                 375                 380

Asn Pro His Val Tyr Asp Leu Leu Gln Arg Ile Tyr Ala Glu Ile Leu
385                 390                 395                 400

Ala Leu Thr Glu Val Asp Val Phe His Leu Gly Gly Asp Glu Val
            405                 410                 415

Ser Glu Arg Cys Trp Ala Gln His Phe Asn Asp Thr Asp Pro Met Asp
            420                 425                 430

Leu Trp Leu Glu Phe Thr Arg Arg Ala Leu His Ala Leu Glu Arg Ala
        435                 440                 445

Asn Gly Gly Lys Leu Pro Glu Leu Val Leu Leu Trp Ser Ser Arg Leu
    450                 455                 460

Thr Arg Ser Pro Tyr Leu Glu Arg Leu Asp Ser Arg His Leu Gly Val
465                 470                 475                 480

Gln Val Trp Gly Ser Ser Arg Trp Pro Glu Ser Arg Ala Val Leu Asp
            485                 490                 495

Ala Gly Phe Arg Ser Val Leu Ser His Val Asp Ala Trp Tyr Leu Asp
        500                 505                 510

Cys Gly Phe Gly Ser Trp Arg Asp Ser Ser Asp Gly His Cys Gly Pro
    515                 520                 525

Tyr Arg Ser Trp Gln Gln Val Tyr Glu His Arg Pro Trp Thr Glu Glu
    530                 535                 540

Gly Gly Gly Ala Ala Trp Arg Val Glu Gly Gly Ala Ala Cys Gln
545                 550                 555                 560

Trp Thr Glu Gln Leu Ala Ala Gly Gly Leu Asp Ala Arg Val Trp Pro
            565                 570                 575

Arg Ala Ala Ala Leu Ala Glu Arg Leu Trp Ser Asp Arg Ala Glu Gly
            580                 585                 590

Ala Leu Pro Asp Val Tyr Leu Arg Leu Asp Thr Gln Arg Ala Arg Leu
        595                 600                 605

Leu Ala Arg Gly Val Arg Ala Ala Pro Leu Trp Pro Arg Trp Cys Ser
    610                 615                 620

His Asn Pro His Ala Cys Leu
625                 630

<210> SEQ ID NO 3
<211> LENGTH: 2316
<212> TYPE: DNA
<213> ORGANISM: Trichoplusia ni

<400> SEQUENCE: 3
atgaagtggt gggggcgacgc actggggcgc ggggcgtcgg cgcagttcgc gcgcgtcggc      60
cgcatgcggc gcgcgctgct gctgctggcc gccgccgcct gcacggccgc cgcgctgctg     120
tactggcgcc agcagagcga cgaccgcccg cacaggccgc tgcaggcgct ttatgcgggc     180
atcgagccac aatggacatg ggtttgccga actatcgct gcgagcggct tctcgcctcg      240
gagtcatcaa ctctgcagtc gcttcagacg tgcaacatgc tatgcgactc gacacagctg     300
tggccgcagc ccacggggcc cgtcagcctc gccaccgccg tcgtgccggt gcgggctgac     360
ggcttcaagc tgcagatcgt cacgtctcct tctcgtgatg tgtcggacca cctcgccgaa     420
```

```
gccttcgagc ttatgaagga ggacatgcgg gtgctggagc gcaacatggg cgcggactcc    480
cgccccagtg actacgggtc ccctcacgac gtgcacgtgc gcgtcgccat taacggcagc    540
ggagacccgc gcatgcgtct cgacactgac gaaagctaca agctggccct cagacccacc    600
aggaagacgc tagtagccga tattacggcc cactccttct gcggcgctag cacggcttc     660 gaaaccctgt cacaaatagt atggatggat ccttatgcca gttcgttgct tattctagaa    720
gcggctacag tggtggatgc gccacgattt ccatatcgtg gcttgctgct ggatacagct    780
cggaacttct ttccgtcaga agaaattcta cgaacaatag atgccatggc tgcatccaaa    840
atgaacacat tcactggca cgtaagtgac tcgcagtcgt tcccactgcg gctggacagc    900
gcgccgcagc tggcgcagca cggcgcgtac gggccgggcg ccgtgtacac gccggacgac    960
gtgcgggcca tcgtgcggca cgccaagctg cgcggcatcc gcgtgctcat ggaggtggac   1020
gcgcccgctc acgtgggccg cgcctggggc tgggggcccg cgccggcct gggccagctc    1080 gcgcactgca tcgaggccga gccctggagc gcctactgcg gggagccgcc ctgcggacag   1140
cttaacccca gaaaccctca cgtttacgac ttgctgcagc gaatttatac tgagatcata   1200
cagttgacgg aggtcgacga cctgtttcac ctcggcggag atgaagtgtc cgagcgctgc   1260
tgggctcaac actttaatga ttcagatccc atggaattgt ggttggaatt tacaaagaaa   1320
gccatgcaag ccctggagcg tgccaaccat gggaaagcac ctgaactaac gctgttatgg   1380
tcgtcgcgcc tgacgcgctc accgtactta gagcggctag actctcgtca cctaggcgtg   1440
caggtgtggg gctcctcgcg atggccgag tcgcgtgcgg tcttggacgc tggattccgg    1500
accgtgatct cgcacgtgga cgcctggtac ctggactgcg gcttcggctc gtggcgcgac   1560
agctcggacg gccactgcgg gccttaccgc tcttggcagc aggtgtacga gcaccgcccg   1620
tggaccgagg agaacggcgg cggcggcggc atcggcaacg ctgcgccact ggtgggcggg   1680
ggagcggggg gcgcgggcgg gcccggggc gcggcggcct ggcgcgtgga gggcggcgcg    1740
gcgtgccagt ggacggagca gctggcgccg gcgggctgg acgcgcgcgt gtggccgcgc    1800
tcggcggcgc tggcggagcg cctgtggtcg gaccgcgcgg agggcgcggc ggccgacgtg   1860
tacctgcgcc tggacacgca gcgcgcgcgg ctggtggcgc gcggcgtgcg ggccgcgccg   1920
ctgtggccgc gctggtgctc gcacaacccg cacgcctgcc tctagctgcc acacacacac   1980
tcacactcac cacttccctg agcgatccgc gggtgatgac cgacttgcga atcctgaac    2040 atccttctgt tgtacatata gcatttaacc gtttagagta gaatagcaag taggtagtaa   2100
ttgtacagcg cgtattgtta ttatttgata tagctagatc gcggaggcac gcgcgtcgga   2160
ctgcggacgg cagcagtggg acgcgtgagg acggcgccat agtgcggacc gcgacagtgt   2220
tactgccatt gagtcacaag tattccatca ttaatattcg catgtttaaa gtaggtacat   2280
aataaatcgt gttacataga aaaaaaaaaa aaaaaa                             2316
```

<210> SEQ ID NO 4
<211> LENGTH: 654
<212> TYPE: PRT
<213> ORGANISM: Trichoplusia ni

<400> SEQUENCE: 4

Met Lys Trp Trp Gly Asp Ala Leu Gly Arg Gly Ala Ser Ala Gln Phe
 1               5                  10                  15

Ala Arg Val Gly Arg Met Arg Arg Ala Leu Leu Leu Leu Ala Ala Ala
            20                  25                  30

```
Ala Cys Thr Ala Ala Ala Leu Leu Tyr Trp Arg Gln Gln Ser Asp Asp
            35                  40                  45

Arg Pro His Arg Pro Leu Gln Ala Leu Tyr Ala Gly Ile Glu Pro Gln
 50                  55                  60

Trp Thr Trp Val Cys Arg Asn Tyr Arg Cys Glu Arg Leu Leu Ala Ser
 65              70                  75                  80

Glu Ser Ser Thr Leu Gln Ser Leu Gln Thr Cys Asn Met Leu Cys Asp
                85                  90                  95

Ser Thr Gln Leu Trp Pro Gln Pro Thr Gly Pro Val Ser Leu Ala Thr
            100                 105                 110

Ala Val Val Pro Val Arg Ala Asp Gly Phe Lys Leu Gln Ile Val Thr
            115                 120                 125

Ser Pro Ser Arg Asp Val Ser Asp His Leu Ala Glu Ala Phe Glu Leu
130                 135                 140

Met Lys Glu Asp Met Arg Val Leu Glu Arg Asn Met Gly Ala Asp Ser
145                 150                 155                 160

Arg Pro Ser Asp Tyr Gly Ser Pro His Asp Val His Val Arg Val Ala
                165                 170                 175

Ile Asn Gly Ser Gly Asp Pro Arg Met Arg Leu Asp Thr Asp Glu Ser
            180                 185                 190

Tyr Lys Leu Ala Leu Arg Pro Thr Arg Lys Thr Leu Val Ala Asp Ile
            195                 200                 205

Thr Ala His Ser Phe Cys Gly Ala Arg His Gly Phe Glu Thr Leu Ser
            210                 215                 220

Gln Ile Val Trp Met Asp Pro Tyr Ala Ser Ser Leu Leu Ile Leu Glu
225                 230                 235                 240

Ala Ala Thr Val Val Asp Ala Pro Arg Phe Pro Tyr Arg Gly Leu Leu
                245                 250                 255

Leu Asp Thr Ala Arg Asn Phe Phe Pro Ser Glu Glu Ile Leu Arg Thr
            260                 265                 270

Ile Asp Ala Met Ala Ala Ser Lys Met Asn Thr Phe His Trp His Val
            275                 280                 285

Ser Asp Ser Gln Ser Phe Pro Leu Arg Leu Asp Ser Ala Pro Gln Leu
            290                 295                 300

Ala Gln His Gly Ala Tyr Gly Pro Gly Ala Val Tyr Thr Pro Asp Asp
305                 310                 315                 320

Val Arg Ala Ile Val Arg His Ala Lys Leu Arg Gly Ile Arg Val Leu
                325                 330                 335

Met Glu Val Asp Ala Pro Ala His Val Gly Arg Ala Trp Gly Trp Gly
            340                 345                 350

Pro Gly Ala Gly Leu Gly Gln Leu Ala His Cys Ile Glu Ala Glu Pro
            355                 360                 365

Trp Ser Ala Tyr Cys Gly Glu Pro Pro Cys Gly Gln Leu Asn Pro Arg
370                 375                 380

Asn Pro His Val Tyr Asp Leu Leu Gln Arg Ile Tyr Thr Glu Ile Ile
385                 390                 395                 400

Gln Leu Thr Glu Val Asp Asp Leu Phe His Leu Gly Gly Asp Glu Val
                405                 410                 415

Ser Glu Arg Cys Trp Ala Gln His Phe Asn Asp Ser Asp Pro Met Glu
            420                 425                 430

Leu Trp Leu Glu Phe Thr Lys Lys Ala Met Gln Ala Leu Glu Arg Ala
            435                 440                 445

Asn His Gly Lys Ala Pro Glu Leu Thr Leu Leu Trp Ser Ser Arg Leu
```

```
                450               455               460
Thr Arg Ser Pro Tyr Leu Glu Arg Leu Asp Ser Arg His Leu Gly Val
465                 470                 475                 480

Gln Val Trp Gly Ser Ser Arg Trp Pro Glu Ser Arg Ala Val Leu Asp
                485                 490                 495

Ala Gly Phe Arg Thr Val Ile Ser His Val Asp Ala Trp Tyr Leu Asp
                500                 505                 510

Cys Gly Phe Gly Ser Trp Arg Asp Ser Ser Asp Gly His Cys Gly Pro
                515                 520                 525

Tyr Arg Ser Trp Gln Gln Val Tyr Glu His Arg Pro Trp Thr Glu Glu
                530                 535                 540

Asn Gly Gly Gly Gly Ile Gly Asn Ala Ala Pro Leu Val Gly Gly
545                 550                 555                 560

Gly Ala Gly Gly Ala Gly Gly Pro Gly Gly Ala Ala Trp Arg Val
                565                 570                 575

Glu Gly Gly Ala Ala Cys Gln Trp Thr Glu Gln Leu Ala Pro Gly Gly
                580                 585                 590

Leu Asp Ala Arg Val Trp Pro Arg Ser Ala Leu Ala Glu Arg Leu
                595                 600                 605

Trp Ser Asp Arg Ala Glu Gly Ala Ala Ala Asp Val Tyr Leu Arg Leu
                610                 615                 620

Asp Thr Gln Arg Ala Arg Leu Val Ala Arg Gly Val Arg Ala Ala Pro
625                 630                 635                 640

Leu Trp Pro Arg Trp Cys Ser His Asn Pro His Ala Cys Leu
                645                 650

<210> SEQ ID NO 5
<211> LENGTH: 2454
<212> TYPE: DNA
<213> ORGANISM: Bombyx mori

<400> SEQUENCE: 5 tttttggtc ttttgtcacg accccaagg agtggaaaaa tagaaaacaa acatttgata       60
tgacgagcgg tgtgtgtgtg tgtttttcgt gaatttgatt cgctgtcgtc tgcattaagc      120
tctgtgcacc tatttctgca catttctgtt acgaaacaaa ctgcccatga gccactttga      180
aggatggcaa aatacatttg aagattgctc aaagagctta atcaaaaagc gattgtaatg      240
ctgcatcgat aggtgatgaa gatgatgtcg tggggtgatg cattatggct cggcttgacg      300
gcgagatttg cgagggtggg gcggctgcga cgagccgtgc tcatgctggc gcggccgcc      360 tgcaccgctg ctgctgtact ctactggaaa cagcagactg acgacagcgc aacagaccg      420 cttcactcca tgtattcggg catcgaacct cagtggtctt ggttatgtca acacgaccga      480
tgcgagaggt atcaagcgtc ggatacgacg acgctacagt cgctgcagac ttgcaacatg      540
ctgtgcgcct ccacccagct ctggccacag ccgacgggc ctgtcagcct cgcatctgcg      600
gctgtgcccg tgagatcgga ccgcttctcc ctcaaagtta tagcgtcacc atcacgcgac      660
gtcaccaaac acataaacga agcgtttatc gtgatgcaaa atcacatgcg aactttagaa      720 catgcgtgg tcgtgaaaaa ccgtcggtct gacataggac cccgcggga cgtactcgtg      780 aaggtatccg tgaacgggtc ggcgaccct cgcatgcggc tcgacacgaa cgaaagctac      840
aaactcgcct tacggccctc cggcaattcc ctcgtcgtag acatcacagc gcattcgttc      900 tgcgagcga gacacggcct cgaaacactt ttgcaggtca cctggctgga tccgtacgcc      960
ggatcgttac tcatactcga agcggcaact gtagttgatg ctcctcgttt tccttaccgt     1020
```

```
ggcctacttc tggatacggc tcgtaattt ttccccgtca gtgagcttct ccgcaccata    1080
gacgcgatgg ccgcgaacaa actaaacacg ttccactggc acgtgagcga ttcacaatcg   1140
tttccgtgga agttagacag cgcaccccaa ctggcgcagc acggcgccta cggaccgggc   1200
gcagtgtaca cgtccgacga cgtgagaaca attgttaaat acgcacgcat cagaggaatc   1260
agggtgctga tggaaataga cacaccggcg cacgtcggtc gagctttcgg ttggggtccg   1320
gaggctggcc tcggccactt agcgcactgc atagaggcgg aaccctggag ttcctactgc   1380
ggagaacctc cgtgcggcca actgaatcct cgcaacccct acatatacga tttactagaa   1440
cacgtctaca gggagatcat tcaattaact gaggtcgacg acatcttcca ccttggtggc   1500
gatgaggtgt cggaacagtg ctgggctaag cacttcaatg atacggatcc gatggatctt   1560
tggatggagt tcacgcgaca agccatgcac gttctcgaac gagcgaatgg gggtaaagcg   1620
ccagagctca ctctgctttg gtcatcgcga ttgacgcgct ccccgtacct cgaacgcctc   1680
gacccaaaac gctttggcgt acaagtgtgg ggcgcgtcgc agtggcccga gtcgcgtgcg   1740
gttttggacg ccggcttccg atcggtgatc tcgcacgtgg acgcctggta cctcgactgc   1800
gggttcgggt cgtggcgcga cagctcggac ggacactgcg ggccgtaccg gtcgtggcag   1860
caggtgtacg agcaccgacc gtgggcgacg gaaacgcccg agagcgcggc atggccggtg   1920
gagggtggcg cggcgtgcca gtggacggag cagttgggtc cgggcgggtt ggacgcgcgc   1980
gtgtggcccc ggacggcggc tctggcggag cggctgtggg cagaccgtgc cgagggcgcc   2040
acggcggacg tgtacttgcg gctcgacaca cagcgggcgc ggctggtggc gcggggggtg   2100
cgggcggcgc cgctgtggcc gcgctggtgc tcccacaacc cgcacgcgtg cctctagtgc   2160 agccctctc cactacaacg gtacaatcac aaactagata agaaatcgcc ttttcgcatt    2220
aaaattatac aatttccaaa aatagtcgaa attaaattca aatacggaat catttggtat   2280
agccagtatt tttctcatag atactgtcaa aagagcgaag tttagtttta gttttttgt    2340 tattttaat ttacctatgt tttgactact attaacaaat ttaatactta cataatttta    2400
tcttactttt taaagacag ataatgtaag tactggtaaa aaaaaaaaa aaaa           2454
```

<210> SEQ ID NO 6
<211> LENGTH: 631
<212> TYPE: PRT
<213> ORGANISM: Bombyx mori

<400> SEQUENCE: 6

```
Met Met Ser Trp Gly Asp Ala Leu Trp Leu Gly Leu Thr Ala Arg Phe
 1               5                  10                  15

Ala Arg Val Gly Arg Leu Arg Arg Ala Val Leu Met Leu Ala Ala Ala
             20                  25                  30

Ala Cys Thr Ala Ala Ala Val Leu Tyr Trp Lys Gln Gln Thr Asp Asp
         35                  40                  45

Ser Ala Asn Arg Pro Leu His Ser Met Tyr Ser Gly Ile Glu Pro Gln
     50                  55                  60

Trp Ser Trp Leu Cys Gln His Asp Arg Cys Glu Arg Tyr Gln Ala Ser
 65                  70                  75                  80

Asp Thr Thr Thr Leu Gln Ser Leu Gln Thr Cys Asn Met Leu Cys Ala
                 85                  90                  95

Ser Thr Gln Leu Trp Pro Gln Pro Thr Gly Pro Val Ser Leu Ala Ser
            100                 105                 110

Ala Ala Val Pro Val Arg Ser Asp Arg Phe Ser Leu Lys Val Ile Ala
```

```
            115                 120                 125
Ser Pro Ser Arg Asp Val Thr Lys His Ile Asn Glu Ala Phe Ile Val
130                 135                 140

Met Gln Asn His Met Arg Thr Leu Glu His Gly Val Val Gly Glu Asn
145                 150                 155                 160

Arg Arg Ser Asp Ile Gly Pro Pro Arg Asp Val Leu Val Lys Val Ser
                165                 170                 175

Val Asn Gly Ser Gly Asp Pro Arg Met Arg Leu Asp Thr Asn Glu Ser
            180                 185                 190

Tyr Lys Leu Ala Leu Arg Pro Ser Gly Asn Ser Leu Val Val Asp Ile
        195                 200                 205

Thr Ala His Ser Phe Cys Gly Ala Arg His Gly Leu Glu Thr Leu Leu
    210                 215                 220

Gln Val Thr Trp Leu Asp Pro Tyr Ala Gly Ser Leu Leu Ile Leu Glu
225                 230                 235                 240

Ala Ala Thr Val Val Asp Ala Pro Arg Phe Pro Tyr Arg Gly Leu Leu
                245                 250                 255

Leu Asp Thr Ala Arg Asn Phe Phe Pro Val Ser Glu Leu Leu Arg Thr
            260                 265                 270

Ile Asp Ala Met Ala Ala Asn Lys Leu Asn Thr Phe His Trp His Val
        275                 280                 285

Ser Asp Ser Gln Ser Phe Pro Trp Lys Leu Asp Ser Ala Pro Gln Leu
    290                 295                 300

Ala Gln His Gly Ala Tyr Gly Pro Gly Ala Val Tyr Thr Ser Asp Asp
305                 310                 315                 320

Val Arg Thr Ile Val Lys Tyr Ala Arg Ile Arg Gly Ile Arg Val Leu
                325                 330                 335

Met Glu Ile Asp Thr Pro Ala His Val Gly Arg Ala Phe Gly Trp Gly
            340                 345                 350

Pro Glu Ala Gly Leu Gly His Leu Ala His Cys Ile Glu Ala Glu Pro
        355                 360                 365

Trp Ser Ser Tyr Cys Gly Glu Pro Pro Cys Gly Gln Leu Asn Pro Arg
    370                 375                 380

Asn Pro His Ile Tyr Asp Leu Leu Glu His Val Tyr Arg Glu Ile Ile
385                 390                 395                 400

Gln Leu Thr Glu Val Asp Asp Ile Phe His Leu Gly Gly Asp Glu Val
                405                 410                 415

Ser Glu Gln Cys Trp Ala Lys His Phe Asn Asp Thr Asp Pro Met Asp
            420                 425                 430

Leu Trp Met Glu Phe Thr Arg Gln Ala Met His Val Leu Glu Arg Ala
        435                 440                 445

Asn Gly Gly Lys Ala Pro Glu Leu Thr Leu Leu Trp Ser Ser Arg Leu
    450                 455                 460

Thr Arg Ser Pro Tyr Leu Glu Arg Leu Asp Pro Lys Arg Phe Gly Val
465                 470                 475                 480

Gln Val Trp Gly Ala Ser Gln Trp Pro Glu Ser Arg Ala Val Leu Asp
                485                 490                 495

Ala Gly Phe Arg Ser Val Ile Ser His Val Asp Ala Trp Tyr Leu Asp
            500                 505                 510

Cys Gly Phe Gly Ser Trp Arg Asp Ser Ser Asp Gly His Cys Gly Pro
        515                 520                 525

Tyr Arg Ser Trp Gln Gln Val Tyr Glu His Arg Pro Trp Ala Thr Glu
    530                 535                 540
```

```
Thr Pro Glu Ser Ala Ala Trp Pro Val Glu Gly Ala Ala Cys Gln
545                 550                 555                 560

Trp Thr Glu Gln Leu Gly Pro Gly Gly Leu Asp Ala Arg Val Trp Pro
                565                 570                 575

Arg Thr Ala Ala Leu Ala Glu Arg Leu Trp Ala Asp Arg Ala Glu Gly
            580                 585                 590

Ala Thr Ala Asp Val Tyr Leu Arg Leu Asp Thr Gln Arg Ala Arg Leu
        595                 600                 605

Val Ala Arg Gly Val Arg Ala Ala Pro Leu Trp Pro Arg Trp Cys Ser
    610                 615                 620

His Asn Pro His Ala Cys Leu
625                 630

<210> SEQ ID NO 7
<211> LENGTH: 2454
<212> TYPE: DNA
<213> ORGANISM: Bombyx mori

<400> SEQUENCE: 7 tttttggtc ttttgtcacg gaccccaagg agtggaaaaa tagaaaacaa acatttgata      60
tgacgagcgg tgtgtgtgtg tgttttcgt gaatttgatt cgctgtcgtc tgcattaagc     120
tctgtgcacc tatttctgca catttctgtt acgaaacaaa ctgcccatga gccactttga     180
aggatggcaa atacatttg aagattgctc aaagagctta atcaaaaagc gattgtaatg     240
ctgcatcgat aggtgatgaa gatgatgtcg tggggtgatg cattatggct cggcttgacg     300
gcgagatttg cgagggtggg gcggctgcga cgagccgtgc tcatgctggc cgcggccgcc     360
tgcaccgctg ctgctgtact ctactggaaa cagcagactg acgacagcgc caacagaccg     420
cttcactcca tgtattcggg catcgaacct cagtggtctt ggttatgtca acacgaccga     480
tgcgagaggt atcaagcgtc ggatacgacg acgctacagt cgctgcagac ttgtaacatg     540
ctgtgcgcct ccacccagct ctggccacag ccgacggggc ccgtcagcct cgcatcggcg     600
gccgtgcccg tgagatcgga ccgcttctcc cttaaagtta tagcgtcacc atcacgcgac     660
gtcaccaaac acttaaacga agcgtttatc gtgatgcaaa atcacatgcg aactttagaa     720
catggcgtgg tcggtgaaaa ccgtcgatct gacataggac ccccgcggga cgtactcgtg     780
aaggtgtccg tgaacggatc cggcgaccct cgcatgcggc tcgacacgaa cgaaagctac     840
aaactcgcct tacggccctc cggcaattcc ctcgtcgtag acatcacagc gcattcgttc     900
tgcggagcga gacacggcct cgaaacactt ttgcaggtca cctggctgga tccgtacgcc     960
ggatcgctac tcatactaga agcggcaact gtagttgatg cccctcgttt tccttaccgt    1020
ggcctacttc tggatacggc tcgtaatttt tccccgtca gtgagcttct ccgcaccata    1080
gacgcgatgg ccgcgaacaa actaaacacg ttccactggc acgtgagcga ttcacaatcg    1140
tttccgtgga agttagacag cgcacccccaa ctggcgcagc acggcgccta cggacccggc    1200
gcagtgtaca cgtccgacga cgtgagaaca attgttaaat acgcacgcat cagaggaatc    1260
agggtgctga tggaaataga cacaccggcg cacgtcggtc gagctttcgg gtggggtccg    1320
gaggctggcc tcggccactt agcgcactgc atagaggcgg aaccctggag ttcctactgc    1380
ggagaacctc cgtgcggcca actgaatcct cgcaacccctc acatatacga tttactagaa    1440
cacgtctaca gggagatcat tcaattaact ggggtcgacg acatcttcca ccttggtggc    1500
gatgaggtgt cggaacagtg ctgggctaag cacttcaatg atacgatcc gatggatctt    1560
```

-continued

```
tggatggagt tcacgcgaca agccatgcac gttctcgaac gagcgaatgg gggtaaagcg    1620
ccagagctca ctctgctttg gtcatcgcga ttgacgcgct ccccgtacct cgaacgcctc    1680
gacccaaaac gctttggcgt acatgtgtgg ggcgcgtcgc agtggcccga gtcgcgtgcg    1740
gttttggacg ccggcttccg atcggtgatc tcgcacgtgg acgcctggta cctcgactgc    1800
gggttcgggt cgtggcgcga cagctcggac ggacactgcg ggccgtaccg gtcgtggcag    1860
caggtgtacg agcaccgacc gtgggcgacg gaaacgcccg agagcgcggc atggccggtg    1920
gagggtggcg cagcgtgcca gtggacggag cagttgggtc cgggcgggtt ggacgcgcgc    1980
gtgtggcccc ggacggcagc tctggcggag cggctgtggg cagaccgtgc cgagggcgcc    2040
acggcggatg tgtacttgcg gctcgacaca cagcgggcgc ggctggtggc gcgggggtg    2100 cgggcggcgc cgctgtggcc gcgctggtgc tcccacaacc cgcacgcgtg cctctagtgc    2160
agcccctctc cactacaacg gtacaatcac aaactagata agaaatcgcc ttttcgcatt    2220
aaaattatac aatttccaaa atagtcgaa attaaattca atacggaat catttggtat     2280 agccagtatt tttctcatag atactgtcaa agagcgaag tttagttta gttttttgt      2340 tattttttaat ttacctatgt tttgactact attaacaaat ttaatactta cataatttta   2400 tcttacttt taaaagacag ataatgtaag tactggtaaa aaaaaaaaa aaaa            2454
```

<210> SEQ ID NO 8
<211> LENGTH: 631
<212> TYPE: PRT
<213> ORGANISM: Bombyx mori

<400> SEQUENCE: 8

```
Met Met Ser Trp Gly Asp Ala Leu Trp Leu Gly Leu Thr Ala Arg Phe
 1               5                  10                  15

Ala Arg Val Gly Arg Leu Arg Arg Ala Val Leu Met Leu Ala Ala Ala
             20                  25                  30

Ala Cys Thr Ala Ala Ala Val Leu Tyr Trp Lys Gln Gln Thr Asp Asp
         35                  40                  45

Ser Ala Asn Arg Pro Leu His Ser Met Tyr Ser Gly Ile Glu Pro Gln
     50                  55                  60

Trp Ser Trp Leu Cys Gln His Asp Arg Cys Glu Arg Tyr Gln Ala Ser
 65                  70                  75                  80

Asp Thr Thr Thr Leu Gln Ser Leu Gln Thr Cys Asn Met Leu Cys Ala
                 85                  90                  95

Ser Thr Gln Leu Trp Pro Gln Pro Thr Gly Pro Val Ser Leu Ala Ser
            100                 105                 110

Ala Ala Val Pro Val Arg Ser Asp Arg Phe Ser Leu Lys Val Ile Ala
        115                 120                 125

Ser Pro Ser Arg Asp Val Thr Lys His Leu Asn Glu Ala Phe Ile Val
    130                 135                 140

Met Gln Asn His Met Arg Thr Leu Glu His Gly Val Val Gly Glu Asn
145                 150                 155                 160

Arg Arg Ser Asp Ile Gly Pro Pro Arg Asp Val Leu Lys Val Ser
                165                 170                 175

Val Asn Gly Ser Gly Asp Pro Arg Met Arg Leu Asp Thr Asn Glu Ser
            180                 185                 190

Tyr Lys Leu Ala Leu Arg Pro Ser Gly Asn Ser Leu Val Val Asp Ile
        195                 200                 205

Thr Ala His Ser Phe Cys Gly Ala Arg His Gly Leu Glu Thr Leu Leu
    210                 215                 220
```

```
Gln Val Thr Trp Leu Asp Pro Tyr Ala Gly Ser Leu Leu Ile Leu Glu
225                 230                 235                 240

Ala Ala Thr Val Val Asp Ala Pro Arg Phe Pro Tyr Arg Gly Leu Leu
            245                 250                 255

Leu Asp Thr Ala Arg Asn Phe Phe Pro Val Ser Glu Leu Leu Arg Thr
        260                 265                 270

Ile Asp Ala Met Ala Ala Asn Lys Leu Asn Thr Phe His Trp His Val
    275                 280                 285

Ser Asp Ser Gln Ser Phe Pro Trp Lys Leu Asp Ser Ala Pro Gln Leu
290                 295                 300

Ala Gln His Gly Ala Tyr Gly Pro Gly Ala Val Tyr Thr Ser Asp Asp
305                 310                 315                 320

Val Arg Thr Ile Val Lys Tyr Ala Arg Ile Arg Gly Ile Arg Val Leu
            325                 330                 335

Met Glu Ile Asp Thr Pro Ala His Val Gly Arg Ala Phe Gly Trp Gly
            340                 345                 350

Pro Glu Ala Gly Leu Gly His Leu Ala His Cys Ile Glu Ala Glu Pro
        355                 360                 365

Trp Ser Ser Tyr Cys Gly Glu Pro Pro Cys Gly Gln Leu Asn Pro Arg
370                 375                 380

Asn Pro His Ile Tyr Asp Leu Leu Glu His Val Tyr Arg Glu Ile Ile
385                 390                 395                 400

Gln Leu Thr Gly Val Asp Asp Ile Phe His Leu Gly Gly Asp Glu Val
            405                 410                 415

Ser Glu Gln Cys Trp Ala Lys His Phe Asn Asp Thr Asp Pro Met Asp
            420                 425                 430

Leu Trp Met Glu Phe Thr Arg Gln Ala Met His Val Leu Glu Arg Ala
        435                 440                 445

Asn Gly Gly Lys Ala Pro Glu Leu Thr Leu Leu Trp Ser Ser Arg Leu
450                 455                 460

Thr Arg Ser Pro Tyr Leu Glu Arg Leu Asp Pro Lys Arg Phe Gly Val
465                 470                 475                 480

His Val Trp Gly Ala Ser Gln Trp Pro Glu Ser Arg Ala Val Leu Asp
            485                 490                 495

Ala Gly Phe Arg Ser Val Ile Ser His Val Asp Ala Trp Tyr Leu Asp
            500                 505                 510

Cys Gly Phe Gly Ser Trp Arg Asp Ser Ser Asp Gly His Cys Gly Pro
        515                 520                 525

Tyr Arg Ser Trp Gln Gln Val Tyr Glu His Arg Pro Trp Ala Thr Glu
530                 535                 540

Thr Pro Glu Ser Ala Ala Trp Pro Val Glu Gly Ala Ala Cys Gln
545                 550                 555                 560

Trp Thr Glu Gln Leu Gly Pro Gly Gly Leu Asp Ala Arg Val Trp Pro
            565                 570                 575

Arg Thr Ala Ala Leu Ala Glu Arg Leu Trp Ala Asp Arg Ala Glu Gly
            580                 585                 590

Ala Thr Ala Asp Val Tyr Leu Arg Leu Asp Thr Gln Arg Ala Arg Leu
        595                 600                 605

Val Ala Arg Gly Val Arg Ala Ala Pro Leu Trp Pro Arg Trp Cys Ser
        610                 615                 620

His Asn Pro His Ala Cys Leu
625                 630
```

<210> SEQ ID NO 9
<211> LENGTH: 500
<212> TYPE: DNA
<213> ORGANISM: Artificial Sequence
<220> FEATURE:
<223> OTHER INFORMATION: Synthetic Sequence

<400> SEQUENCE: 9

```
ccgaaggatt caagctccaa atagtgacgt caccttcccg cgacgtctcc gaccatctcg      60
ctgacgcctt cgaactgatg aaggaggaca tgcgcacgtt ggagcgcagc gctggctccg     120
agcgccgccc cgctgactac gggctgcctc gcaacgtgct cgtgcgcgtc gccatcaacg     180
gcagcgccga cccgcgcatg cgcctcgaca cagatgagag ttacaaactg accctgcggc     240
cctccaggaa gtctctcgtg ccgacatca ccgctcactc gttctgcggc gcgcggcacg      300
gtctcgagac tctctcgcaa attgtatgga tggacccta cgcgggttgc ttgctcatac     360
tagaggcagc tactgtagtc gacgcaccac ggttcccata tcgcggactt ctccttgaca     420
cagctcgaaa cttttcccg actggggaga tactacggac aatagacgcc atggctgcgt     480
ctaaaatgaa cacgttccac                                                500
```

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10

```
cgcagtcsar rtaccavgcr tcvac                                            25
```

<210> SEQ ID NO 11
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 15, 18
<223> OTHER INFORMATION: n = a, t, c, or g

<400> SEQUENCE: 11

```
tactgcgghg arccnccntg ygg                                              23
```

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12

```
cgacgaccac agtaacacta gctc                                             24
```

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13

```
aaagcacgtc gcgtgaactc tagc                                             24
```

```
<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
attgggtcgg tgtcgttgaa gtgc                                          24

<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15
gagtcgcaca gcatgttg                                                 18

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
caacgcatct acgctgagat tctcg                                         25

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
cggagctagt gttactgtg                                                19

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
cgtcatccgc ctagctatgt aacc                                          24

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
ggtgcgtaga taggcagtgc gatg                                          24

<210> SEQ ID NO 20
<211> LENGTH: 23
<212> TYPE: DNA
<213> ORGANISM: Artificial Sequence
<220> FEATURE:
```

<223> OTHER INFORMATION: Primer

<400> SEQUENCE: 20
cccgcacgtg tacgatctac tgc                                           23

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
cttgtaactc gagggcagtg g                                             21

<210> SEQ ID NO 22
<211> LENGTH: 26
<212> TYPE: DNA
<213> ORGANISM: Artificial Sequence
<220> FEATURE:
<223> OTHER INFORMATION: Primer

<400> SEQUENCE: 22
gtacgatcta ctgcaacgca tctacg                                        26

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
taggcagtgc gatgaagtgg tg                                            22

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
caccatgaag tggtggggcg ag                                            22

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
ctacaggcag gcgtgcgggt tg                                            22

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
caccatgtcc ttggctgtat cg                                            22

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
tcaaatgcat tcgcccgggat tc    22

<210> SEQ ID NO 28
<211> LENGTH: 23
<212> TYPE: DNA
<213> ORGANISM: Artificial Sequence
<220> FEATURE:
<223> OTHER INFORMATION: Primer

<400> SEQUENCE: 28
cccggggcgc cagcagagcg acg    23

<210> SEQ ID NO 29
<211> LENGTH: 18
<212> TYPE: DNA
<213> ORGANISM: Artificial Sequence
<220> FEATURE:
<223> OTHER INFORMATION: Primer

<400> SEQUENCE: 29
cccggggcgc cagcagag    18

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
gaattctcaa atgcattcgc cggga    25

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
cccgggagga gtcaccaagg ccc    23

<210> SEQ ID NO 32
<211> LENGTH: 28
<212> TYPE: DNA
<213> ORGANISM: Artificial Sequence
<220> FEATURE:
<223> OTHER INFORMATION: Primer

<400> SEQUENCE: 32
gaattcctaa aagtaattcc ctgttacg    28

<210> SEQ ID NO 33
<211> LENGTH: 27
<212> TYPE: DNA
<213> ORGANISM: Artificial Sequence
<220> FEATURE:
<223> OTHER INFORMATION: Primer

```
<400> SEQUENCE: 33
cccgggttta agtatcgtta atcctgg                                          27

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
acacctgcac gcctaggtga c                                                21

<210> SEQ ID NO 35
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 4, 10, 16, 19
<223> OTHER INFORMATION: n = a, t, c, or g

<400> SEQUENCE: 35
rytntggccn carccnacng g                                                21

<210> SEQ ID NO 36
<211> LENGTH: 23
<212> TYPE: DNA
<213> ORGANISM: Artificial Sequence
<220> FEATURE:
<223> OTHER INFORMATION: Primer

<400> SEQUENCE: 36
gtctagccgc tctaagtacg gtg                                              23

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
ttgacggagg tcgacgacct g                                                21

<210> SEQ ID NO 38
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 6, 15
<223> OTHER INFORMATION: n = a, t, c, or g

<400> SEQUENCE: 38
gcrtgnggrt trtgnswrca cc                                               22

<210> SEQ ID NO 39
<211> LENGTH: 22
<212> TYPE: DNA
<213> ORGANISM: Artificial Sequence
<220> FEATURE:
<223> OTHER INFORMATION: Primer
```

```
<400> SEQUENCE: 39
tgcgagatca cggtccggaa tc                                              22

<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
tccgacacat cacgagaagg agac                                            24

<210> SEQ ID NO 41
<211> LENGTH: 23
<212> TYPE: DNA
<213> ORGANISM: Artificial Sequence
<220> FEATURE:
<223> OTHER INFORMATION: Primer

<400> SEQUENCE: 41
gagacgtgac gatctgcagc ttg                                             23

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
gtgccagtgg acggagcagc tg                                              22

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
cgcggcggcc gacgtgtacc t                                               21

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
caccatgaag tggtggggcg acgca                                           25

<210> SEQ ID NO 45
<211> LENGTH: 22
<212> TYPE: DNA
<213> ORGANISM: Artificial Sequence
<220> FEATURE:
<223> OTHER INFORMATION: Primer

<400> SEQUENCE: 45
ctagaggcag gcgtgcgggt tg                                              22

<210> SEQ ID NO 46
```

```
<211> LENGTH: 22
<212> TYPE: DNA
<213> ORGANISM: Artificial Sequence
<220> FEATURE:
<223> OTHER INFORMATION: Primer

<400> SEQUENCE: 46
acgtcgtcgg acgtgtacac tg                                               22

<210> SEQ ID NO 47
<211> LENGTH: 21
<212> TYPE: DNA
<213> ORGANISM: Artificial Sequence
<220> FEATURE:
<223> OTHER INFORMATION: Primer

<400> SEQUENCE: 47
tgtggccaga gctgggtgga g                                                21

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
gaggcgcaca gcatgttgca agtc                                             24

<210> SEQ ID NO 49
<211> LENGTH: 23
<212> TYPE: DNA
<213> ORGANISM: Artificial Sequence
<220> FEATURE:
<223> OTHER INFORMATION: Primer

<400> SEQUENCE: 49
gatgtgtact tgcggctcga cac                                              23

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
gtacttgcgg ctcgacacac agc                                              23

<210> SEQ ID NO 51
<211> LENGTH: 23
<212> TYPE: DNA
<213> ORGANISM: Artificial Sequence
<220> FEATURE:
<223> OTHER INFORMATION: Primer

<400> SEQUENCE: 51
caccatgatg tcgtggggtg atg                                              23

<210> SEQ ID NO 52
<211> LENGTH: 19
<212> TYPE: DNA
<213> ORGANISM: Artificial Sequence
<220> FEATURE:
<223> OTHER INFORMATION: Primer

<400> SEQUENCE: 52
```

```
actagaggca cgcgtgcgg                                                    19

<210> SEQ ID NO 53
<211> LENGTH: 23
<212> TYPE: DNA
<213> ORGANISM: Artificial Sequence
<220> FEATURE:
<223> OTHER INFORMATION: Primer

<400> SEQUENCE: 53
cgactggagc acgaggacac tga                                               23

<210> SEQ ID NO 54
<211> LENGTH: 26
<212> TYPE: DNA
<213> ORGANISM: Artificial Sequence
<220> FEATURE:
<223> OTHER INFORMATION: Primer

<400> SEQUENCE: 54
ggacactgac atggactgaa ggagta                                            26

<210> SEQ ID NO 55
<211> LENGTH: 25
<212> TYPE: DNA
<213> ORGANISM: Artificial Sequence
<220> FEATURE:
<223> OTHER INFORMATION: Primer

<400> SEQUENCE: 55
gctgtcaacg atacgctacg taacg                                             25

<210> SEQ ID NO 56
<211> LENGTH: 23
<212> TYPE: DNA
<213> ORGANISM: Artificial Sequence
<220> FEATURE:
<223> OTHER INFORMATION: Primer

<400> SEQUENCE: 56
cgctacgtaa cggcatgaca gtg                                               23
```

LEPIDOPTERAN INSECT N-ACETYLGLUCOSAMINIDASE GENES AND THEIR USE IN GLYCOENGINEERING

CROSS-REFERENCE TO RELATED APPLICATIONS

The present application claims the benefit of U.S. Provisional Patent Application No. 61/013,815, filed Dec. 14, 2007, the entire disclosure of which is incorporated by reference herein.

STATEMENT REGARDING FEDERAL SPONSORED RESEARCH OR DEVELOPMENT

Pursuant to 35 U.S.C. §202(c), it is acknowledged that the U.S. Government has certain rights in the invention described, which was made in part with funds from NIH grant number, GM49734.

FIELD OF THE INVENTION

This invention relates to the fields of molecular biology and production of proteins possessing complex type oligosaccharide side chains. More specifically, the invention provides novel nucleic acid sequences encoding β-N-acetylglucosaminidase enzymes and recombinant insect cell lines comprising the same for the production of therapeutic and commercially valuable glycoproteins.

BACKGROUND OF THE INVENTION

Several publications and patent documents are cited throughout the specification in order to describe the state of the art to which this invention pertains. Each of these citations is incorporated herein by reference as though set forth in full.

Insects and other lower eukaryotes, such as nematodes and plants, occupy an interesting evolutionary niche in glycobiology because they produce N-glycoproteins, but they typically process their N-linked glycans less extensively than mammals (1,2). This difference between lower and higher eukaryotic protein N-glycosylation pathways is biotechnologically significant because insects and plants are used to produce recombinant mammalian glycoproteins for many different biomedical research applications (3-7). Insect and mammalian protein N-glycosylation pathways each begin with the co-translational transfer of N-glycan precursors to nascent proteins (1,8). These precursors are subsequently trimmed and elongated by enzymes localized in the endoplasmic reticulum and Golgi apparatus of insect and mammalian cells to produce a common intermediate with the structure Manα6(GlcNAcβ2Manα3)Manβ4 GlcNAcβ4GlcNAc-R. In mammalian cells, this intermediate is elongated by various glycosyltransferases to produce complex N-glycans, which often have terminal sialic acid residues. In contrast, insect cells usually fail to elongate this same intermediate and convert it, instead, to paucimannose N-glycans with the core structure Manα6(Manα3)Manβ4GlcNAcβ4GlcNAc-R. An unusual β-N-acetylglucosaminidase is responsible for the production of these structures (9). This enzyme specifically removes the terminal N-acetylglucosamine residue from the α3 branch of Manα6 (GlcNAcβ2Manα3)Manβ4GlcNAcβ4GlcNAc-R, simultaneously eliminating the intermediate required for N-glycan elongation and producing the core paucimannose glycan typically found on insect cell-derived N-glycoproteins. This same enzyme is also responsible for the production of core paucimannose N-glycans in nematodes (10,11) and plants (12,13). Thus, the presence of a processing β-N-acetylglucosaminidase is a key difference between the protein N-glycosylation pathways of lower and higher eukaryotes.

In the seminal insect study on this topic, Altmann and coworkers (9) demonstrated that IPLB-Sf21AE, a cell line derived from the lepidopteran insect *S. frugiperda* (14), has a membrane-associated β-N-acetylglucosaminidase activity that can specifically cleave the terminal N-acetylglucosamine residue from the α3 branch of a biantennary N-glycan in vitro. Subsequently, it was shown that cell lines derived from *E. acrea*, another lepidopteran insect, produced hybrid and complex N-glycans containing terminal N-acetylglucosamine or galactose residues because they lack this intracellular β-N-acetylglucosaminidase activity (15). Together, these studies strongly supported the idea that the N-glycosylation pathway of at least some insect cells includes a processing β-N-acetylglucosaminidase, as described above. However, unequivocal proof of this concept awaited the isolation of an insect gene encoding this enzyme, together with evidence that the gene product had the substrate specificity of the N-glycan processing enzyme.

The first proof of this kind was provided by a more recent study from Altmann's group, in which they demonstrated that the *D. melanogaster* fused lobes (Dm-fdl) gene encodes the specific, processing β-N-acetylglucosaminidase in this organism (16). Importantly, this study demonstrated that the Dm-fdl gene product has several features distinguishing it from degradative hexosaminidases and chitinases, which also have β-N-acetylglucosaminidase activities. These features included its specificity for the terminal N-acetylglucosamine residue linked to the α3 branch of N-glycan substrates and its inability to degrade chito-oligosaccharides. Furthermore, it was shown that flies lacking a functional fdl gene produced a higher proportion of N-glycans with terminal N-acetylglucosamine residues linked to the α3 branch than wild type. These findings, together with the finding that the *D. melanogaster* hexosaminidase genes (hexo1 and hexo-2) encode enzymes that can cleave chito-oligosaccharides, but not N-glycans, strongly suggested that Dm-FDL is the β-N-acetylglucosaminidase responsible for N-glycan processing in this fly. These properties also were consistent with the idea that Dm-FDL is an ortholog of the lepidopteran insect N-glycan processing enzyme first detected by Altmann and coworkers (1995) in microsomal membranes from IPLB-Sf21AE cells.

Subsequently, two lab groups independently reported molecular cloning of genes encoding β-N-acetylglucosaminidases from Sf9 cells, which are a clonal derivative of the IPLB-Sf21AE cell line (17,18). Our group described the isolation of three β-N-acetylglucosaminidase genes from Sf9 cells, which were designated SfGlcNAcase-1, -2, and -3 (18). SfGlcNAcase-1 was clearly distinct from the other two, which were nearly identical to each other and appeared to be allelic variants of the same gene. Further analysis of the SfGlcNAcase-1 and SfGlcNAcase-3 gene products showed that they had high sequence homology to known hexosaminidases and that each also had β-N-acetylglucosaminidase activity when assayed against relevant substrates. However, neither had the tight α3 branch specificity of the processing enzyme activity originally described by Altmann and coworkers (1995). In fact, each could remove the terminal N-acetylglucosamine residues from either the α3 or the α6 branch of various N-glycan substrates and each also was able to release N-acetylglucosamine monomers from a chito-oligosaccharide substrate. Accordingly, we concluded that none of these *S. frugiperda* genes encoded the N-glycan processing enzyme, but rather, that they encoded broad-spectrum β-N-acetylglucosaminidases that are more likely to be involved in N-glycan and chitin degradation. In a similar study, Tomiya and coworkers (2006) also molecularly cloned two allelic variants of an Sf9 cell β-N-acetylglucosaminidase gene, which they termed Sfhex. Further analysis of the Sfhex gene product, which is identical to the gene product we designated SfGlcNAcase-3, confirmed that the SfGlcNAcase-3/Sfhex gene product lacks the α3 branch specificity of the processing enzyme activity originally described by Altmann and coworkers. However, because this enzyme had a 2- to 5-fold higher preference for the terminal N-acetylglucosamine residue on the α3 branch of an N-glycan substrate, Tomiya and coworkers (2006) concluded that the SfGlcNAcase-3/Sfhex gene encodes the processing β-N-acetylglucosaminidase of Sf9 cells.

SUMMARY OF THE INVENTION

In accordance with the present invention, an isolated nucleic acid encoding an N-acetylglucosaminidase is provided. In one embodiment the nucleic acid encodes a protein of SEQ ID NO: 2. In a preferred embodiment, nucleic acid is SEQ ID NO: 1. The nucleic acid molecules of the invention may be DNA, RNA, or cDNA and they may be single or double stranded. Additional embodiments of the invention include nucleic acids of SEQ ID NOS: 3, 5, and 7 and their encoded proteins SEQ ID NOS: 4, 6, and 8.

In another aspect, expression vectors comprising the nucleic acid molecules described above are provided. Also within the scope of the invention are recombinant insect cells transformed with such expression vectors.

In a particularly preferred embodiment, there is provided a double-stranded RNA molecule that hybridizes to a fragment of SEQ ID NO: 1, the fragment having SEQ ID NO: 9. The RNA molecule functions to down regulate production of the protein of SEQ ID NO: 2.

In still another aspect, the present invention provides isolated proteins comprising SEQ ID: 2, 4, 6 and 8. The isolated proteins of this invention may be used for the production of specific glycans for use as standards, or substrates, e.g., in remodeling recombinant glycoprotein glycans.

In yet another aspect, a method for enhancing production of mammalian-like N-glycans in insect cells is provided. An exemplary method entails providing recombinant insect cell lines comprising the double stranded RNA molecule described above, either transforming the cells with an expression vector or infecting the cells with a recombinant baculovirus comprising a nucleic acid encoding a heterologous glycoprotein of interest, wherein glycoprotein(s) expressed in the recombinant comprise elevated levels of mammalian-like N-glycans when compared to levels observed in wild type cells. In an alternative embodiment, the cells described above may optionally contain additional enzymes involved in the production and synthesis of mammalian-like N glycans. Such enzymes include, without limitation, N-acetylglucosaminyl-transferases, galactosyltransferases, sialyltransferases, sulfotransferases, sialic acid synthases, CPM-sialic acid synthetases, UDP-N-acetylglucosamine-2-epimerases/N-acetylmannosamine kinases, and CMP-sialic acid transporters.

Presented hereinbelow are data that will resolve the apparent discrepancy in the conclusions drawn from the two previous reports referred to above (17,18). In short, the present inventors molecularly cloned a β-N-acetylglucosaminidase cDNA from Sf9 cells, which turned out to be the *S. frugiperda* ortholog of the Dm-fdl gene. This gene, designated Sf-fdl, encodes a membrane-associated product that specifically cleaves the terminal N-acetylglucosamine residue from the α3 branch of N-glycan substrates, that has little or no activity against chito-oligosaccharide substrates, and that has precisely the same pH profile as the activity originally identified by Altmann and coworkers (1995) in IPLB-Sf21AE cell microsomes. Furthermore, Sf9 cells engineered to express a Sf-fdl-specific double-stranded RNA had lower levels of specific, processing β-N-acetylglucosaminidase activity. These results indicate that the specific, processing β-N-acetylglucosaminidase activity originally detected by Altmann and coworkers is encoded by the Sf-fdl gene in this lepidopteran insect cell line. The definitive identification of this new gene sets the stage for an effort to create a transformed Sf9 cell variant lacking this key N-glycan processing activity, which would be an improved host for recombinant glycoprotein production by baculovirus expression vectors.

BRIEF DESCRIPTION OF THE DRAWINGS

FIG. 1. Nucleotide sequence of the Sf-fdl gene (SEQ ID NO: 1) and amino acid sequence of the gene product (SEQ ID NO: 2). The putative N-terminal transmembrane domain is underlined and the two consensus N-glycosylation sites are boxed.

FIG. 8. Nucleotide sequence of the Tn-fdl gene (SEQ ID NO:3) and amino acid sequence of the gene product (SEQ ID NO:4). The putative N-terminal transmembrane domain is underlined and the two consensus N-glycosylation sites are boxed.

FIG. 9. Nucleotide sequence of one allele the Bm-fdl gene (SEQ ID NO:5) and amino acid sequence of the gene product (SEQ ID NO:6). The putative N-terminal transmembrane domain is underlined and the three consensus N-glycosylation sites are boxed.

FIG. 10. Nucleotide sequence of another allele of Bm-fdl gene (SEQ ID NO:7) and amino acid sequence of the gene product (SEQ ID NO:8). The putative N-terminal transmembrane domain is underlined and the three consensus N-glycosylation sites are boxed.

FIG. 12. The sequence utilized in the RNAi experiment is shown (SEQ ID NO:9).

DETAILED DESCRIPTION OF THE INVENTION

Figure 2:
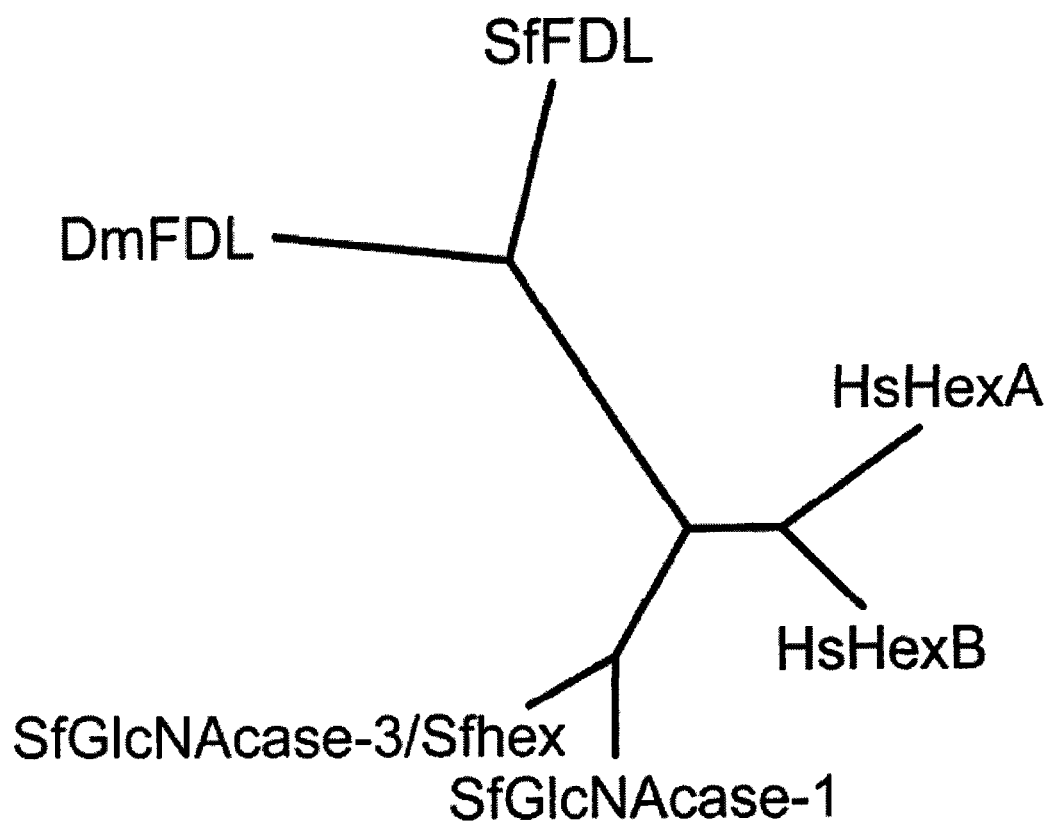
FIG. 2. Phylogenetic relationships between the Sf-FDL protein and known hexosaminidases. This Figure shows the phylogenetic relationships between the Sf-FDL protein and Dm-FDL (Acc No. NM_165909; 16), SfGlcNAcase-3/Sf-Hex (Acc No. DQ249309; 17,18)), SfGlcNAcase-1 (DQ249307; 18), and the human hexosaminidases A (Acc. No. NM_000520; 33) and B (NM_000521; 34. The amino acid sequences of these proteins were aligned using CLUSTALX version 1.83 (21) using the default settings and then the alignment was exported in the PHYLIP format (36) and used to generate a distance matrix by protdist in PHYLIP version 3.66 with the Jones-Taylor-Thornton model. Neighbor in PHYLIP version 3.66 was used to generate an unrooted tree from the distance matrix with the neighbor-joining method and, finally, the Neighbor output was used to draw an unrooted tree with the PHYLIP postscript generator. The Sf-FDL amino acid sequence is 44% and 29% identical to the sequences of Dm-FDL and SfGlcNAcase-3/S fHex, respectively.

Manα6(Manα3)Manβ4GlcNAcβ4GlcNAc-R is the core structure of the major processed protein N-glycans produced by insect cells. Ultimately, this paucimannose type structure is produced by an unusual β-N-acetylglucosaminidase, which removes the terminal N-acetylglucosamine residue from the upstream intermediate, Manα6(GlcNAcβ2Manα3)Manβ4GlcNAcβ4GlcNAc-R. Because the N-glycan processing pathways leading to the production of this intermediate are probably identical in insects and higher eukaryotes, the presence or absence of this specific, processing β-N-acetylglucosaminidase is a key factor distinguishing the processing pathways in these two different types of organisms. Recent studies have shown that the fused lobes (fdl) gene encodes the specific, processing β-N-acetylglucosaminidase of *D. melanogaster*. However, there are conflicting reports on the identity of the gene encoding this enzyme in the lepidopteran insect, *S. frugiperda*. One has suggested that a gene alternatively designated SfGlcNAcase-3 or SfHex encodes this function, while another has suggested that this gene encodes a broad-spectrum β-N-acetylglucosaminidase that functions in glycan and chitin degradation. In the present invention, this conflict is resolved by demonstrating that an *S. frugiperda* fdl ortholog (Sf-fdl) encodes a product with the substrate specificity expected of a processing β-N-acetylglucosaminidase. It is also shown that the endogenous levels of specific, processing β-N-acetylglucosaminidase activity are significantly reduced in *S. frugiperda* cells engineered to express a double-stranded RNA derived from the Sf-fdl gene. These results indicate that Sf-fdl encodes the specific, processing β-N-acetylglucosaminidase of *S. frugiperda*.

Definitions

A "cell line" refers to cells which can be cultured in the lab for an indefinite period and are useful for producing large amounts of a protein of interest. Ideally, such cells are immortalized and do not exhibit senescence in culture.

As used herein, the term "insect" includes any stage of development of an insect, including a one-celled germ line cell, a fertilized egg, an early embryo, a larva, including any of a first through final instar larva, a pupa, or an adult insect. For the production of mammalianized glycoproteins of interest, a large larva, such as a fourth or fifth instar larva is preferred. It will be evident to a skilled worker which insect stage is suitable for a particular purpose, such as for direct production of a glycosylated polypeptide of interest, for storage or transport of an insect to a different location, for generation of progeny, for further genetic crosses, or the like.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "promoter region" refers to the transcriptional regulatory regions of a gene, which may be found at the 5' or 3' side of the coding region, or within the coding region, or within introns.

The term "vector" refers to a small carrier DNA molecule into which a DNA sequence can be inserted for introduction into a host cell where it will be replicated. An "expression vector" is a specialized vector that contains a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, of the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide sequence or amino acid sequence means a sequence having the properties of a given SEQ ID NO:. For example, when used in reference to an amino acid sequence, the phrase includes the sequence per se and molecular modifications that would not affect the basic and novel characteristics of the sequence.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application for which the oligonucleotide is used.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides.

The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to act functionally as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product.

The primer may vary in length depending on the particular conditions and requirements of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "percent identical" is used herein with reference to comparisons among nucleic acid or amino acid sequences. Nucleic acid and amino acid sequences are often compared using computer programs that align sequences of nucleic or amino acids thus defining the differences between the two. For purposes of this invention comparisons of nucleic acid sequences are performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (at http://www.ncbi.nlm.nih.gov/blast/; Altschul et al., 1990, J Mol Biol 215:403-410) using a gapped alignment with default parameters, may be used to determine the level of identity and similarity between nucleic acid sequences and amino acid sequences.

The term "expression control sequence", as used herein, refers to a polynucleotide sequence that regulates expression of a polypeptide coded for by a polynucleotide to which it is functionally ("operably") linked. Expression can be regulated at the level of the mRNA or polypeptide. Thus, the term expression control sequence includes mRNA-related elements and protein-related elements. Such elements include promoters, domains within promoters, upstream elements, enhancers, elements that confer tissue or cell specificity, response elements, ribosome binding sequences, transcriptional terminators, etc.

Suitable expression control sequences that can function in insect cells will be evident to the skilled worker. In some embodiments, it is desirable that the expression control sequence comprises a constitutive promoter. Among the many suitable "strong" promoters which can be used are the baculovirus promoters for the p10, polyhedrin (polh), p6.9, capsid, and cathepsin-like genes. Among the many "weak" promoters which are suitable are the baculovirus promoters for the ie1, ie2, ie0, et1, 39K (aka pp31), and gp64 genes. Other suitable strong constitutive promoters include the *B. mori* actin gene promoter; *D. melanogaster* hsp70, actin, α-1-tubulin or ubiquitin gene promoters; RSV or MMTV promoters; copia promoter; gypsy promoter; and the cytomegalovirus IE gene promoter. If it is desired to increase the amount of gene expression from a weak promoter, enhancer elements, such as the baculovirus enhancer element, hr5, may be used in conjunction with the promoter.

In some embodiments, the expression control sequence comprises a tissue- or organ-specific promoter. Many such expression control sequences will be evident to the skilled worker.

In general, the enzymes involved in N-glycan processing of the invention are required in catalytic amounts. Therefore, in one embodiment of the invention, much lower amounts of these enzymes are present than of the heterologous polypeptides of interest, which are generated in massive, large amounts, glycosylated, and harvested for further use. For example, a suitable molar ratio of heterologous protein produced to enzyme involved in N-glycan processing may be greater than about 100:1.

Alternatively, the enzymes involved in N-glycan processing may be in comparable (e. g., approximately stoichiometric) amounts to the heterologous glycoprotein to be processed. A skilled worker can readily select suitable promoters and/or conditions to express suitable amounts of the enzymes involved in N-glycan processing (e.g., amounts which are sufficient to (effective to) process the N-glycans of relatively high amounts of a protein of interest to the desired extent). Furthermore, a skilled worker can readily ensure that the enzymes involved in N-glycan processing are present in sufficient local concentrations, and at an optimal time during insect propagation.

In some embodiments of the invention, as is discussed in more detail elsewhere herein, it is desirable that an expression control sequence is regulatable (e. g., comprises an inducible promoter and/or enhancer element). Suitable regulatable promoters include, e.g., *Drosophila* or other hsp70 promoters, the *Drosophila* metallothionein promoter, an ecdysone-regulated promoter, the *Saccharomyces cerevisiae* Gal4/UAS system, and other well-known inducible systems. A Tet-regulatable molecular switch may be used in conjunction with any constitutive promoter, such as those described elsewhere herein (e. g, in conjunction with the CMV-IE promoter, or baculovirus promoters). Another type of inducible promoter is a baculovirus late or very late promoter that is only activated following infection by a baculovirus.

Methods for designing and preparing constructs suitable for generating transgenic insect cell lines or insects (or vectors for infection of an insect) are conventional. For these methods, as well as other molecular biology procedures related to the invention, see, e. g., Sambrook et al., Molecular Cloning: A Laboratory Manual, Second Edition, Cold Spring Harbor, N.Y., (1989); Wu et al., Methods in Gene Biotechnology (CRC Press, New York, N.Y., 1997), Recombinant Gene Expression Protocols, in Methods in Molecular Biology, Vol. 62, (Tuan, Ed., Humana Press, Totowa, N.J., 1997); and Current Protocols in Molecular Biology, (Ausabel et al., Eds.,), John Wiley & Sons, NY (1994-1999). Some suitable methods are described elsewhere herein.

A variety of immortalized lepidopteran insect cell lines are suitable for transformation by the vectors/constructs of the invention. Among these are Sf9 (Vaughn et al. (1977) In Vitro 13, 213-217), Tn 5B1-4 (High Five; Wickham et al. (1992) Biotech. Progr. 8, 391-6), expresSf+ (Protein Sciences Corporation), and BmN (Bm-N4; Maeda et al. (1985) Nature 315, 592-594) cells.

Methods for generating transgenic insect cell lines are conventional. For example, in one embodiment, one or more genes to be introduced are placed under the control of a suitable expression control sequence and are cloned into one or more plasmid vectors. These vectors are then mixed with a vector encoding a selectable marker under the control of a suitably expression control sequence. The DNA mixture is then introduced into the parental insect cell line (e.g., by calcium phosphate-mediated transfection), and the transgene(s) will integrate by non-homologous recombination into in the insect cell genome. Transformed cells are selected using an appropriate antibiotic (e.g. neomycin, hygromycin, or zeocin, among others), cloned by colony formation or limiting dilution, and clones expressing the unselected genes of interest are identified using various methods, including RNA dot blot assays, lectin staining assays, or functional assays. This general approach was first described in 1990 (Jarvis et al., 1990. Bio/Technology 8,950-955) and has been reviewed recently (Harrison, R. L. and Jarvis, D. L. 2007. Transforming lepidopteran insect cells for improved protein processing. In D. W. Murhammer (Ed.), Methods in Molecular Biology: Baculovirus Expression Protocols. Humana Press, Clifton, N.J. Methods Mol Biol. (2007) 388: 3-22.

Methods for generating transgenic insects are conventional. For example, in one embodiment, one or more genes to be introduced are placed under the control of a suitable expression control sequence, and are cloned into a vector, such as a viral vector (e. g, an attenuated baculovirus vector, or a non-permissive viral vector that is not infective for the particular insect of interest). The sequences to be introduced into the insect are flanked by genomic sequences from the insect. The construct is then introduced into an insect egg (e.g., by microinjection), and the transgene (s) then integrate by homologous recombination of the flanking sequences into comparable sequences in the insect genome.

In another embodiment, the vector is a transposon-based vector. One form of such transposon-based vectors is a viral vector (such as those described above) that further comprises inverted terminal repeats of a suitable transposon, between which the transgene of interest is cloned. One or more genes of interest, under the control of a suitable expression control sequence (s), are cloned into the transposon-based vector. In some systems, the transposon-based vector carries its own transposase. However, generally, the transposon-based vector does not encode a suitable transposase. In this case, the vector is co-transfected into an insect (e. g., an insect larva) with a helper virus or plasmid that provides a transposase. The recombinant vector (along with, generally, a helper) is introduced by conventional methods (such as microinjection) into an egg or early embryo; and the transgene (s) become integrated at a transposon site (such as sequences corresponding to the inverted terminal repeat of the transposon) in the insect genome.

Suitable types of transposon-based vectors will be evident to the skilled worker. These include, e. g., Minos, mariner, Hermes, sleeping beauty, and piggyBac.

In a preferred embodiment, the vector is a piggyBac vector. TTAA-specific, short repeat elements feature in a group of transposons (Class II mobile elements) that have similar structures and movement properties. A typical piggyBac vector (formerly IFP2) is the most extensively studied of these insertion elements. piggyBac is 2.4 kb long and terminates in 13 bp perfect inverted repeats, with additional internal 19 bp inverted repeats located asymmetrically with respect to the ends (Cary et al. (1989) Virology. 172, 156-69). A piggyBac vector may encode a trans-acting transposase that facilitates its own movement; alternatively, these sequences can be deleted and this function can be supplied by a helper plasmid or virus. Non-essential genes have been deleted from piggyBac, allowing for the cloning of inserts as large as about 15 kB into certain piggyBac vectors. This allows, for example, for the insertion of about six or seven genes with their expression control sequences. Thus, a collection of enzymes involved in N-glycan processing, marker proteins, or the like, can be introduced together via a single transposon vector, into a single site in an insect genome.

Several piggyBac vectors have been developed for insect transgenesis. Two particularly useful constructs, defined as minimal constructs for the movement of piggyBac vectored sequences, were developed by analysis of deletion mutations both within and outside of the boundaries of the transposon (Li et al. (2001) Mol. Genet. Genomics. 266, 190-8). Using constructs such as these it is possible to increase the amount of genetic material mobilized by the piggybac transposase by minimizing the size of the vector. The minimal requirements for movement include the 5' and 3'terminal repeat domains and attendant TTAA target sequences.

Nearly all of the internal domain may be removed, although more recent data indicate that some of this region may be required for efficient translocation of the mobilized sequences into the genome of the insect. In addition, a minimum of 50 bases separating the TTAA target sites of the element is required for efficient mobilization (Li et al. (2001), supra). piggyBac can transpose in insect cells while carrying a marker gene, and movement of the piggyBac element can occur in cells from lepidopteran species distantly related to the species from which it was originally isolated. piggyBac has been shown to be capable of transforming *Drosophila melanogaster, Anastrepha suspensa, Bactrocera dorsalis, Bombyx mori, Pectinophora gossypiella, Tribolium castaneum*, and several mosquito species. At least three lepidopteran species, *Pectinophora gossypiella, Trichoplusia ni* and *Bombyx mori*, have been successfully transformed by the piggyBac element.

Generally, a helper virus or plasmid that expresses a transposase is co-introduced with the transposon-based vector as above. Expression of the transposase is determined by the choice of promoter for the insect system being tested. Toward that end, several promoter-driven helper constructs that are useful for lepidopteran transformation, including the *Drosophila* hsp70, baculovirus ie1 promoter, and *Drosophila* Actin 5C promoter, have been constructed.

For further guidance on the use of baculovirus-based vectors, see, e. g., WO01/29204 and U.S. Pat. No. 6,551,825. Other recent references that discuss piggyBac vectors and methods for generating transgenic insects using them include, e. g, Handler et al. (1998) Proc Natl Acad Sci 95,7520-7525; Fraser, M J (2001) The TTAA-specific family of transposable elements. In: Insect transgenesis: Methods and Applications. James A A and. Handler A H, Eds. CRC Press, Orlando, Fla.; Lobo et al. (1999) Mol. Gen. Genetics 261, 803-810; Grossman et al. (2000) Insect Biochem. Mol. Biol. 30,909-914; Lobo et al. (2001) Mol Gen. Genom. 265, 66-71; Lorenzen et al. (2003) Insect Mol Biol. 12, 433-40; Hacker et al. (2003) Proc Natl Acad Sci USA. 100, 7720-5; Sumitani et al. (2003) Insect Biochem Mol Biol. 33,449-58; Horn et al. (2003) Genetics 163 647-61; and Tomita et al. (2003) Nat Biotechnol. 21,52-6.

Methods for introducing constructs into an embryo to generate a transgenic insect (e. g., by microinjection) are conventional. Survivorship is usually quite high (up to 75%) for microinjected embryos. In general, preblastoderm eggs are stuck with a fine glass capillary holding a solution of the plasmid DNA and/or the recombinant virus. GO larvae hatched from the virus-injected eggs are then screened for expression of the gene of interest. Breeding transgenic G1s with normal insects yields transgenic offspring according to the rules of Mendelian inheritance.

Once a transgene (s) is stably integrated into the genome of an insect egg or early embryo, conventional methods can be used to generate a transgenic insect, in which the transgene (s) is present in all of the insect somatic and germ cells. When a subset of the complete set of enzymes involved in N-glycan processing are present in a transgenic insect, other transposon-based vectors, which express different subsets of the genes encoding enzymes involved in N-glycan processing, can be introduced sequentially into the insect genome, and transgenic insects can then be generated. In another embodiment, when different subsets of the complete set of enzymes involved in N-glycan processing are present in two or more individual transgenic insects, these insects can be genetically crossed to produce a transgenic insect that expresses a larger subset, or a complete set, of the genes encoding enzymes involved in N-glycan processing.

In some embodiments, the transgenic insects are heterozygous for the modifying enzyme genes. For example, when potentially toxic genes are expressed constitutively, it may be advantageous for the insects to be heterozygous, to limit the amount of the enzyme that is produced. In other embodiments, the insects are homozygous for the transgenes. Methods for producing homozygous transgenic insects (e. g., using suitable back-crosses) are conventional.

Another embodiment of the invention is an isolated cell, or progeny thereof, derived from a transgenic insect of the invention. Suitable cells include isolated germ line cells, and cells that can be used for the in vitro production of a glycoprotein exhibiting a partial or complete pattern of mammalian glycosylation. Methods for obtaining and propagating cells from a transgenic insect, and using them (e. g. to generate more insects, or to generate glycosylated proteins) are conventional.

The transgenic insects discussed above can be used to produce glycoproteins of interest that exhibit partial or complete patterns of mammalian glycosylation. For example, the insects can be used in methods for glycosylating polypeptides in a mammalian (human) glycosylation pattern.

The coding sequences described herein may be operably linked to an expression control sequence from the virus, itself, or to another suitable expression control sequence. Suitable virus-based vectors include, e g., baculovirus vectors (such as vectors based on *Autographa californica* NPV, *Orgyia pseudotsugata* NPV, *Lymantria dispar* NPV, *Bombyx mori* NPV, *Trichoplusia ni* NPV, *Spodoptera exigua* NPV, *Heliothis zea* NPV, *Galleria mellonella* NPV, *Anagrapha falcifera* NPV, *Trichoplusia ni* sNPV)); retroviral vectors; and viral vectors that comprise transposon recognition sequences (e g., piggyBac vectors); etc. As discussed above, baculovirus-based vectors have been generated (or can be generated without undue experimentation) that allow the cloning of large numbers of inserts, at any of a variety of cloning sites in the viral vector. Thus, more than one heterologous polypeptide may be introduced together into a transgenic insect cell or insect of the invention. The viral vector can be introduced into an insect cell or insect by conventional methods, such as by in vitro inoculation (insect cells) or oral ingestion (insect larvae).

In one embodiment, the baculovirus replicates until the host insect is killed. The insect cell or insect lives long enough to produce large amounts of the glycosylated polypeptide of interest. In another embodiment, a baculovirus is used that is attenuated or non-permissive for the host. In this case, the host is not killed by replication of the baculovirus, itself (although the host may be damaged by the expression of the enzymes involved in N-glycan processing and/or the heterologous protein of interest).

In another embodiment, sequences encoding one or more recombinant proteins of interest, operably linked to an expression control sequence, are cloned into a suitable transposon-based vector (such as a piggyBac vector). Like the baculovirus vectors discussed above, transposon-based vectors can carry large inserts, so more than one heterologous polypeptide may be introduced together into a transgenic insect of the invention. Transposon-based vectors may on occasion insert into the DNA of somatic cells, and thus be stably expressed for relatively long periods of time.

In another embodiment, sequences encoding one or more recombinant proteins of interest, operably linked to an expression control sequence, are cloned into a retrovirus vector, or any other suitable virus vector. Such a construct may insert into the DNA of somatic cells, and thus be stably expressed for relatively long periods of time.

Finally, in certain instances it may be desirable to down regulate expression and synthesis of the N-acetylglucosaminidase encoded by genes described in this invention. Accordingly, the invention also provides short double-stranded RNA sequences which hybridize to SEQ ID NO: 1 and function to downregulate the expression of the same in insect cells by an RNAi-dependant mechanism The following materials and methods are provided to facilitate the practice of the present invention.

Cells and Cell Culture

Sf9 cells, which are a subclone of the IPLB-Sf21-AE cell line derived from S. frugiperda ovaries (14), were routinely maintained as shake flask cultures in either TNM-FH medium containing 10% fetal bovine serum (HyClone, Logan, Utah) or ESF 921 serum-free medium (Expression Systems, CA), as described previously (18).

Molecular Cloning of an Fdl Gene Homolog from Sf9 Cells

The A. aegypti, A. gambiae, A. mellifera, B. mori, D. pseudoobscura and T. castaneum genomic databases were searched through the NCBI website using tBLASTn (19) with the derived amino acid sequence of Dm-FDL isoform C (Accession No. NM_165909) as the query. These searches identified exons from each species that encoded fragments of putative processing β-N-acetylglucosaminidases. These were joined in silico using an online splice site prediction algorithm available through the NetGene2 Server hosted by the Technical University of Denmark (20) to obtain contiguous open reading frames from each species. The predicted amino acid sequences were then aligned using CLUSTALX version 1.83 (21) with the default settings. Highly conserved amino acid sequences were visually identified and used to design degenerate oligonucleotide primers (Table 1), which were then used for polymerase chain reactions (PCRs; 22) with both cDNA and genomic DNA prepared from Sf9 cells as the templates. Genomic DNA was isolated from log phase cultures of uninfected Sf9 cells by a standard method (23). Total RNA was isolated from a log phase culture of uninfected Sf9 cells using the TriReagent (Molecular Research Center, Cincinnati, Ohio) according to the manufacturer's protocol. cDNA was prepared from 5 μg of GeneRacer™ oligo-dT-primed total RNA using SuperScript™ III reverse transcriptase with the commercial GeneRacer™ kit (Invitrogen, Carlsbad, Calif.) according to the manufacturer's protocol and diluted to a final volume of 50 μL. The PCRs were performed in a total volume of 50 μL containing the manufacturer's high fidelity (HF) buffer plus 0.2 mM of each dNTP, 2 U of Phusion™ DNA polymerase (Promega, Madison, Wis.), 1 μM of each degenerate primer, and either ~100 ng of Sf9 genomic DNA or 2 μL of the cDNA preparation described above. The reactions were incubated for 2 min at 98° C., then cycled 14 times using (i) 20 sec at 98° C., (ii) 20 sec at 76 to 62° C. (with a decreasing temperature gradient of 1° C. per cycle), and (iii) 30 sec at 72° C. The reactions were cycled another 30 times using (i) 20 sec at 98° C., (ii) 20 sec at 62° C., and (iii) 20 sec at 72° C., and finally incubated for 5 min at 72° C. in a GeneAmp Model 2400 thermal cycler (Eppendorf, Foster City, Calif.). The spent reactions were separated on 1.2% agarose gels and specific amplification products of about the expected size (420 bp) were recovered from the gel, purified using the QiaQuick™ Gel Extraction Kit (Qiagen, Valencia, Calif.), and directly sequenced using the degenerate PCR primers specified above. The resulting nucleotide sequences were assembled using ContigExpress, a component of Vector NTI Advance 10.3.0 (Invitrogen). These data were used to design gene-specific primers for primary and nested 5'- and 3'-RACE reactions, which were performed to determine the full-length, putative Sf-fdl gene sequence.

TABLE 1

Primer sequences
(Sequences are SEQ ID NOs: 10-33,
from top to bottom)

| Primer name | Nucleotide sequence (5' - 3') |
|---|---|
| ASPDEG | CGC AGT CSA RRT ACC AVG CRT CVA C |
| SPDEG | TAC TGC GGH GAR CCN CCN TGY GG |
| SFFDLASP1 | CGA CGA CCA CAG TAA CAC TAG CTC |
| SFFDLASP2 | AAA GCA CGT CGC GTG AAC TCT AGC |
| SFFDLASP3 | ATT GGG TCG GTG TCG TTG AAG TGC |
| SFFDLASP4 | GAG TCG CAC AGC ATG TTG |
| SFFDLSP3 | CAA CGC ATC TAC GCT GAG ATT CTC G |
| SFFDLSP4 | CGG AGC TAG TGT TAC TGT G |
| SFFDLCDNAASP | CGT CAT CCG CCT AGC TAT GTA ACC |
| SFFDLFL5OSP | GGT GCG TAG ATA GGC AGT GCG ATG |
| SFFDLSP1 | CCC GCA CGT GTA CGA TCT ACT GC |
| SFFDLFL31ASP | CTT GTA ACT CGA GGG CAG TGG |
| SFFDLSP2 | GTA CGA TCT ACT GCA ACG CAT CTA CG |
| SFFDLFL51SP | TAG GCA GTG CGA TGA AGT GGT G |
| SFFDLFL5N2SP | CAC CAT GAA GTG GTG GGG CGA G |
| SFFDLFL3N2ASP | CTA CAG GCA GGC GTG CGG GTT G |
| FDLFLSP | CAC CAT GTC CTT GGC TGT ATC G |
| FDLFLASP | TCA AAT GCA TTC GCC GGG ATT C |

TABLE 1-continued

Primer sequences
(Sequences are SEQ ID NOs: 10-33,
from top to bottom)

| Primer name | Nucleotide sequence (5' - 3') |
|---|---|
| SFFDLGST51SP | CCC GGG GCG CCA GCA GAG CGA CG |
| SFFDLGST5N2SP | CCC GGG GCG CCA GCA GAG |
| DMFDLGST3ASP | GAA TTC TCA AAT GCA TTC GCC GGG A |
| DMFDLGST5SP | CCC GGG AGG AGT CAC CAA GGC CC |
| SFGN3GST3ASPB | GAA TTC CTA AAA GTA ATT CCC TGT TAC G |
| GN3GST5SPB | CCC GGG TTT AAG TAT CGT TAA TCC TGG |

5'-RACE

Total RNA was isolated as described above, used for first-strand cDNA synthesis according to the GeneRacer™ protocol, and the resulting 3'- and 5'-anchored first strand cDNA was diluted to 50 µL. Five µL of this cDNA were then used as the template for 5' RACE reactions with 1.25 U of GoTaq® (Promega) and 200 nM of the SFFDLASP1 (Table 1) and GeneRacer™ 5' primers in a final volume of 50 µL of GoTaq® buffer. The reactions were incubated for 4 min at 95° C., cycled 12 times using (i) 30 sec at 95° C., (ii) 30 sec at 72 to 61° C. (with a decreasing temperature gradient of 1° C. per cycle), and (iii) 120 sec at 72° C. The reactions were cycled another 30 times using (i) 30 sec at 95° C., (ii) 20 sec at 61° C., and (iii) 120 sec at 72° C., and finally incubated for 5 min at 72° C. One µL of the spent 5'-RACE reaction was used as the template for a nested PCR with Promega's GoTaq® Green Mastermix and 200 nM of the SFFDLASP2 (Table 1) and GeneRacer™ 5'-nested primers in a total volume of 50 µL. These reactions were incubated for 90 sec at 95° C., cycled 25 times using (i) 30 sec at 95° C., (ii) 30 sec at 63° C., and (iii) 120 sec at 72° C., and finally incubated for 5 min at 72° C. The spent reactions were analyzed on a 1% agarose gel and an amplification product of approximately 1.4 kb in size was purified and used as the template for nested PCRs under the same conditions used for the primary PCRs, except the nested reactions included the SFFDLASP3 (Table 1) and GeneRacer™ 5'-nested primers and the annealing temperature was 65° C. The spent reactions were analyzed on a 0.9% agarose gel and the 1.4 kb amplification product was purified and directly sequenced using the SFFDLASP3, SFFDLASP4 (Table 1), and GeneRacer™ 5'-nested primers.

3'-RACE

The cDNA used for the 3'-RACE reactions was prepared from GeneRacer™ Oligo dT-primed total RNA, as described previously (24) and diluted to a final volume of 100 µL. Two µL of this cDNA preparation were then used as the template for a PCR with 1 U of Phusion™ DNA polymerase, 200 nM of the SFFDLSP3 and GeneRacer™ 3' primers, 1 M betaine, and 5% DMSO in a final volume of 50 µL of Phusion™ GC buffer. These reactions were incubated for 3 min at 98° C., cycled 45 times using (i) 30 sec at 98° C., (ii) 30 sec at 68° C. for the first five cycles, 63° C. for the next five cycles, 58° C. for the next five cycles, and 52° C. for the final 30 cycles, (iii) 60 sec at 72° C., and (iv) 20 sec at 75° C., and finally incubated for 2 min at 72° C. The spent reaction was analyzed on a 1% agarose gel, and the 1.2 Kb amplification product was purified and used as the template for nested PCRs with 0.8 U of Phusion™ DNA polymerase, 200 nM of the SFFDLSP4 and GeneRacer™ 3'-nested primers, and 1 M betaine in a total final volume of 50 µL of Phusion™ GC buffer. These reactions were incubated for 2 min at 98° C., cycled 45 times using (i) 20 sec at 98° C., (ii) 20 sec at 70° C. for the first five cycles, 65° C. for the next five cycles, 60° C. for the next five cycles, and 57° C. for the final 30 cycles, (iii) 40 sec at 72° C., and finally incubated for 2 min at 72° C. The 1.0 Kb amplification product was purified and directly sequenced using the primer SFFDLSP4.

Amplification of the Full-Length ORF from cDNA and Genomic DNA

Sf9 cDNA was simultaneously produced and primed with the Sf-fdl gene-specific primer SFFDLCDNAASP (Table 1) using SuperScript™ III reverse transcriptase (Invitrogen) according to the method of Shi et al. (24). Either 1.0 µL of this cDNA preparation or approximately 100 ng of Sf9 genomic DNA was then used as the template for PCRs containing 0.5 U of Phusion™ DNA polymerase, 1 M betaine, 0.2 mM of each dNTP and 200 nM of the SFFDLCDNAASP and SFFDLFL50SP primers (Table 1) in Phusion™ GC buffer. These reactions were incubated for 2 min at 98° C., cycled 40 times using (i) 20 sec at 98° C., (ii) 20 sec at 63° C. for the first five cycles, 58° C. for the next five cycles, and 55° C. for the final 30 cycles, (iii) 60 sec at 72° C., and finally incubated for 2 min at 72° C. The amplification products were purified on 1% agarose gels, recovered, and directly sequenced using internal primers.

Construction of Baculovirus Transfer Plasmids Encoding Native β-N-Acetylglucosaminidases Baculovirus transfer plasmids encoding full-length, untagged Dm-FDL or Sf-FDL were produced by using PCR to amplify the appropriate nucleotide sequences. The Sf-FDL coding sequence was assembled by producing two PCR amplimers with partially overlapping sequences, isolating the products, and then using them as templates for a third PCR designed to produce an amplimer encoding the full-length Sf-FDL protein. Briefly, the 3'-end of the Sf-fdl open reading frame was amplified from Sf9 cDNA prepared as described above in a PCR with 0.3 U of Phusion™ DNA polymerase, 0.2 mM of each dNTP, 1 M betaine, and 0.67 µM of the SFFDLSP1 and SFFDLFL31ASP primers (Table 1) in Phusion™ GC buffer. The reactions were incubated for 2 min at 98° C., cycled 45 times using (i) 20 sec at 98° C., (ii) 20 sec at 67° C. for the first five cycles, 62° C. for the next five cycles, 57° C. for the next five cycles, and 54° C. for the final 30 cycles, (iii) 40 sec at 72° C., and finally incubated for 2 min at 72° C. One µL of the spent reaction was used as the template for a nested PCR under essentially the same conditions, except the primers were SFFDLSP2 and SFFDLFL31ASP (Table 1). The spent secondary PCR was analyzed on a 1.2% agarose gel and the amplification product with the expected size was excised and purified as described above. The 5'-end of the Sf-fdl open reading frame was amplified using 1.0 µL of the spent nested 5'-RACE reaction described above as the template for a PCR with 0.5 U of Phusion™ DNA polymerase, 0.2 mM of each dNTP, 1 M betaine, and 1 µM of the SFFDLASP3 and SFFDLFL51SP primers (Table 1) in Phusion™ GC buffer. This reaction was incubated for 1 min at 98° C., cycled 13 times using (i) 30 sec at 98° C., (ii) 20 sec at 65 to 53° C. (with a decreasing temperature gradient of 1° C. per cycle), and (iii) 60 sec at 72° C., cycled another 30 times using (i) 30 sec at 98° C., (ii) 20 sec at 52° C., and (iii) 60 sec at 72° C., and finally incubated for 2 min at 72° C. The spent reaction was analyzed on a 1.0% agarose gel and the amplification product with the expected size was excised and purified as described above. Finally, the purified 3'- and 5'-ends of the predicted Sf-fdl ORF were combined in a PCR with 0.5 U of Phusion™ DNA polymerase, 0.2 mM of each dNTP, 1 M betaine, and 1 µM of the SFFDLFL5N2SP and SFFDLFL3N2ASP primers (Table 1) in Phusion™ GC buffer. This reaction was incubated for 1 min at 98° C., cycled four times using (i) 30 sec at 98° C. and (ii) 90 sec at 72° C., cycled another 25 times using (i) 30 sec at 98° C., (ii) 20 sec at 52° C., and (iii) 80 sec at 72° C., and finally incubated for 2 min at 72° C. The spent reaction was analyzed on a 1.0% agarose gel, and the amplification product of the expected size was excised, purified and cloned into pENTR™/D-TOPO® according to the manufacturer's protocol. Sequencing revealed two clones that each had single, but different non-synonymous mutations and these were used to assemble a plasmid designated pENTR™/D-TOPO®-Sf-fdl-FL encoding the full-length, wild type Sf-FDL protein.

The Dm-fdl open reading frame was amplified from 50 ng of a plasmid designated pIEBac-CG8824Myc in a PCR with 2 U of Phusion™ DNA polymerase, 0.2 mM of each dNTP, 0.1 µg of the FDLFLSP and FDLFLASP primers (Table 1) in Phusion™ HF buffer. This plasmid encodes the *Drosophila melanogaster* fdl gene open reading frame with a c-Myc epitope tag under the transcriptional control of a baculovirus IE1 promoter. See Geisler et al. (2008) J. Biol. Chem., 283: 11330-11339.

These reactions were incubated for 1 min at 98° C., cycled 30 times using (i) 20 sec at 98° C., (ii) 20 sec at 55° C., and (iii) 90 sec at 72° C., and finally incubated for 2 min at 72° C. The spent reaction was analyzed on a 0.8% agarose gel, and the amplification product of the expected size was excised, purified and cloned into pENTR™/D-TOPO® according to the manufacturer's protocol. An error-free clone was identified by sequencing and designated pENTR™/D-TOPO®-Dm-fdl-FL.

Construction of Baculovirus Transfer Plasmids Encoding GST-Tagged β-N-Acetylglucosaminidases Transfer plasmids encoding N-terminally GST-tagged ectodomains of the various β-N-acetylglucosaminidases examined in this study were also produced using PCR-based approaches. Generally, TMpred (25) was used to predict the sequences encoding the ectodomain of each protein, and then these sequences were amplified using primers designed to introduce SmaI and EcoRI sites on their 5'- and 3'-ends, respectively. Thus, each of the resulting PCR products was designed for subsequent directional cloning into the SmaI and EcoRI sites of the baculovirus transfer plasmid pAcSecG2T (BD Biosciences, San Jose, Calif.), to position the relevant coding sequences downstream and in-frame with the GST coding sequence in this vector.

The predicted Sf-fdl ectodomain coding sequence was amplified using pENTR™/D-TOPO®-Sf-fdl-FL as the template for a PCR with 0.5 U of Phusion™ DNA polymerase, 0.2 mM of each dNTP, 1 M betaine, 0.2 µM of the SFFDLFL3N2ASP and 10 nM of the SFFDLGST5I1SP primers (Table 1) in Phusion™ GC buffer. The reaction was incubated for 1 min at 98° C., cycled four times using (i) 20 sec at 98° C., (ii) 20 sec at 58° C., and (iii) 90 sec at 72° C., after which primer SFFDLGST5N2SP was added to 0.2 µM, incubated for 1 min at 98° C., cycled another 30 times using (i) 20 sec at 98° C., (ii) 20 sec at 60° C., and (iii) 90 sec at 72° C., and finally incubated for 2 min at 72° C. The spent reaction was analyzed on a 1.0% agarose gel, and the amplification product of the expected size was excised and purified. The purified amplimer was then treated with 5 U of Taq DNA polymerase (New England Biolabs, Ipswich, Mass.) for 15 minutes in the presence of 0.2 mM dATP and the manufacturer's standard Taq buffer. The reaction product was cloned into pCR®2.1-TOPO® (Invitrogen) according to the manufacturer's instructions, yielding pCR2.1®-TOPO®-Sf-fdl-SOL. An error-free clone was identified by sequencing and the insert was excised with SmaI and EcoRI, gel-purified, and subcloned into the corresponding sites of pAcSecG2T to produce the transfer plasmid designated pAcSecG2T-Sf-fdl-SOL.

The predicted Dm-fdl ectodomain coding sequence was amplified using pENTR™/D-TOPO®-Dm-fdl-FL as the template for a PCR with 2 U of Phusion™ DNA polymerase, 0.2 mM of each dNTP, and 1 µM of the DMFDLGST3ASP and DMFDLGST5SP primers (Table 1) in Phusion™ HF buffer. The reaction was incubated for 1 min at 98° C., cycled five times using (i) 15 sec at 98° C., (ii) 20 sec at 50° C., and (iii) 75 sec at 72° C., cycled another 30 times using (i) 15 sec at 98° C., (ii) 20 sec at 64° C., and (iii) 75 sec at 72° C., and finally incubated for 2 min at 72° C. The amplimer was subsequently purified, Taq-treated, cloned, sequence-verified and subcloned as described above to produce the intermediate plasmid pCR®2.1TOPO®-Dm-fdl-SOL and the final baculovirus transfer plasmid, pAcSecG2T-Dm-fdl-SOL.

The predicted Sf-GlcNAcase3/SfHex ectodomain coding sequence was amplified using pENTR™/D-TOPO®-Sf-GlcNAcase3 as the template for a PCR with 2 U of Phusion™ DNA polymerase, 0.2 mM of each dNTP, and 1 µM of SFGN3GST3ASPB and GN3GST5SPB primers (Table 1) in Phusion™ HF buffer, with cycling conditions identical to those used to generate the Dm-fdl ectodomain amplimer. The resulting product was purified, Taq-treated, cloned into pCR®4-TOPO®, sequence-verified, and subcloned as described above to produce the intermediate plasmid pCR®4-TOPO®-Sf-GlcNAcase3-SOL and the final baculovirus transfer plasmid, pAcSecG2T-Sf-GlcNAcase3-SOL.

Isolation of Baculovirus Expression Vectors

Each of the baculovirus transfer plasmids described in the preceding sections was extracted from large-scale *E. coli* cultures and purified by isopycnic ultracentrifugation on ethidium bromide-cesium chloride gradients, as described previously (23). The pENTR plasmids were then used to produce recombinant baculoviruses by the BaculoDirect™ method (Invitrogen), according to the manufacturer's protocol. The transfer plasmids encoding GST-tagged β-N-acetylglucosaminidases were used to produce viruses by a standard allelic transplacement method (3,4) with Bsu36I-digested BacPAK6 viral DNA (26) as the target for homologous recombination. Each recombinant baculovirus vector was plaque-purified, amplified in Sf9 cells, and titered by plaque assay on Sf9 cells, as described previously (4). The recombinant viruses encoding various full-length, untagged β-N-acetylglucosaminidase genes were designated AcSfGlcNAcase-3 (18), AcDm-FDL, and AcSf-FDL and those encoding N-terminally GST-tagged ectodomains of the various β-N-acetylglucosamirnidases were designated AcGSTSfGlcNAcase-3, AcGSTDm-FDL, and AcGSTSf-FDL, respectively. The parental virus used to produce these viruses, which also served as a negative control for some of the experiments included in this study, was *Autographa californica* nucleopolyhedrovirus (AcMNPV).

Expression of Recombinant Proteins in Insect Cells

Sf9 cells were seeded into 100 mL of ESF 921 medium in 250 mL DeLong flasks (Corning Glass Works, Corning, N.Y.) and allowed to grow to a density of about $1.5$-$2.0 \times 10^6$ cells/mL at 28° C. and 125 rpm in a Forma Model 4580 rotary platform shaker-incubator (Forma Scientific, Inc., Marietta, Ohio). The cells were then infected with the appropriate baculovirus at a multiplicity of infection of about 1 plaque-forming unit/cell and incubated for another 72 h under the same conditions.

Isolation of Purified Microsomal Fractions

The isolation of microsomal fractions from baculovirus-infected Sf9 cells has been described previously (18). Briefly, the cells were Dounce-homogenized and microsomes were isolated by ultracentrifugation onto sucrose cushions. The microsomes were solubilized in β-N-acetylglucosaminidase assay buffer (100 mM citrate-phosphate buffer, pH 6.0) containing 0.5% (v/v) Triton-X-100, total protein concentrations were determined using a commercial bicinchoninic acid assay (Pierce Biotechnology Inc., Rockford, Ill.), and samples containing equal amounts of total protein were assayed for β-N-acetylglucosaminidase activity, as described below.

For a subset of these experiments, which was designed to examine the nature of the association between the enzyme activity and membranes, freshly prepared microsomes were either held or sonicated on ice with ten pulses from a Branson Model 450 Sonifier (Danbury, Conn.) adjusted to 50% output. The microsomes were then pelleted by centrifugation for 10 min at top speed in a microcentrifuge (Hermle Model Z180M) and the pellets were resuspended in β-N-acetylglucosaminidase assay buffer. The sonication and centrifugation steps were repeated, the final pellets were resuspended in β-N-acetylglucosaminidase assay buffer containing 0.5% (v/v) Triton-X-100 (Sigma Chemical Company, St. Louis, Mo.), and then the solubilized microsomes were assayed for β-N-acetylglucosaminidase activity, as described below.

Glutathione Affinity Chromatography

The GST-tagged ectodomains of the various β-N-acetylglucosaminidases examined in this study were purified from the extracellular fraction of Sf9 cells infected with AcGSTS-fGlcNAcase-3, AcGSTDm-FDL, or AcGSTSf-FDL. Briefly, the cells were removed from each infected cell culture at 72 h postinfection by centrifugation for 5 min at 1000×g, and the supernatant was harvested and ultracentrifuged for 30 min in a Ti45 rotor at 30,000 rpm and 4° C. in a Beckman Optima 100XL ultracentrifuge (Beckman Coulter; Fullerton, Calif.). The resulting supernatant was diluted with an equal volume of ice-cold GST purification buffer (25 mM Tris, 150 mM NaCl, 1 mM EDTA, pH 8.0), solid ammonium sulfate was added to 90% saturation, and the samples were stirred on ice until the salt was fully dissolved. The samples were subsequently ultracentrifuged for 20 minutes in a Ti45 rotor at 30,000 rpm and 4° C. and the resulting pellet was re-dissolved in a minimal volume of GST purification buffer. The samples were then transferred to dialysis tubing with a 50 kDa molecular weight cutoff (Spectrum Medical Industries Inc.; Laguna Hills, Calif.) and dialyzed overnight at 4° C. against 100 volumes of GST purification buffer supplemented with 1 mM phenylmethylsulfonyl fluoride (PMSF). Each GST-tagged protein was then adsorbed to a 1.5 mL bed volume of Glutathione Sepharose 4 Fast Flow (GE Healthcare; Uppsala, Sweden) pre-equilibrated with GST purification buffer in a plugged 20 mL Econo-Pac column (BioRad; Hercules, Calif.) for one hour at 4° C. on a shaking platform. Subsequently, the fluid was drained from the column, the affinity matrix was washed twice with 10 mL of GST purification buffer, and the GST-tagged proteins were eluted with GST purification buffer supplemented with 5 mM reduced glutathione. Fractions were collected and purity was assessed by SDS-PAGE with Coomassie Blue staining, the presence of the GST-tagged proteins was assessed by SDS-PAGE and immunoblotting with a GST-specific antiserum, and enzymatic activity was assessed using p-nitrophenyl-β-N-acetylglucosaminide as the substrate, as described previously (18).

β-N-acetyleucosaminidase Activity Assays

Enzyme activity assays were performed using either solubilized microsomal fractions or affinity-purified recombinant proteins isolated from baculovirus-infected Sf9 cells. For the microsomal membrane assays, microsomes were prepared and extracted as described above and samples containing equal amounts of total protein were assayed in a total volume of 0.050 mL containing 25 pmol of various pyridylamine (PA)-tagged glycan substrates. The enzymatic activity of the affinity-purified recombinant proteins was assayed under identical conditions, except the amounts of purified protein used for these assays were equalized by immunoblotting, rather than by total protein assays. The substrates used in this study included GlcNAcβ2Manα6(GlcNAcβ2Manα3)Manβ4GlcNAcβ4GlcNAc-PA (GnGn; CalBiochem, La Jolla, Calif.), GlcNAcβ2Manα6(Manα3)Manβ4GlcNAcβ4GlcNAc-PA (GnM), and Manα6(GlcNAcβ2Manα3)Manβ4GlcNAcβ4GlcNAc-PA (MGn). After being incubated for various times at 37° C., each reaction was diluted to 0.150 mL with β-N-acetylglucosaminidase reaction buffer and the products were analyzed by reverse phase high performance liquid chromatography, as described previously (27). GnGn, GnM, MGn, and Manα6(Manα3)Manβ4GlcNAcβ4GlcNAc-PA (MM), were used as standards for the chromatographic analyses.

RNA Interference

In general, the RNA interference approach used in this study involved transforming Sf9 cells with an immediate early expression plasmid encoding an inverted repeat derived from a portion of the Sf-fdl coding sequence, with the inverted repeat separated by a *Drosophila melanogaster* white gene intron, as originally described by Lee and Carthew (26). Briefly, the Sf-fdl coding sequence from nucleotides 355 to 855 was amplified using pENTR™/D-TOPO®-Sf-fdl-FL as the template for a PCR with 0.5 U of Phusion™ DNA polymerase, 0.2 mM of each dNTP, and 1 mM each of the SFFDLRNAIASP and SFFDLRNAISP primers (Table 1), which introduced XbaI sites onto both ends, in Phusion™ HF buffer. The reaction was incubated for 30 seconds at 98° C., cycled five times using (i) 20 sec at 98° C., (ii) 20 sec at 54° C., and (iii) 30 sec at 72° C., cycled another 30 times using (i) 20 sec at 98° C., (ii) 20 sec at 64° C., and (iii) 30 sec at 72° C., and finally incubated for 2 min at 72° C. The spent reaction was analyzed on a 1.2% agarose gel and the amplification product was excised, purified, Taq-treated, and cloned into pCR4®-TOPO® to produce pCR4®-TOPO®-SfFdlRNAi. An error-free clone was identified by sequencing and the insert was excised with XbaI and gel-purified. One copy of the insert was subcloned in antisense orientation into the AvrII site and a second copy was subcloned in sense orientation into the NheI site of pGEM-WIZ (27); (obtained from the *Drosophila* Genomics Resource Center) to produce pGEM-WIZ-SfFdlRNAi. Finally, the Sf-fdl inverted repeat and white gene intron cassette was excised with SacII and NotI and subcloned into the corresponding sites of pIE1HR3 (29) to produce pIE1HR3SfFdlRNAi. This plasmid was used along with pIE1Neo to co-transfect Sf9 cells using a modified calcium phosphate method, as described previously (4). The transfected cells were then selected and neomycin-resistant clones were isolated by limiting dilution, as described previously (29). The levels of specific, processing β-N-acetylglucosaminidase activity in the parental and transformed cells were finally compared by HPLC analysis of the products obtained by reacting microsomal membrane preparations with GnGn, as described above.

The following examples are provided to illustrate certain embodiments of the invention. These examples are not intended to limit the invention in any way.

EXAMPLE I

Cloning of a Novel Processing
β-N-Acetylglucosamidase from SF9 Cells and
Characterization Thereof Isolation and Characterization of an fdl Gene
Homolog from Sf9 Cells Our effort to isolate an fdl gene homolog from Sf9 cells was informed and facilitated by the availability of genome sequence data from several insect species and also by our previous efforts to isolate the gene encoding the processing β-N-acetyl-glucosaminidase activity from this cell line. tBLASTn analysis of the *A. aegypti, A. gambiae, A. mellifera, B. mori, D. pseudoobscura* and *T. castaneum* genomes with the Dm-fdl gene as the query yielded exons from each species encoding peptides phylogenetically related to Dm-fdl (data not shown). We subsequently used a splice site prediction algorithm to join the relevant exons and identify open reading frames encoding at least partial, putative β-N-acetylglucosaminidases from each insect species. Importantly, a CLUSTAL-W alignment of the predicted products of these open reading frames with the Dm-fdl gene product revealed conserved amino acid sequences that were not conserved in the Sf-GlcNAcase-1 or SfGlcNAcase-3 gene products identified in our previous study (18). These were used to design degenerate oligonucleotides for high fidelity PCRs with Sf9 cDNA or genomic DNA as the templates. These PCRs yielded an amplification product of about the expected size (420 bp), which appeared to be specific because it was not observed in control reactions in which either one of the degenerate oligonucleotides was excluded (data not shown). This product was directly sequenced and the translation product was found to be highly similar to a fragment of the *D. melanogaster* and putative *B. mori* FDL proteins (data not shown). Accordingly, we used this sequence to design gene-specific primers for 5'- and 3'-RACE reactions, which yielded the nucleotide sequence of the full length, putative Sf-fdl open reading frame, as detailed above.

The 5'-RACE reactions yielded a specific 1.4 Kb amplification product, which overlapped with the sequence of the original degenerate PCR product, extended it by 1161 bp in the 5' direction, and included a potential translational initiation site (data not shown). The 3'-RACE reactions yielded a specific 1.0 Kb amplification product, which also overlapped with the sequence of the original degenerate PCR product, extended it by 734 bp in the 3' direction, and encoded a translational termination site. A contiguous nucleotide sequence of 2319 bp was assembled by joining the sequences of the degenerate amplimer, the 5'-RACE product, and the 3'-RACE product. The accuracy of this sequence was confirmed by PCR with gene specific primers using both Sf9 cDNA and genomic DNA as the templates, followed by direct sequencing of the products, as described in Experimental Procedures.

In Silico Analysis of the Sf9 Cell Fdl Gene Homolog

Figure 1:
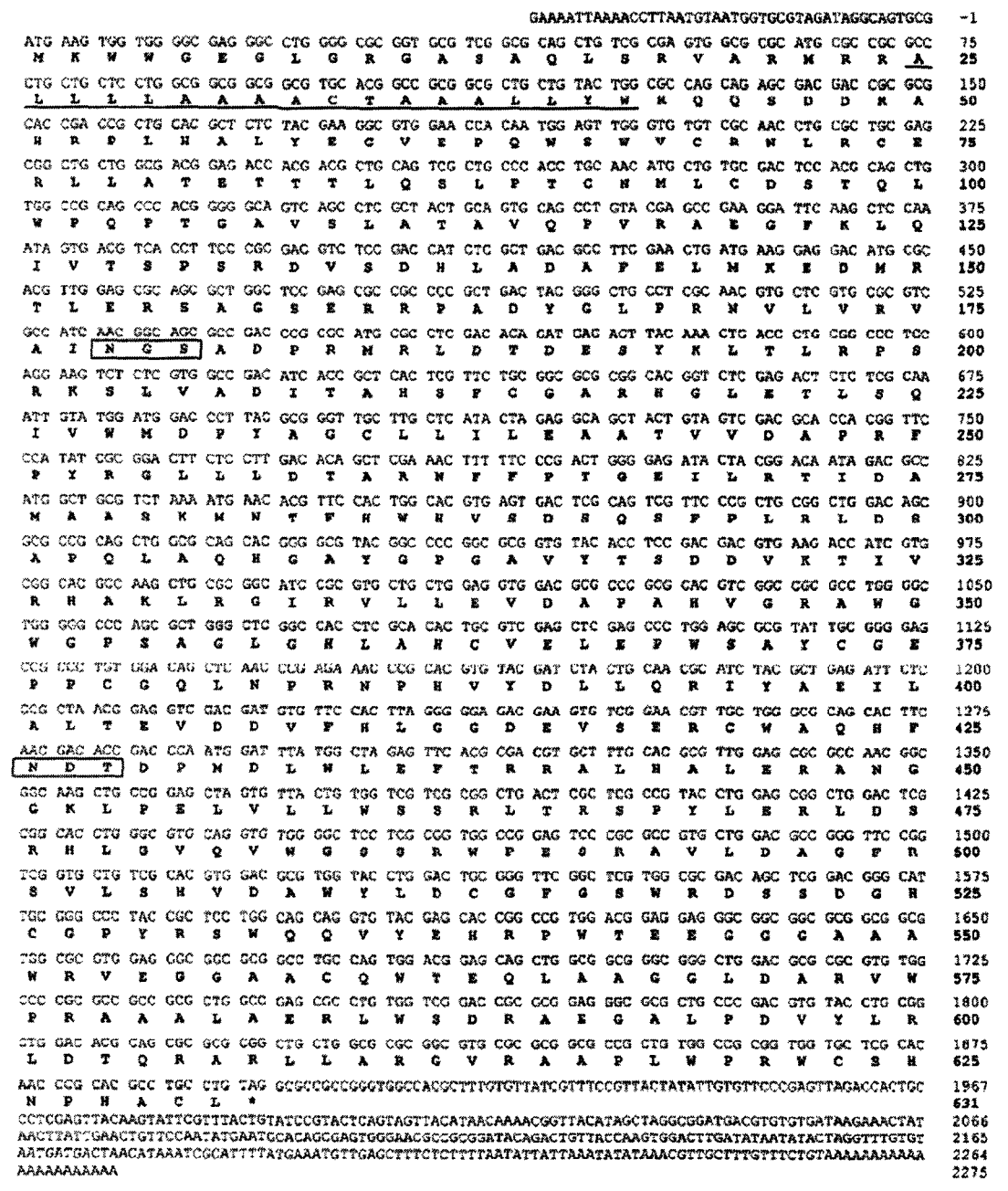

The full-length Sf-fdl nucleotide sequence and theoretical amino acid sequence of the Sf-FDL polypeptide are shown in FIG. 1. The nucleotide sequence includes a single long open reading frame of 1896 bp, which has a GC content of 69%. The theoretical product of this open reading frame is a polypeptide consisting of 631 amino acids, which has a calculated molecular mass of 70,530 Da and a calculated isoelectric point of 7.18. The theoretical protein also has an N-terminal transmembrane domain (underlined in FIG. 1), which extends from amino acids 25 to 42 with in/out topology, according to the TMHMM and TopPred2 algorithms (29). Thus, the putative *S. frugiperda* FDL polypeptide appears to be a type II transmembrane protein with a short cytoplasmic tail. This is consistent with the idea that the Sf-fdl gene encodes an N-glycan processing enzyme because all N-glycan processing enzymes characterized to date have been predicted or shown to be transmembrane proteins with type II topology (30-32). The putative Sf9 cell enzyme also includes two potential N-glycosylation sites, which are boxed in the amino acid sequence shown in FIG. 1.

A phylogenetic analysis of the predicted Sf-fdl gene product showed that it is related to known hexosaminidases, including the human alpha (Acc. No. NM_000520; 33) and beta (Acc. No. NM_000521; 34) hexosaminidases, as well as SfGlcNAcase-1 (Acc. No. DQ249307; 18) and SfGlcNAcase-3/Sfhex (Acc. No. DQ249309; 17,18), as expected (FIG. 2). Strikingly, however, this analysis also revealed that the predicted Sf-fdl gene product is much more closely related to the Dm-fdl gene product (Acc. No. NM_165909; 16) than to either of the *S. frugiperda* hexosaminidase gene products, despite the fact that *Spodoptera* and *Drosophila* belong to distinct insect Orders, which diverged well over 300 million years ago (35). Together, these results indicated that we had successfully isolated a Dm-fdl gene homolog from Sf9 cells. In addition, the much closer relationship between these two genes and the more distant relationship between the Dm-fdl and SfGlcNAcase-3/Sfhex genes supports the conclusion that this newly-isolated gene encodes the specific, processing β-N-acetylglucosaminidase in Sf9 cells.

Expression and Biochemical Analysis of the Native Sf-Fdl Gene Product

Figure 3:
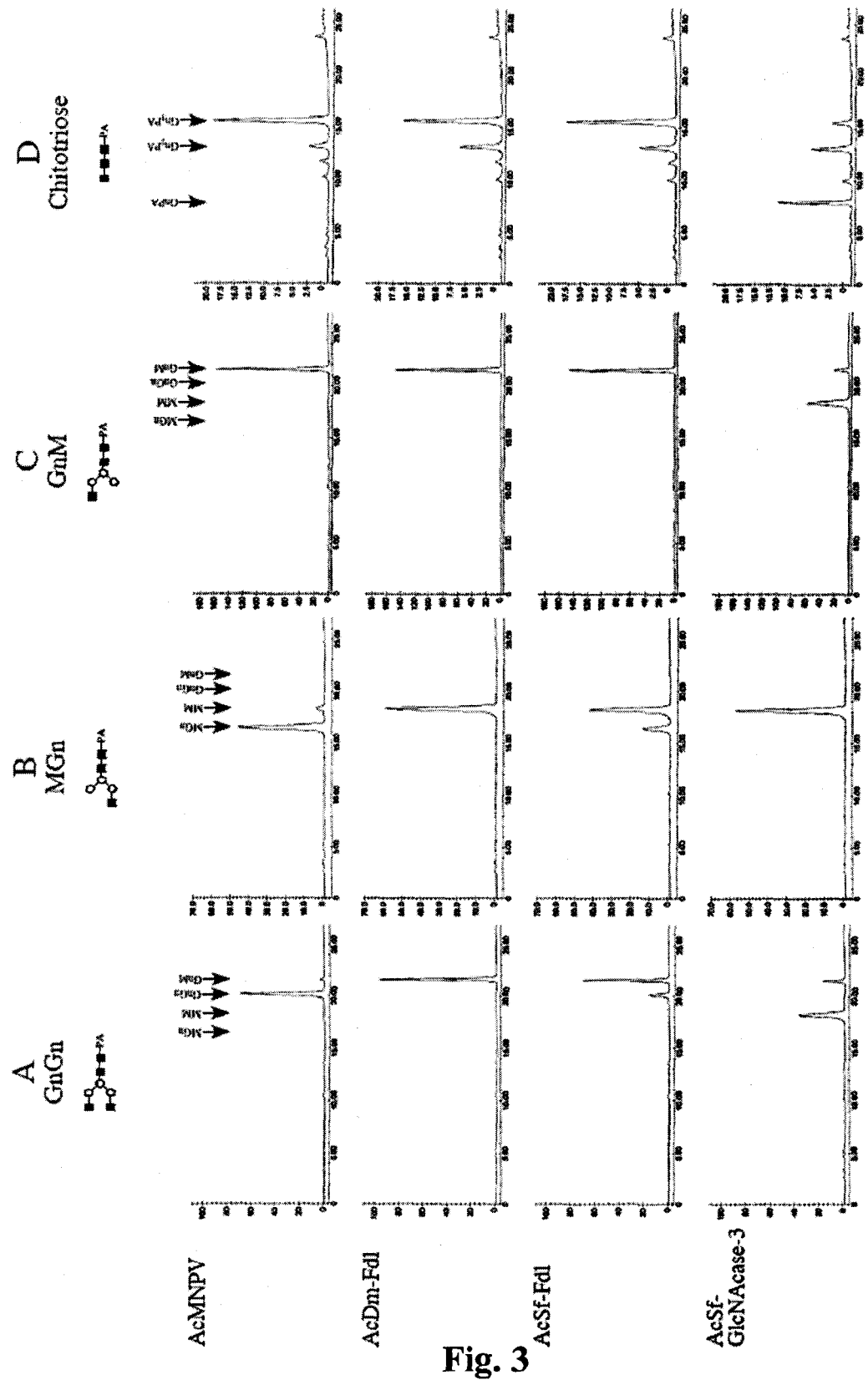
FIG. 3. Substrate specificity of Sf-FDL. Various glycan substrates, including GnGn (A), MGn (B), GnM (C), and chitotriose (D) were incubated for 16 h with microsomal fractions containing 10 ug of total protein from Sf9 cells infected with AcMNPV, AcDm-FDL, AcSf-FDL, or AcGlcNAcase-3. The reaction products were then recovered and analyzed by reverse-phase HPLC, as described in Experimental Procedures. The arrows show the elution times for each of the relevant glycans.

The full-length Sf-FDL coding sequence was subcloned into a baculovirus transfer plasmid and the resulting construct was used to isolate a recombinant baculovirus, AcSf-FDL, that was used, in turn, for high-level expression of the native cDNA product in insect cells. The parental baculovirus (Ac-MNPV) was used as a negative control and recombinant baculoviruses encoding Dm-FDL (AcDm-FDL) or Sf-GlcNAcase-3/SfHex (AcSfGlcNAcase-3) were used to directly compare the enzymatic activities of the Sf-fdl, Dm-fdl, and Sf-GlcNAcase-3/SfHex gene products. Individual Sf9 cell cultures were infected with the appropriate baculoviruses and then crude microsomal membrane fractions were prepared and assayed for enzymatic activity with various PA-tagged glycans as substrates, as described above. The results showed that negative control microsomes from AcMNPV-infected cells had very little effect on GnGn, while microsomes isolated from either AcDm-FDL- or AcSf-FDL-infected cells converted this substrate to GnM (FIG. 3A, top three panels). In contrast, microsomes from AcGlcNAcase-3-infected cells converted GnGn to both GnM and MM in parallel assays (FIG. 3A, bottom panel). These results indicated that Sf-FDL and Dm-FDL specifically removed only the terminal N-acetylglucosamine residue from the α3-branch of GnGn, whereas SfGlcNAcase-3/SfHex had a broader spectrum of activity and removed the terminal N-acetylglucosamine residues from both branches of GnGn in these assays.

This was supported by the results of additional assays in which other glycans were used as substrates. Microsomes from cells infected with AcDm-FDL, AcSf-FDL, or AcSf-GlcNAcase-3 all removed the terminal N-acetylglucosamine residue from the α3-branch of MGn to produce MM, as expected (FIG. 3B, lower three panels). Significantly, however, microsomes from AcDm-FDL- and AcSf-FDL- (FIG. 3C, middle two panels) infected cells failed to remove the terminal N-acetylglucosamine from the α6-branch of GnM, while those from AcSfGlcNAcase-3-infected cells (FIG. 3C, bottom panel) clearly converted GnM to MM. These results confirmed that Sf-FDL and Dm-FDL are more highly specific enzymes that remove only the terminal N-acetylglucosamine residue from the α3-branch of glycan substrates in these assays. This substrate specificity distinguishes these enzymes from the SfGlcNAcase-3/SfHex gene product, as this latter readily removed the terminal N-acetylglucosamine residues from both branches of biantennary glycan substrates.

The relatively broader spectrum of activity observed with the SfGlcNAcase-3/SfHex gene product was underscored by the ability of microsomes from AcSfGlcNAcase-3-infected cells to efficiently convert chitotriose to chitobiose and chitobiose to a PA-tagged N-acetylglucosamine residue (FIG. 3D, bottom panel). In contrast, microsomes from AcDm-FDL- or AcSf-FDL-infected cells (FIG. 3D, middle two panels) converted only small amounts of chitotriose to chitobiose and produced no PA-tagged N-acetylglucosamine. In fact, microsomes from AcMNPV-infected cells (FIG. 3D, top panel) produced nearly as much chitobiose as the microsomes from AcDm-FDL- or AcSf-FDL-infected cells, suggesting that the apparent ability of these latter two enzymes to hydrolyze chitotriose was an artifact resulting from contaminating chitinase activity in the crude microsomal preparations.

The results of the experiments described in this specification show that the Sf-fdl gene product is orthologous to the Dm-fdl gene product, which is responsible for N-glycan processing in *D. melanogaster* (16), and paralogous to the SfGlcNAcase-3/SfHex gene product, which we previously concluded was more likely to be responsible for N-glycan and/or chitin degradation in *S. frugiperda* (18). Furthermore, the isolation of a Dm-fdl ortholog from Sf9 cells, its substrate specificity, and the relatively non-specific nature of the SfGlcNAcase-3/SfHex gene product provide compelling evidence to suggest that the former, not the latter is the N-glycan processing enzyme in Sf9 cells.

pH Optimum of the Sf-Fdl Gene Product

Figure 4:
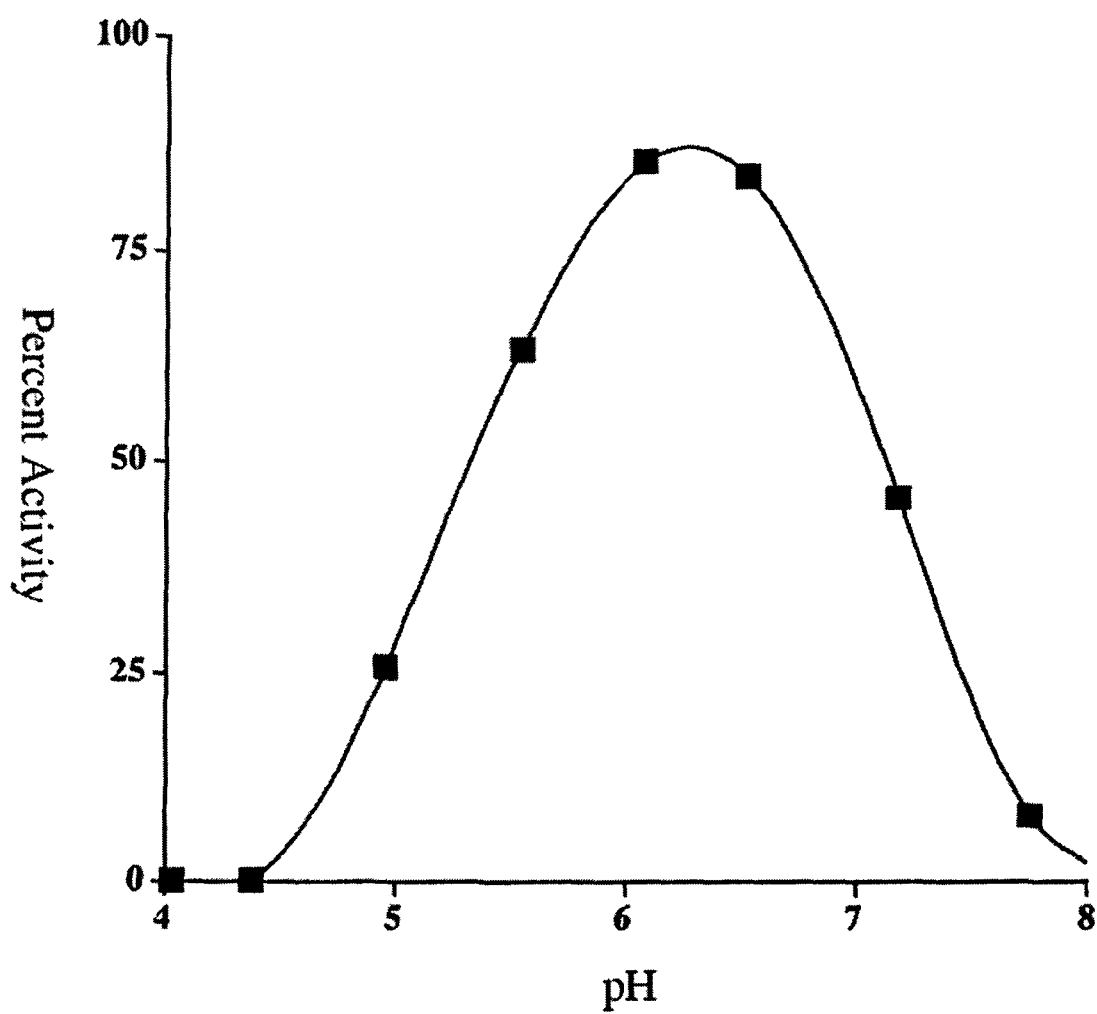
FIG. 4. pH optimum of Sf-FDL. Microsomal fractions containing 10 ug of total protein from AcSf-FDL-infected Sf9 cells were incubated for 16 h with GnGn at pH values between 4.0 and 8.0, and then the reaction products were recovered and analyzed by reverse-phase HPLC, as described in Experimental Procedures. The plot shows the relative percentages of GnM produced at each pH as a percentage of the area under the GnM peak divided by the sum of the area under the GnGn and GnM peaks.

In their seminal study on the endogenous processing β-N-acetylglucosaminidase activity in microsomal membranes isolated from Sf21 cells, Altmann and coworkers (9) found that it had a pH optimum for GnGn hydrolysis of 6.0. This was consistent with the idea that the activity measured in these assays was involved in N-glycan processing, rather than degradation, because a processing enzyme would be expected to reside in the Golgi apparatus and have a pH optimum around 6.0-6.5, whereas a degradative enzyme would be expected to reside in the lysosomal compartment and have a more acidic optimal pH. We and Tomiya and coworkers found that the SfGlcNAcase-3/SfHex gene product had a pH optimum of 5.5 and took this as one line of evidence that this enzyme could not account for the processing activity identified by Altmann and coworkers (1995) and was more likely to be involved in N-glycan or chitin degradation (18). Tomiya and coworkers also found that the SfGlcNAcase-3/SfHex gene product had a pH optimum of 5.5, but concluded that it is involved in N-glycan processing in Sf9 cells because it has the same pH optimum as Dm-FDL (16) and it is at least partially active at the higher pH of secretory compartments, such as the trans-Golgi network (17). Hence, it was of interest to examine the optimal pH of the Sf-fdl gene product. Microsomal membranes were isolated from AcSf-FDL-infected Sf9 cells and assayed for GnGn hydrolysis at various pH values. The results showed that the pH optimum of the Sf-fdl gene product is 6.0 and that it has nearly optimal activity at pH 6.5, as well (FIG. 4). Thus, the pH optimum of the Sf-fdl gene product is identical to that of the processing activity originally identified in microsomal fractions from Sf21 cells by Altmann and coworkers (9). Furthermore, the range of optimal or near-optimal pH values for this enzyme more clearly encompasses the range of pH values found within late secretory pathway compartments, such as the trans-Golgi network, than the SfGlcNAcase-3/SfHex gene product. Thus, these results also support the idea that the Sf-fdl gene product, not the SfGlcNAcase-3/SfHex gene product, is the specific, processing β-N-acetylglucosaminidase in Sf9 cells.

Biochemical Analysis of the Purified, Ectodomain of Sf-FDL

Figure 5:
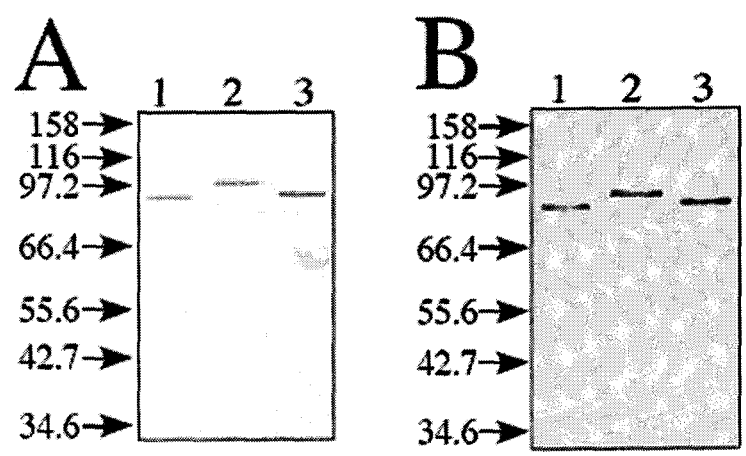
FIG. 5. Expression and purification of GST-tagged β-N-acetylglucosaminidase ectodomains. The GST-tagged, ectodomains of Sf-FDL (lanes 1), Dm-FDL (lanes 2), and SfGlcNAcase-3/Sfhex (lanes 3) were expressed in recombinant baculovirus-infected Sf9 cells and purified from the extracellular fraction by glutathione affinity chromatography, as described in Experimental Procedures. Equal amounts of the purified products were then analyzed by (A) SDS-PAGE with Coomassie Blue staining or (B) SDS-PAGE with immunoblotting using a GST-specific antiserum.

Each of the biochemical assays performed to this point in our study had involved the use of crude microsomes isolated from Sf9 cells infected with recombinant baculoviruses encoding the relevant β-N-acetylglucosaminidases. These assays were relevant because they mimicked the original assays of the endogenous processing β-N-acetylglucosaminidase activity in Sf21 cells and provided data on the substrate specificities of full-length, untagged forms of each of the enzymes of interest. However, one criticism of these assays is that they did not involve the use of purified enzymes. To address this issue, we isolated recombinant baculoviruses encoding N-terminally GST-tagged ectodomains of Sf-FDL, Dm-FDL, and SfGlcNAcase-3/Sfhex, as described in Experimental Procedures. Each was expressed in Sf9 cells and purified from the extracellular fraction using glutathione affinity chromatography, as described in Experimental Procedures. Analysis of the purified products by SDS-PAGE with Coomassie Blue staining (FIG. 5A) or immunoblotting with anti-GST (FIG. 5B) established that each had been effectively purified and normalized. Subsequently, equivalent amounts of these purified protein preparations were assayed for β-N-acetylglucosaminidase activity using various glycan substrates.

Figure 6:
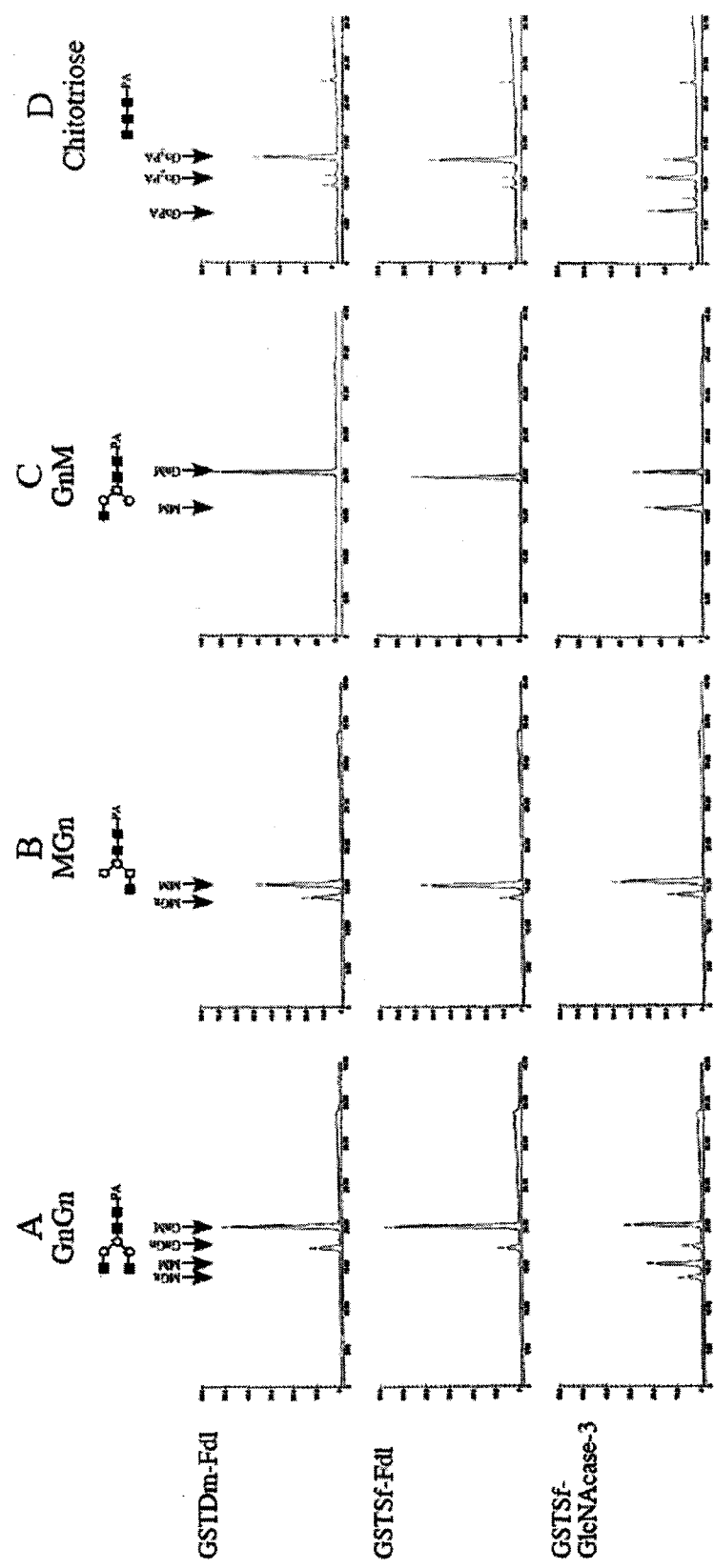
FIG. 6. Substrate specificity of the GST-tagged, ectodomains of Sf-FDL, Dm-FDL, and SfGlcNAcase-3/Sf-hex. Equal amounts of each enzyme were incubated for 2 h with GnGn (A), MGn (B), GnM (C), or chitotriose (D) and the reaction products were recovered and analyzed by reverse-phase HPLC, as described in Experimental Procedures. The arrows show the elution times for each of the relevant glycans.

The results of these assays showed that the GST-tagged ectodomains of both Dm-FDL and Sf-FDL converted GnGn to GnM (FIG. 6A; middle two panels), while the GST-tagged ectodomain of the GlcNAcase 3/Sfhex protein converted this substrate to GnM, MGn, and MM (FIG. 6A, bottom panel). All three enzymes removed the terminal N-acetylglucosamine residue from the α3-branch of MGn to produce MM (FIG. 6B), as expected, but only the SfGlcNAcase 3/Sfhex protein removed the terminal N-acetylglucosamine from the α6-branch of GnM to produce MM (FIG. 6C, bottom panel). Neither Dm-FDL nor Sf-FDL had any detectable effect on this glycan (FIG. 6C, middle two panels). Similarly, only the SfGlcNAcase-3/Sfhex protein hydrolyzed chitotriose to produce chitobiose and PA-tagged N-acetylglucosamine monomers (FIG. 6D; bottom panel), while Dm-FDL and Sf-FDL had virtually no effect on this glycan (FIG. 6D, middle two panels).

These data supported the major conclusion drawn from the experiments performed with the full-length, untagged forms of these enzymes, which was that Dm-FDL and Sf-FDL are specific for the terminal N-acetylglucosamine on the α3-branch of biantennary N-glycan substrates, while SfGlcNAcase-3/SfHex has a much broader spectrum of β-N-acetylglucosaminidase activity. Again, the specificities of Sf-FDL and Dm-FDL are consistent with their proposed function in N-glycan processing and with the conclusion that the Sf-fdl gene encodes the membrane bound, processing β-N-acetylglucosaminidase activity originally identified in Sf21 cells by Altmann and coworkers (1995).

Figure 7:
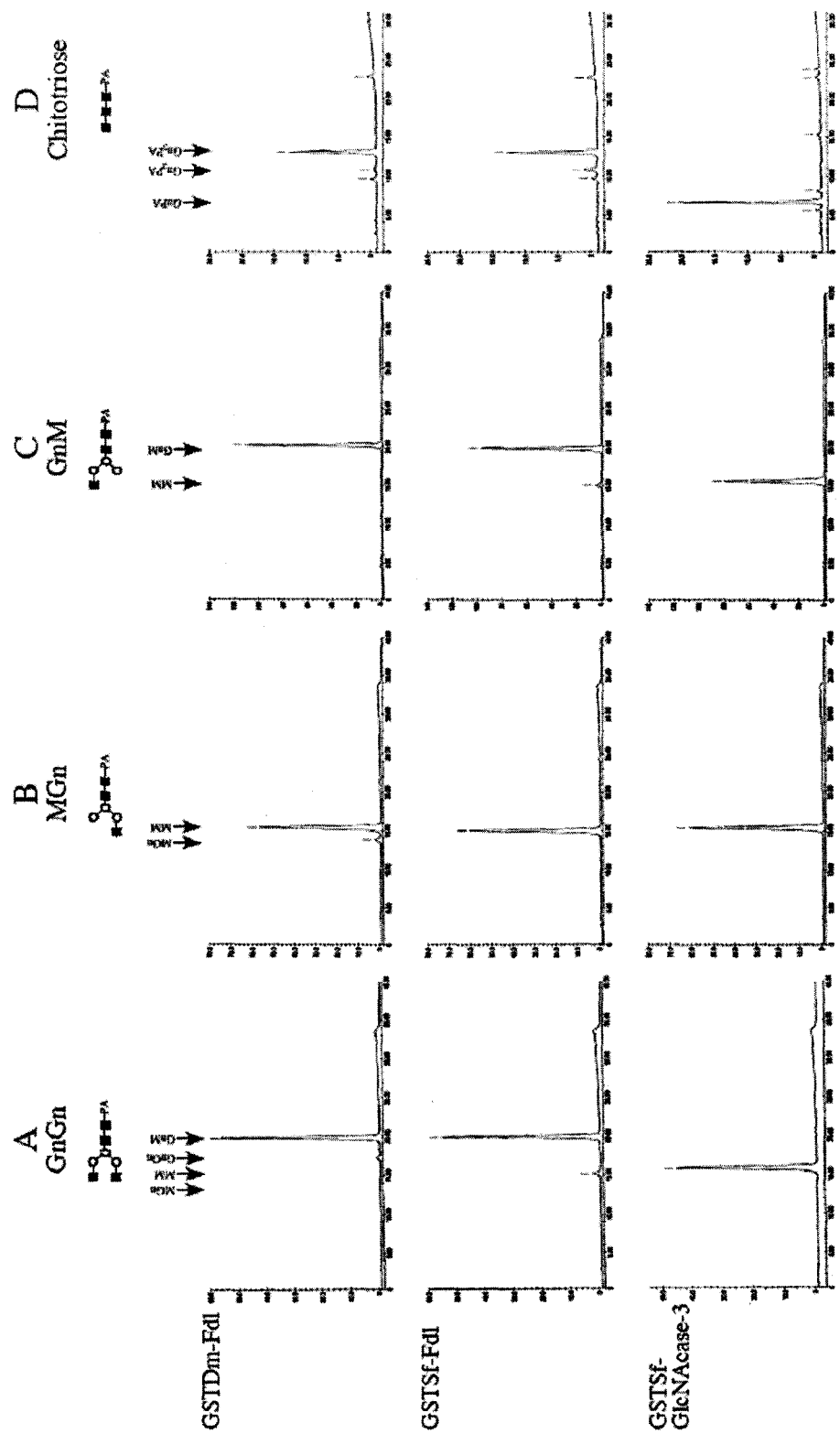
FIG. 7. Overdigestion of glycan substrates with the GST-tagged, ectodomains of Sf-FDL, Dm-FDL, and SfGlcNAcase-3/Sfhex. Equal amounts of each enzyme were incubated for 20 h with GnGn (A), GnM (B), or chitotriose (C) and the reaction products were recovered and analyzed by reverse-phase HPLC, as described in Experimental Procedures. The arrows show the elution times for each of the relevant glycans.

To examine their substrate specificities more stringently, we incubated the purified, GST-tagged ectodomains of Dm-FDL, Sf-FDL, and SfGlcNAcase-3/SfHex with the various synthetic glycan substrates for 20 h to achieve a ten-fold increase in the enzyme assay times (FIG. 7). The results of these assays verified that Dm-FDL and Sf-FDL are highly specific, even under this extreme condition. It can be seen that Sf-FDL produced tiny amounts of MGn from GnGn (FIG. 7A, middle panel) and tiny amounts of MM from GnM (FIG. 7C, middle panel). In addition, both Sf-FDL and Dm-FDL produced tiny amounts of chitobiose from chitotriose and none of the aforementioned products were observed when the relevant glycan substrates were mock-digested with elution buffer alone (data not shown). Nevertheless, Sf-FDL is clearly much more specific than SfGlcNAcase-3/SfHex and one would reasonably question the physiological relevance of the small amounts of conversion obtained under these extreme in vitro reaction conditions.

EXAMPLE II

Cloning of the TnFDL and BmFDL Genes

Common Materials and Methods

All PCRs were carried out in a final volume of 50 µLs in 1× of Phusion™ buffer GC with 0.2 mM of each dNTP, 1 µM of each primer, 1 M betaine, 0.6 U of Phusion™ DNA polymerase (NEB, Ipswich, Mass.) and 1 µL of template, except where indicated otherwise. All PCRs were carried out in a GeneAmp Model 2400 thermal cycler (Eppendorf, Foster City, Calif.). DNA extraction from agarose gel fragments were carried out using the QiaQuick™ Gel Extraction Kit (Qiagen, Valencia, Calif.) according to the manufacturer's instructions and eluted into 50 µLs.

Sequences obtained from degenerate and semidegenerate PCRs, TOPO® clones and RACE reactions were analyzed and assembled into full-length mRNA and genomic DNA sequences using ContigExpress, a component of Invitrogen Vector NTI 10.3.0.

T. ni fdl

Degenerate PCR

Genomic DNA was isolated from T. ni cells (Tn-4h cell line) according to the method of Laird et al. (Laird et al., 1991, Nucleic Acids Res. 19:4293). Degenerate PCRs were carried out using T. ni genomic DNA with the primers ASPDEG and SPDEG as described previously (Geisler et al., 2008, J. Biol. Chem. 283:11330-11339.). The spent reactions were separated on a 1.2% agarose gel and specific amplification products of the expected size (420 bp) were recovered from the gel, purified and directly sequenced with the same primers as used in the PCR.

Semi-Degenerate PCR

Semi-degenerate PCRs were carried out using T. ni genomic DNA to extend the sequence of the degenerate fragment towards both the 3' and the 5' end. Degenerate primers were designed against regions that are highly conserved between the SfFDL and the BmFDL conceptual translations. To obtain part of the TnFDL 5' end, a semi-degenerate PCR was carried out using primers TnFDL ASP2 and TnFDL SP4DEG. The PCR was incubated for 20 sec at 98° C., then cycled 25 times using (i) 10 sec at 98° C., (ii) 15 sec at 72 to 60° C. (with a decreasing temperature gradient of 0.5° C. per cycle), and (iii) 60 sec at 72° C. The reaction was cycled another 30 times using (i) 10 sec at 98° C., (ii) 15 sec at 60° C., and (iii) 60 sec at 72° C., and finally incubated for 2 min at 72° C. The spent reaction was separated on a 1.4% agarose gel and a specific amplification product of about the expected size (1100 bp) was recovered from the gel and purified. This DNA fragment was re-amplified using the TnFDL ASP3 and TnFDL SP4DEG primers using the same conditions, gel purified and directly sequenced using the same primers as used in the PCR.

To obtain part of the 3' end, a semi-degenerate PCR was carried out using primers TnFDL SP1 and TnFDL ASP6DEG with identical cycling conditions as specified above. The spent reaction was separated on a 1.4% agarose gel and a specific amplification product of about the expected size (730 bp) was recovered from the gel and purified. This fragment was cloned into pCR®2.1-TOPO® according to the manufacturer's instructions, and three clones were sequenced to yield a consensus sequence.

5' RACE

Total RNA was isolated from a mid-log culture of Tn-4h cells using the Qiagen RNeasy® Plus Mini Kit according to the manufacturer's instructions. 5' RACE-ready RNA was prepared from total RNA using the Invitrogen Generacer™ kit according to the manufacturer's instructions. Reverse transcription was carried out using Thermo-X™ reverse transcriptase with the TnFDL ASP1 primer. The reaction was set up according to the manufacturer's instructions and incubated for (i) 5 min at 50° C., (ii) 15 min at 55° C., (iii) 30 min at 60° C. and finally for (iv) 15 min at 60° C. The reaction was diluted with 40 µLs TE buffer and stored at −20° C.

5' RACE was carried out using the TnFDL ASP6 primer and the GeneRacer™ 5' Primer. The PCR was incubated for 30 sec at 96° C., then cycled 5 times using (i) 20 sec at 96° C., (ii) 60 sec at 72° C., after which the reaction was cycled 13 times using (i) 20 sec at 96° C., (ii) 20 sec at 72 to 60° C. (with a decreasing temperature gradient of 1° C. per cycle), and (iii) 40 sec at 72° C. The reaction was then cycled another 30 times using (i) 20 sec at 90° C., (ii) 20 sec at 60° C., and (iii) 40 sec at 72° C. The spent reaction was separated on a 1.4% agarose gel, and a specific amplification product of about 520 bps was isolated and purified. This DNA fragment was re-amplified using the GeneRacer™ 5' Nested Primer and either the TnFDL ASP6 or ASP7 primer. Reactions were incubated for 30 sec at 96° C., then cycled 5 times using (i) 20 sec at 96° C., (ii) 45 sec at 72° C., after which the reactions were cycled 13 times using (i) 20 sec at 96° C., (ii) 15 sec at 72 to 60° C. (with a decreasing temperature gradient of 1° C. per cycle), and (iii) 30 sec at 72° C. The reactions were then cycled another 30 times using (i) 20 sec at 96° C., (ii) 15 sec at 60° C., and (iii) 30 sec at 72° C. The spent reactions were separated on a 1.4% agarose gel, and specific amplification products of about 520 and 500 bps were isolated and directly sequenced using the TnFDL ASP6 or ASP7, respectively.

3' RACE

3' RACE-ready cDNA was prepared from total T. ni RNA isolated as described above. Reverse transcription was carried out using Thermo-X™ reverse transcriptase with the GeneRacer™ Oligo dT primer. The reaction was set up according to the manufacturer's instructions and incubated in the same fashion as for 5' RACE. The reaction was diluted with 40 µLs TE buffer and stored at −20° C.

3' RACE was carried out using the TnFDL SP4 primer and the GeneRacer™ 3' Primer. The PCR was incubated for 30 sec at 96° C., then cycled 5 times using (i) 20 sec at 96° C., (ii) 45 sec at 72° C., after which the reactions were cycled 13 times using (i) 20 sec at 96° C., (ii) 15 sec at 72 to 60° C. (with a decreasing temperature gradient of 1° C. per cycle), and (iii) 30 sec at 72° C. The reactions were then cycled another 30 times using (i) 20 sec at 96° C., (ii) 15 sec at 60° C., and (iii) 30 sec at 72° C. The spent reaction was separated on a 1.4% agarose gel, and a specific band of approximately 600 bps was isolated and purified. This DNA fragment was re-amplified using the TnFDL SP5 primer and the GeneRacer™ 3' Nested Primer. The PCRs were incubated for 15 sec at 96° C., then cycled 5 times using (i) 15 sec at 96° C., (ii) 35 sec at 72° C., after which reactions were cycled 13 times using (i) 15 sec at 96° C., (ii) 15 sec at 72 to 60° C. (with a decreasing temperature gradient of 1° C. per cycle), and (iii) 20 sec at 72° C. The reactions were the cycled another 30 times using (i) 15 sec at 96° C., (ii) 15 sec at 60° C., and (iii) 20 sec at 72° C. The spent reactions were separated on a 1.4% agarose gel, and a specific amplification product of 500 bps was isolated, purified and directly sequenced using the TnFDL SP5 primer.

Amplification of the Full-Length TnFDL Open Reading Frame for Baculovirus Expression The full-length open reading frame was amplified from both cDNA primed with the GeneRacer™ Oligo dT Primer as well as genomic DNA (including the intron) using the TnFDL FL SP2 BD and TnFDL ASP BD primers. The reactions were incubated for 20 sec at 98° C., the cycled 25 times using (i) 15 sec at 98° C., (ii) 10 sec at 72 to 60° C. (with a decreasing temperature gradient of 0.5° C. per cycle), and (iii) 60 sec at 72° C. The reactions were the cycled another 30 times using (i) 15 sec at 98° C., (ii) 10 sec at 60° C., and (iii) 60 sec at 72° C. The spent reactions were separated on a 1% agarose gel, and amplification products of the expected size were excised and purified. These DNA fragments from the reactions template by cDNA and gDNA were cloned into the pENTR™/D-TOPO® vector according to the manufacturer's instructions, yielding pENTR-TnFDL-C and pENTR-TnFDL-G, respectively. Four clones of each were sequenced, and a consensus clone of pENTR-TnFDL-C was used with Invitrogen's Baculodirect™ kit according to the manufacturer's instructions to yield AcTnFDL.

B. mori fdl

Bombyx mori Genomic Database Search Results

A tBLASTn search of the available Bombyx mori genomic sequences was carried out with the SfFDL conceptual translation as query using the online NCBI interface. This search yielded, amongst others, the sequences BAAB01046610, BAAB01083831 and BAAB01153187. The Sequence BAAB01046610 encodes a putative 5' coding exon with a start codon (nts 25-200). The conceptual translation of this exon shows high similarity to the amino-terminal part of SfFDL. The sequences BAAB01083831 and BAAB01153187 could be joined in silico to yield a contig encoding the putative 3' coding exon, including a stop codon. The conceptual translation of this exon showed high similarity to the carboxy-terminal part of SfFDL. The 5' coding exon could be joined in silico to the 3' coding exon at splice junctions predicted with high probability by NetGene2 (Hebsgaard et al., Nucleic Acids Res. 24:3439-3452), yielding a contiguous open reading frame.

Amplification of the Full-Length BmFDL Open Frame for Baculovirus Expression

Primers designed to amplify the entire predicted open reading frame with the additional sequence CACC 5' to the initiation codon were used in PCRs to amplify the open reading frame from cDNA as well as genomic DNA (including the intron). Genomic DNA was prepared by a modification of the method of Laird et al. (Supra) from a single stage 2 B. mori larva (Qiufeng/Baiyu hybrid). Briefly, the larva was homogenized in lysis buffer supplemented with RNAse A, after which the homogenate was incubated at 55° C. for 1 hour. The lysate was the centrifuged at 13.000×G to remove debris, and DNA was precipitated by additional of an equal volume of isopropyl alcohol. The DNA was dissolved in 500 µLs of TE buffer and cleaned once by phenol chloroform extraction. Total RNA was isolated from a single stage 2 B. mori larva (Qiufeng/Baiyu hybrid) using the Qiagen RNeasy™ Mini Plus kit. The larva was homogenized in Buffer RLT plus, followed by centrifugation at 13.000×G to remove debris. Total RNA was subsequently isolated according to the manufacturer's instructions. Total B. mori RNA was used to prepare 5' RACE-ready RNA using the Invitrogen GeneRacer™ kit according to the manufacturer's instructions. In two separate reactions, 5' RACE-ready RNA and total RNA was used for reverse transcription with Invitrogen Thermoscript™ reverse transcriptase using the BmFDL ASP1 primer and the GeneRacer™ Oligo dT Primer, respectively. The reaction was set up according to the manufacturer's instructions and incubated for (i) 5 min at 50° C., (ii) 15 at 55° C., (iii) 30 min at 60° C. and finally for (iv) 15 mins at 65° C. The reactions were diluted with 40 µLs TE buffer and stored at −20° C.

The predicted full-length open reading frame was amplified from both cDNA primed with GeneRacer™ Oligo dT Primer and genomic DNA (including the intron). The PCRs were set up using the BmFDL FL SP2 and BmFDL ASP1CLO primers and incubated in the same fashion as for the amplification of the full-length TnFDL open reading frame. The spent reactions were separated on a 1% agarose gel, and bands of the expected size were isolated and purified. The DNA fragments from the reactions template with genomic DNA and cDNA were cloned into the pENTR™/D-TOPO® vector according to the manufacturer's instructions, yielding pENTR-BmFDL-G and pENTR-BmFDL-C, respectively. Four clones of each were sequenced, yielding two distinct alleles from both gDNA and cDNA. Despite a substantial number of nucleotide substitutions, the conceptual translation of one of these alleles is identical to the conceptual translation of the putative fdl gene identified from the p50 (Daizo) strain. The two alleles differ between each other in several nucleotides in the intron and both exons. However, only three nucleotide changes are not silent, resulting in the L138I, the G404E and the H481Q amino acid changes. pENTR-BmFDL-C was used with Invitrogen's Baculodirect™ kit according to the manufacturer's instructions to generate AcBmFDL.

5' RACE

5' RACE was carried out using the BmFDL ASP4 primer and the GeneRacer™ 5' Primer with 5'RACE-ready cDNA prepared as described above. Reactions were incubated for 30 sec at 96° C., then cycled 5 times using (i) 15 sec at 96° C., (ii) 45 sec at 72° C., after which the reactions were cycled 12 times using (i) 15 sec at 96° C., (ii) 15 sec at 72 to 61° C. (with a decreasing temperature gradient of 1° C. per cycle), and (iii) 30 sec at 72° C. The reactions were the cycled another 30 times using (i) 15 sec at 96° C., (ii) 15 sec at 61° C. and (iii) 30 sec at 72° C., and finally incubated for 1 min at 72° C. The spent reactions were separated on a 1.2% agarose gel. A specific band of about 570 bps was isolated, purified and re-amplified using the BmFDL ASP5 primer and the GeneRacer™ 5' Nested Primer using the same cycling conditions. The nested 5' RACE reactions were separated on a 1.4% agarose gel, showing a specific band of the expected 550 bps. This band was excised, purified and sequenced using the BmFDL ASP5 primer.

3' RACE

3' RACE was carried out using the BmFDL SP4 primer and the GeneRacer™ 3' Primer with 3' RACE-ready cDNA. Reactions were cycled in the same fashion as described above for 5' RACE. The spent reaction was analyzed on a 1.4% agarose gel, showing a specific faint band at 450 bps. This band was excised, purified and used for nested 3' RACE reactions with the BmFDL SP5 primer and the GeneRacer™ 3' Nested Primer using the same cycling reactions. The spent reactions showed a strong, specific band at the expected size of 420 bps. This band was excised, purified and sequenced using the BmFDL SP5 primer.

Primer Table
(sequences are SEQ ID NOs: 10, 11, and 34-56, from top to bottom)

| Primer name | Nucleotide sequence (5' → 3') |
|---|---|
| ASPDEG | CGC AGT CSA RRT ACC AVG CRT CVA C |
| SPDEG | TAC TGC GGH GAR CCN CCN TGY GG |
| TnFDL ASP2 | ACA CCT GCA CGC CTA GGT GAC |
| TnFDL SP4DEG | RYT NTG GCC NCA RCC NAC NGG |
| TnFDL ASP3 | GTC TAG CCG CTC TAA GTA CGG TG |
| TnFDL SP1 | TTG ACG GAG GTC GAC GAC CTG |
| TnFDLASP6DEG | GCR TGN GGR TTR TGN SWR CAC C |
| TnFDL ASP1 | TGC GAG ATC ACG GTC CGG AAT C |
| TnFDL ASP6 | TCC GAC ACATCA CGA GAA GGA GAC |
| TnFDL ASP7 | GAG ACG TGA CGA TCT GCA GCT TG |
| TnFDL SP4 | GTG CCA GTG GAC GGA GCA GCT G |
| TnFDL SP5 | CGC GGC GGC CGA CGT GTA CCT |
| TnFDL FL SP2 BD | CAC CAT GAA GTG GTG GGG CGA CGC A |
| TnFDL FL ASP2 BD | CTA GAG GCA GGC GTG CGG GTT G |
| BmFDL ASP1 | ACG TCG TCG GAC GTG TAC ACT G |
| BmFDL ASP4 | TGT GGC CAG AGC TGG GTG GAG |
| BmFDL ASP5 | GAG GCG CAC AGC ATG TTG CAA GTC |
| BmFDL SP4 | GAT GTG TAC TTG CGG CTC GAC AC |
| BmFDL SP5 | GTA CTT GCG GCT CGA CAC ACA GC |
| BmFDL FL SP2 | CAC CAT GAT GTC GTG GGG TGA TG |
| BmFDL ASP1CLO | ACT AGA GGC ACG CGT GCG G |
| GeneRacer™ 5' Primer | CGA CTG GAG CAC GAG GAC ACT GA |
| GeneRacer™ 5' Nested Primer | GGA CAC TGA CAT GGA CTG AAG GAG TA |
| GeneRacer™ 3' Primer | GCT GTC AAC GAT ACG CTA CGT AAC G |
| GeneRacer™ 3' Nested Primer | CGC TAC GTA ACG GCA TGA CAG TG |

EXAMPLE III

Figure 11:
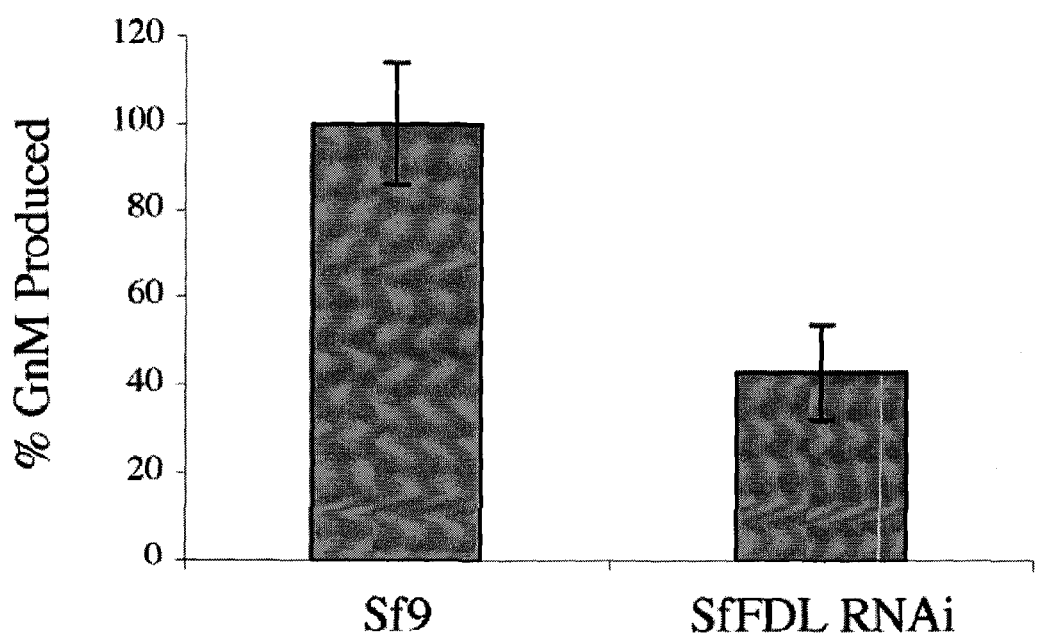
FIG. 11. Endogenous levels of specific, processing β-N-acetylglucosaminidase activity in parental Sf9 cells and an Sf9-derived clone expressing an Sf-fdl-specific double-stranded RNA. Microsomal membrane preparations from Sf9 or SfFDL RNAi cells were incubated for 16 hr with GnGn, and the reaction products were analyzed by HPLC to compare the relative amounts of GnM produced. The plot shows the average results obtained in five replicate assays, with the average percentage of GnM produced by microsomes from the Sf9 controls set to 100%. The error bars show the standard deviations and a one-way ANOVA analysis showed that the two datasets are significantly different (P<0.01).

Inhibition of Specific, Processing β-N-acetyglucosaminidase Activity by an Sf-fdl-Specific Double-Stranded RNA If the Sf-fdl gene encodes the specific, processing β-N-acetylglucosaminidase activity in Sf9 cells, it should be possible to reduce this activity by RNA interference with Sf-fdl-specific double-stranded RNA. Towards this end, we constructed an immediate early expression plasmid encoding an inverted repeat sequence derived from a portion of the Sf-fdl coding sequence (FIG. 12) and used it to isolate a transformed Sf9 cell subclone, as described above. Microsomal membranes were then isolated from the parental cell line or the subclone and used for β-N-acetylglucosaminidase activity assays with GnGn as the substrate. HPLC analysis of the reaction products showed that the microsomal membranes from both the parental Sf9 cells the transformed subclone converted GnGn to GnM, but not detectably to MM or MGn (data not shown). Thus, in this examination of endogenous β-N-acetylglucosaminidase activities in microsomal membranes from uninfected Sf9 cells, we detected only the specific, processing enzyme activity. Furthermore, we found that the levels of this specific, processing β-N-acetylglucosaminidase activity were over 50% lower in the membranes from the transformed subclone, relative to the parental controls (FIG. 11). The reduced levels of specific, processing β-N-acetylglucosaminidase activity in the Sf9 subclone transformed with the constitutive expression plasmid encoding Sf-fdl-specific double-stranded RNA strongly supports the conclusion that the Sf-fdl gene encodes this activity.

While SEQ ID NO:9 is specific for downregulating expression of the Sf fdl encoding nucleic acid, provision of the sequence information for *T. ni* and *B. mori* homologs readily enables the skilled artisan to generate additional specific RNAi for inhibiting expression of the same. Indeed, computer programs are available online which can assist in the design of such molecules.

From the foregoing description, those skilled in the art will appreciate that the presence or absence of a specific, processing β-N-acetylglucosaminidase is a key difference in the protein N-glycan processing pathways of insects and higher eukaryotes. In insect systems, this function was first identified as an enzyme activity in crude microsomal membranes isolated from a cell line derived from the lepidopteran insect, *S. frugiperda* (9). Efforts to molecularly clone the gene encoding this enzyme in these cells yielded two recent reports describing a single gene alternatively termed SfGlcNAcase-3 (18) and SfHex (17). Biochemical assays revealed that the SfGlcNAcase-3/SfHex gene product lacked the strict substrate specificity of the enzyme activity originally described by Altmann and co-workers in 1995. Based upon this and other findings, one group concluded in their report that the SfGlcNAcase 3/SfHex gene product is more likely to be involved in glycan and chitin degradation than in N-glycan processing (18). In contrast, based upon a slight preference for the appropriate substrate, the other group concluded in their report that this gene product is involved in N-glycan processing and hypothesized that it serves multifunctional roles in both N-glycan processing and glycan degradation in Sf9 cells (17). Parallel efforts to molecularly clone the processing β-N-acetylglucosaminidase from *Drosophila melanogaster* yielded a report describing the Dm-Fdl gene and the characteristics of the gene product (16). Based upon its substrate specificity and the presence of a higher level of N-glycans containing terminal N-acetylglucosamine residues in mutant flies lacking a functional Fdl gene, this report concluded that the Fdl gene encoded the β-N-acetylglucosaminidase involved in N-glycan processing in this fruitfly.

In accordance with the present invention, we isolated an Fdl gene from Sf9 cells and demonstrated that it encodes a membrane-associated β-N-acetylglucosaminidase with the same, strict substrate specificity exhibited by Dm-FDL and by the enzyme activity originally detected in *S. frugiperda* microsomes (9). The fact that the Sf9 genome encodes a gene with a close phylogenetic relationship to Dm-fdl, the fact that the Sf-fdl gene product is membrane-associated and has the strict substrate specificity and pH optimum profile of the original activity detected in *S. frugiperda* microsomes, and the fact that Sf9 cells engineered to express Sf-Fdl-specific double-stranded RNA have lower levels of specific, processing β-N-acetylglucosaminidase activity all tend to support the view that the Sf-fdl gene encodes the β-N-acetylglucosaminidase involved in N-glycan processing in Sf9 cells. In addition, these findings support our previous conclusion that the broad spectrum β-N-acetylglucosaminidase encoded by the SfGlcNAcase 3/SfHex gene is more likely involved in glycan and chitin degradation.

The fdl gene orthologs were isolated from the lepidopteran insect cell species, *Spodoptera frugiperida, Trichoplusia ni* and *Bombyx mori*, as cell lines derived from these insect species are commonly used with the baculovirus expression system.

REFERENCES

1. Marz, L., Altmann, F., Staudacher, E., and Kubelka, V. (1995) Protein glycosylation in insects. In: Montreuil, J., Vliegenthart, J. F. G., and Schachter, H. (eds). *Glycoproteins*, Elsevier, Amsterdam
2. Marchal, I., Jarvis, D. L., Cacan, R., and Verbert, A. (2001) *Biol. Chem.* 382, 151-159
3. O'Reilly, D. R., Miller, L. K., and Luckow, V. A. (1992) *Baculovirus expression vectors*, W.H. Freeman and Company, New York
4. Summers, M. D., and Smith, G. E. (1987) *Tx. Ag. Expt. Stn. Bull. No.* 1555
5. Jarvis, D. L. (1997) Baculovirus expression vectors. In: Miller, L. K. (ed). *The Baculoviruses*, Plenum Press, New York
6. Fischer, R., Stoger, E., Schillberg, S., Christou, P., and Twyman, R. M. (2004) *Curr. Op. Plant Biol.* 7(2), 152-158
7. Ma, J. K., Drake, P. M., and Christou, P. (2003) *Nat. Rev. Genet.* 4(10), 794-805
8. Kornfeld, R., and Kornfeld, S. (1985) *Ann. Rev. Biochem.* 54, 631-664
9. Altmann, F., Schwihla, H., Staudacher, E., Glossl, J., and Marz, L. (1995) *J. Biol. Chem.* 270, 17344-17349
10. Zhang, W., Cao, P., Chen, S., Spence, A. M., Zhu, S., Staudacher, E., and Schachter, H. (2003) *Biochem. J.* 372 (Pt 1), 53-64
11. Gutternigg, M., Kretschmer-Lubich, D., Paschinger, K., Rendic, D., Hader, J., Geier, P., Ranftl, R., Jantsch, V., Lochnit, G., and Wilson, I. B. (2007) *J. Biol. Chem.* 282 (38), 27825-27840
12. Vitale, A., and Chrispeels, M. J. (1984) *J. Cell Biol.* 99(1 Pt 1), 133-140
13. Sturm, A. (1995) N-glycosylation of proteins in plants. In: Montreuil, J., Vliegenthart, J. F. G., and Schachter, H. (eds). *Glycoproteins*, Elsevier, Amsterdam
14. Vaughn, J. L., Goodwin, R. H., Thompkins, G. J., and McCawley, P. (1977) *In Vitro* 13, 213-217
15. Wagner, R., Geyer, H., Geyer, R., and Klenk, H. D. (1996) *J. Virol.* 70(6), 4103-4109
16. Leonard, R., Rendic, D., Rabouille, C., Wilson, I. B., Preat, T., and Altmann, F. (2006) *J. Biol. Chem.* 281(8), 4867-4875
17. Tomiya, N., Narang, S., Park, J., Abdul-Rahman, B., Choi, O., Singh, S., Hiratake, J., Sakata, K., Betenbaugh, M. J., Palter, K. B., and Lee, Y. C. (2006) *J. Biol. Chem.* 281(28), 19545-19560
18. Aumiller, J. J., Hollister, J., and Jarvis, D. L. (2006) *Prot. Expr. Purif* 47, 571-590
19. Altschul, S. F., Madden, T. L., Schaffer, A. A., Zhang, J., Zhang, Z., Miller, W., and Lipman, D. J. (1997) *Nucl. Acids Res.* 25, 3389-3402
20. Brunak, S., Engelbrecht, J., and Knudsen, S. (1991) *J Mol Biol* 220(1), 49-65
21. Thompson, J. D., Gibson, T. J., Plewniak, F., Jeanmougin, F., and Higgins, D. G. (1997) *Nucl. Acids Res.* 25, 4876-4882
22. Innis, M. A., and Gelfand, D. H. (1990) Optimization of PCRs. In: Innis, M. A., Gelfand, D. H., Sninsky, J. J., and White, T. J. (eds). *PCR Protocols: A Guide to Methods and Applications*, Academic Press, San Diego
23. Sambrook, J., Fritsch, E. F., and Maniatis, T. (1989) *Molecular Cloning: A Laboratory Manual*, 2nd edition Ed., Cold Spring Harbor Press, Cold Spring Harbor, N.Y.
24. Shi, X., and Jarvis, D. L. (2006) *Analyt Biochem* 356(2), 222-228
25. Hofmann, K., and Stoffel, W. (1993) *Biol. Chem. Hoppe-Seyler* 374, 166
26. Kitts, P. A., and Possee, R. D. (1993) *Biotechniques* 14(5), 810-817
27. Bao and Cagan (2006) *RNA*, 12, 2020-2024
28. Jarvis, D. L., Weinkauf, C., and Guarino, L. A. (1996) *Prot. Expr. Purif.* 8, 191-203
29. von Heijne, G. (1992) *J. Mol. Biol.* 225(2), 487-494
30. Paulson, J. C., and Colley, K. J. (1989) *J. Biol. Chem.* 264, 17615-17618
31. Breton, C., Mucha, J., and Jeanneau, C. (2001) *Biochimie* 83(8), 713-718.
32. Field, M. C., and Wainwright, L. J. (1995) *Glycobiology* 5, 463-472
33. Myerowitz, R., Piekarz, R., Neufeld, E. F., Shows, T. B., and Suzuki, K. (1985) *Proceedings of the National Academy of Science of the United States of America* 82(23), 7830-7834
34. O'Dowd, B. F., Quan, F., Willard, H. F., Lamhonwah, A. M., Korneluk, R. G., Lowden, J. A., Gravel, R. A., and Mahuran, D. J. (1985) *Proceedings of the National Academy of Science of the United States of America* 82(4), 1184-1188
35. Gaunt, M. W., and Miles, M. A. (2002) *Mol. Biol. Evol.* 19, 748-761
36. Felsenstein, J. (1989) *Cladistics* 5, 164-166.

While certain of the preferred embodiments of the present invention have been described and specifically exemplified above, it is not intended that the invention be limited to such embodiments. Various modifications may be made thereto without departing from the scope and spirit of the present invention, as set forth in the following claims. Furthermore, the transitional phases "comprising", "consisting essentially of" and "consisting of" define the scope of the appended claims, in original and amended form, with respect to what unrecited additional claim elements or steps. The term "comprising" is intended to be inclusive or open-ended and does not exclude additional, unrecited elements, methods step or materials. The phrase "consisting of" excludes any element, step or material other than those specified in the claim, and, in the latter instance, impurities ordinarily associated with the specified materials. The phrase "consisting essentially of" limits the scope of a claim to the specified elements, steps or materials and those that do not materially affect the basic and novel characteristic(s) of the claimed invention. All compositions or formulations identified herein can, in alternate embodiments, be more specifically defined by any of the transitional phases "comprising", "consisting essentially of" and "consisting of".

What is claimed is:

1. A cDNA encoding an β-N-acetylglucosaminidase having a sequence selected from the group consisting of SEQ ID NO: 2, SEQ ID NO:4, SEQ ID NO:6 and SEQ ID NO:8.

2. A cDNA encoding an β-N-acetylglucosaminidase of SEQ ID NO:2.

3. A cDNA encoding an β-N-acetylglucosaminidase of SEQ ID NO:4.

4. A cDNA encoding an β-N-acetylglucosaminidase of SEQ ID NO:6.

5. A cDNA encoding an β-N-acetylglucosaminidase of SEQ ID NO:8.

6. The cDNA of claim 1, which is SEQ ID NO:1.

7. The cDNA of claim 1, which is SEQ ID NO:3.

8. The cDNA of claim 1, which is SEQ ID NO:5.

9. The cDNA of claim 1, which is SEQ ID NO:7.

10. An expression vector comprising at least one isolated nucleic acid encoding a B—N-acetylglucosaminidase having a sequence selected from the group consisting of SEQ ID NO: 2, SEQ ID NO: 4, SEQ ID NO: 6 and SEQ ID NO: 8.

11. A recombinant insect cell transformed with the expression vector of claim 10.

12. A molecule of RNA transcribed from a cDNA of SEQ ID NO: 9, said RNA being double stranded; wherein said molecule of RNA consists of the full length of transcribed SEQ ID NO: 9.

13. An expression vector comprising the RNA molecule of claim 12.

14. A recombinant transgenic insect cell comprising the expression vector of claim 13.

15. The recombinant insect cells of claim 14, further comprising at least one glycosylation enzyme selected from the group consisting of N-acetylglucosaminyltransferases, galactosyltransferases, sialyltransferases, sulfotransferases, sialic acid synthases, CPM-sialic acid synthetases, UDP-N-acetylglucosamine-2-epimerases/N-acetylmannosamine kinases, and CMP-sialic acid transporters.

16. A method for inhibiting β-N-acetylglucosaminidase activity comprising contacting a Sf-fdl-expressing cell with a molecule of RNA as claimed in claim 12, in an amount effective to down-regulate β-N-acetylglucosaminidase endogenous to that cell.

17. A method for enhancing production of mammalian-like N-glycans in insect cells, comprising a) providing the recombinant insect cells of claim 14;
b) transforming said cells with an expression vector comprising a nucleic acid encoding a heterologous glycoprotein of interest, said glycoprotein expressed in said cells of a) comprising elevated levels of mammalian-like N-glycans when compared to levels observed in wild type cells.

\* \* \* \* \*